(12) United States Patent  
Cheng et al.

(10) Patent No.: US 9,399,044 B2
(45) Date of Patent: Jul. 26, 2016

(54) ANTIMICROBIAL CATIONIC POLYAMINES

(71) Applicants: International Business Machines Corporation, Armonk, NY (US); Agency For Science, Technology and Research, Singapore (SG)

(72) Inventors: Wei Cheng, Singapore (SG); Xin Ding, Singapore (SG); Jeannette M. Garcia, San Jose, CA (US); James L. Hedrick, Pleasanton, CA (US); Chuan Yang, Singapore (SG); Yi Yan Yang, Singapore (SG)

(73) Assignees: International Business Machines Corporation, Armonk, NY (US); Agency For Science, Technology And Research, Singapore (SG)

( * ) Notice: Subject to any disclaimer, the term of this patent is extended or adjusted under 35 U.S.C. 154(b) by 0 days.

(21) Appl. No.: 14/288,782

(22) Filed: May 28, 2014

(65) Prior Publication Data

US 2015/0342984 A1      Dec. 3, 2015

(51) Int. Cl.
| | | |
|---|---|---|
| *A01N 63/00* | (2006.01) | |
| *A01N 37/44* | (2006.01) | |
| *A61K 31/785* | (2006.01) | |
| *C08G 73/02* | (2006.01) | |
| *A01N 37/46* | (2006.01) | |
| *A01N 33/04* | (2006.01) | |
| *A01N 47/30* | (2006.01) | |

(52) U.S. Cl.
CPC .............. *A61K 31/785* (2013.01); *A01N 33/04* (2013.01); *A01N 37/46* (2013.01); *A01N 47/30* (2013.01); *C08G 73/0226* (2013.01)

(58) Field of Classification Search
None
See application file for complete search history.

(56) References Cited

U.S. PATENT DOCUMENTS

| 7,262,221 B2 | 8/2007 | Uhrich et al. |
| 2004/0152769 A1 | 8/2004 | Ekwuribe et al. |
| 2006/0239961 A1 | 10/2006 | Bentley et al. |
| 2008/0051323 A1 | 2/2008 | Kosak |
| 2009/0246258 A1 | 10/2009 | Shukla et al. |

(Continued)

FOREIGN PATENT DOCUMENTS

| IL | WO 2009027971 A2 * | 3/2009 | ............. A01N 33/12 |
| WO | 2013159092 A1 | 10/2013 | |

OTHER PUBLICATIONS

Gibney, et al., "Poly(ethylene imine)s as antimicrobial agents with selective activity", Macromol Biosci. 2012, 12(9): 1279-1289.

(Continued)

*Primary Examiner* — Robert A Wax
*Assistant Examiner* — Melissa Mercier
(74) *Attorney, Agent, or Firm* — Michael R. Roberts

(57) ABSTRACT

Antimicrobial, non-hemolytic cationic polyamines were prepared by treating partially N-acylated polyethylenimines and/or partially oxidized polyethylenimines with a protic acid. The cationic polyamines can have a linear or branched polyethylenimine backbone structure. Preferably, the cationic polyamines comprise pendant urea groups, which can be introduced via a cyclic carbonate comprising a pendant urea group. The cationic polyamines can be active against a tuberculosis *mycobacterium* at low concentration. The cationic polyamines are also effective against Gram-negative *Escherichia coli* and *Pseudomonas aeruginosa*, Gram-positive *Staphylococcus aureus*, and fungus *Candida albicans* in solution and in the form of a film.

40 Claims, 18 Drawing Sheets

(56) References Cited

U.S. PATENT DOCUMENTS

| | | |
|---|---|---|
| 2010/0292623 A1 | 11/2010 | Greiner et al. |
| 2011/0171279 A1 | 7/2011 | Chisholm et al. |
| 2013/0017332 A1 | 1/2013 | Messersmith et al. |

OTHER PUBLICATIONS

Haas, et al., "Oxidized Polyethylenimine", Journal of Polymer Science: Polymer Chemistry Edition vol. 10. 3143-3158 (1972).

Haldar, et al., "Polymeric coatings that inactivate both influenza virus and pathogenic bacteria", PNAS, Nov. 21, 2006, vol. 103, No. 47 17667-17671.

He, et al., "Synthesis and Characterization of Amphiphilic Monodisperse Compounds and Poly(ethylene imine)s: Influence of Their Microstructures on the Antimicrobial Properties," Biomacromolecules 2012, 13, 612-623; Published: Feb. 7, 2012.

Klibanov, "Permanently microbicidal materials coatings", J. Mater. Chem., 2007, 17, 2479-2482.

Lee, et al., "Mussel-Inspired Surface Chemistry for Multifunctional Coatings", Science. Oct. 19, 2007; 318(5849): 426-430.

Lee, et al., "Substrate-Independent Layer-by-Layer Assembly by Using Mussel-Adhesive-Inspired Polymers," Adv Mater. May 5, 2008; 20(9): 1619-1623.

Mukherjee, et al., 'Practical Aspects of Hydrophobic Polycationic Bactericidal "Paints"', Appl Biochem Biotechnol (2008) 151:61-70.

Park, et al., "One-Step, Painting-Like Coating Procedures to Make Surfaces Highly and Permanently Bactericidal," Biotechnol. Prog. 2006, 22, 584-589.

Schaer, et al., "Hydrophobic polycationic coatings that inhibit biofilms and support bone healing during infection", Biomaterials 33 (2012) 1245-1254.

Tanaka et al., "Proton conducting behavior in non-crosslinked and crosslinked polyethylenimine with excess phosphoric acid," Electrochimica Acta 45 (2000) 1385-1389.

Erbacher et al., "Genuine DNA/polyethylenimine (PEI) Complexes Improve Transfection Properties and Cell Survival," Journal of Drug Targeting, May 2004 vol. 12 (4), pp. 223-236.

Fortune et al., "Highly Effective Gene Transfection In Vivo by Alkylated Polyethylenimine," Journal of Drug Delivery, vol. 2011, Article ID 204058, 6 pages, 2011.

Fukumoto et al., "Cost-effective gene transfection by DNA compaction at pH 4.0 using acidified, long shelf-life polyethylenimine," Cytotechnology. Jan. 2010; 62(1): 73-82.

Gao et al., "Studies on the preparation and antibacterial properties of quaternized polyethyleneimine," Journal of Biomaterials Science, Polymer Edition, vol. 18, No. 5, pp. 531-544 (2007).

Gibney, "Polymeric Antibacterial Agents: Cytotoxicity and Antimicrobial Properties of Amphiphilic Polymers," Thesis, Department of Chemistry, University of Michigan, Apr. 29, 2009.

Grzegorzewicz, et al. "Inhibition of mycolic acid transport across the *Mycobacterium tuberculosis* plasma membrane," Nature Chemical Biology, vol. 8, Apr. 2012. pp. 334-341.

Kem, K. M. (1979), Kinetics of the hydrolysis of linear poly[(acylimino)-ethylenes]. J. Polym. Sci. Polym. Chem. Ed., 17: 1977-1990; Abstract.

Liu et al., "Hyperbranched polyethylenimines as versatile precursors for the preparation of different type of unimolecular micelles," Reactive & Functional Polymers 67 (2007) 383-395; Available online Feb. 4, 2007.

Pasquier, et al. "Amphiphilic Branched Polymers as Antimicrobial Agents," Macromol. Biosci. 2008, 8, 903-915.

Pasquier, et al. "From Multifunctionalized Poly(ethylene imine)s toward Antimicrobial Coatings," Biomacromolecules, 2007, 8 (9), 2874-2882.

Pastor-Perez et al., "Unprecedented Blue Intrinsic Photoluminescence from Hyperbranched and Linear Polyethylenimines: Polymer Architectures and pH-Effects," Macromol. Rapid Commun. 2007, 28, 1404-1409.

Pratt, et al. "Exploration, Optimization, and Application of Supramolecular Thiourea-Amine Catalysts for the Synthesis of Lactide (Co)polymers", Macromolecules 2006, 39, 7863-7871. Published on Web Oct. 18, 2006.

Spoden et al., "Polyethylenimine Is a Strong Inhibitor of Human Papillomavirus and Cytomegalovirus Infection," Antimicrob. Agents Chemother. 2012, 56(1):75. Published Ahead of Print Oct. 3, 2011.

Tanaka et al., "H igh molecular weight linear polyethylenimine and poly(N-methylethylenimine)," Macromolecules, 1983, 16 (6), pp. 849-853 (first page).

Tauhardt, et al., "Linear Polyethyleneimine: Optimized Synthesis and Characterization—On the Way to "Pharmagrade" Batches," Macromol. Chem. Phys. 2011, 212, 1918-1924.

Teo et al., "Hydrophobic modification of low molecular weight polyethylenimine for improved gene transfection," Biomaterials 34 (2013) 7971-7979. Available online Jul. 21, 2013.

Thomas et al., "Full deacylation of polyethylenimine dramatically boosts its gene delivery efficiency and specificity to mouse lung," PNAS Apr. 19, 2005 vol. 102 No. 16 5679-5684.

Von Harpe et al., "Characterization of commercially available and synthesized polyethylenimines for gene delivery," Journal of Controlled Release 69 (2000) 309-322.

Yue et al., "Progress and perspectives in developing polymeric vectors for in vitro gene delivery," BiomatSci 2013, 1, p. 152-170; published Oct. 1, 2012.

* cited by examiner

Untreated Contact Lens

B5

B6

B7

B8

Untreated Contact Lens
48.4°±0.6°

B5  76.6°±1.3°

B6  67.4°±0.8°

B7  61.4°±1.0°

ANTIMICROBIAL CATIONIC POLYAMINES

PARTIES TO A JOINT RESEARCH AGREEMENT

This invention was made under a joint research agreement between International Business Machines Corporation and the Agency for Science, Technology and Research.

BACKGROUND

The invention relates to antimicrobial cationic polyamines, and more specifically, to cationic modified polyethylenimines for antimicrobial applications.

The rapid emergence of antibiotic-resistant infections, which makes infectious diseases increasingly difficult to control with the existing classes of antibiotics, has caused a great concern in the healthcare field and provided an impetus for continued antimicrobial development.

Multicellular organisms naturally defend themselves against infections from opportunistic pathogens using host defense peptides. These antimicrobial peptides were effective against a broad spectrum of pathogens, such as Gram-positive and Gram-negative bacteria, fungi and protozoa. The cationic amphiphilic peptides enter the lipid domain of bacterial cell membrane and disintegrate the cell membrane. However, the clinical application of antimicrobial peptides is limited because the peptides are generally sensitive to enzymatic degradation, are toxic, and are expensive for large-scale production.

Polyethylenimines (PEIs) are polyamines, and are commercially available in a broad range of molecular weights. The PEIs are formed as either linear (LPEI) or branched (BPEI) macromolecules. PEIs have found many applications in products, such as detergents, adhesives, water treatment agents, and cosmetics. Due to their ability to enter a cell through the cell membrane, PEIs have been utilized as drug carriers in biomedical applications. Polycationic PEIs can mediate gene transfer into mammalian cells in vitro and in vivo as a complex with DNA.

PEIs have also displayed antimicrobial activity after chemical modification. For example, quaternized BPEI (QPEI) showed antimicrobial ability against *Escherichia coli* (*E. coli*) at low concentrations (Gao, et al., J. Biomaterial Science, Polymer Edition, 2007, 18, 531-544). As another example, BPEI quaternized with long alkyl groups exhibited some degree of antimicrobial activity against *E. coli* (Pasquier, et al., Biomacromolecules, 2007, 8, 2874-2882). As another example, LPEI was grafted with long alkyl chains to produce a series of hydrophobically modified water insoluble LPEI derivatives, which were painted on a glass slide using an organic solvent (Fortune, et al., J. Drug Delivery, 2011, Article ID 204058). The coatings killed *E. coli* and *Staphylococcus aureus* (*S. aureus*) effectively.

Recently, the antimicrobial properties of linear and branched PEIs of various molecular weights was studied (K. Gibney, Thesis, University of Michigan, 2009). LPEIs generally showed higher activity against *E. coli* and *S. aureus* than BPEIs, but were more hemolytic to human red blood cells (human RBCs). Moreover, compared to water-miscible BPEI, LPEI is not easily dissolved in water even at room temperature. To prepare LPEI aqueous solution, a small volume of ethanol can be added to facilitate LPEI dissolution.

An ongoing need exists for broad spectrum antimicrobial agents that are non-hemolytic.

SUMMARY

Accordingly, a method is disclosed, comprising:
treating a medical condition caused by at least one bacterium by contacting the bacterium with a cationic polyamine, thereby killing the bacterium, wherein the cationic polyamine has a polymer backbone comprising:
i) a positive-charged first ethylenimine unit of formula (2):

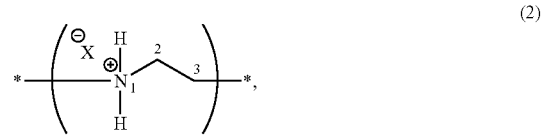

(2)

wherein $X^{\ominus}$ is a negative-charged counterion bound by non-covalent association with the positive charged nitrogen labeled 1, and
ii) a non-charged second ethylenimine unit of formula (3):

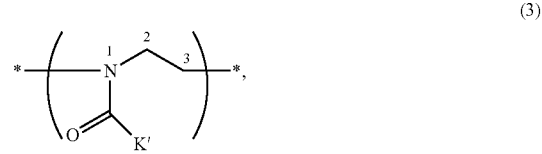

(3)

wherein K' comprises at least one carbon;
and wherein
the cationic polyamine has a hemolysis HC20 value of greater than 1000 mg/L, and
the first ethylenimine unit and the second ethylenimine unit of the polymer backbone are directly and/or indirectly covalently linked.

Also disclosed is a drug, comprising:
a cationic polyamine, wherein the cationic polyamine has a polymer backbone comprising:
i) a positive-charged first ethylenimine unit of formula (2):

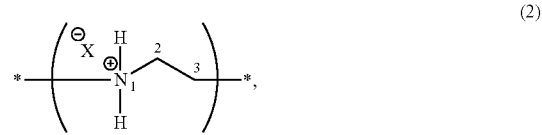

(2)

wherein $X^{\ominus}$ is a negative-charged counterion bound by non-covalent association with the positive charged nitrogen labeled 1, and
ii) a non-charged second ethylenimine unit of formula (3):

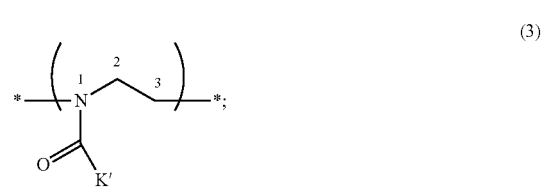

(3)

wherein K' comprises at least one carbon;
and wherein
the first ethylenimine unit and the second ethylenimine unit are directly and/or indirectly covalently linked, the drug is effective in killing a bacterium, and the drug has a hemolysis HC20 value of greater than 1000 mg/L.

Further disclosed is a method, comprising:

forming a mixture comprising i) a base polyamine selected from the group consisting of polyethylenimines, partially N-acylated polyethylenimines, and combinations thereof, and ii) a solvent, treating the mixture with oxygen and/or a peroxide, thereby forming an oxidized base polyamine; and treating the oxidized base polyamine with a protic acid, thereby forming an oxidized cationic polyamine having a polymer backbone that comprises:

a positive-charged first ethylenimine unit of formula (2):

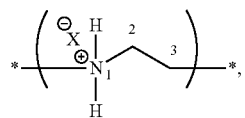

(2)

wherein $X^{\ominus}$ is a negative-charged counterion bound by non-covalent association with the positive charged nitrogen labeled 1, and an oxidized ethylenimine unit of formula (7):

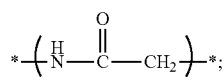

(7)

wherein the first ethylenimine unit and the oxidized ethylenimine unit are directly and/or indirectly covalently linked, the cationic polyamine is effective in killing a bacterium, and the cationic polyamine has a hemolysis HC20 value of greater than 1000 mg/L.

Also disclosed is an antimicrobial film, wherein the film comprises a cationic polyamine having a polymer backbone that comprises:

i) a positive-charged first ethylenimine unit of formula (2):

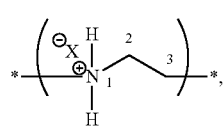

(2)

wherein $X^{\ominus}$ is a negative-charged counterion bound by non-covalent association with the positive charged nitrogen labeled 1, and ii) a non-charged second ethylenimine unit of formula (3):

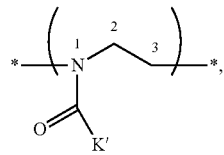

(3)

wherein K' comprises at least one carbon;

and wherein the first ethylenimine unit and the second ethylenimine unit are directly and/or indirectly covalently linked.

Further disclosed is an article comprising an above-described film disposed on a surface of an object.

The above-described and other features and advantages of the present invention will be appreciated and understood by those skilled in the art from the following detailed description, drawings, and appended claims.

DETAILED DESCRIPTION

Figure 1:
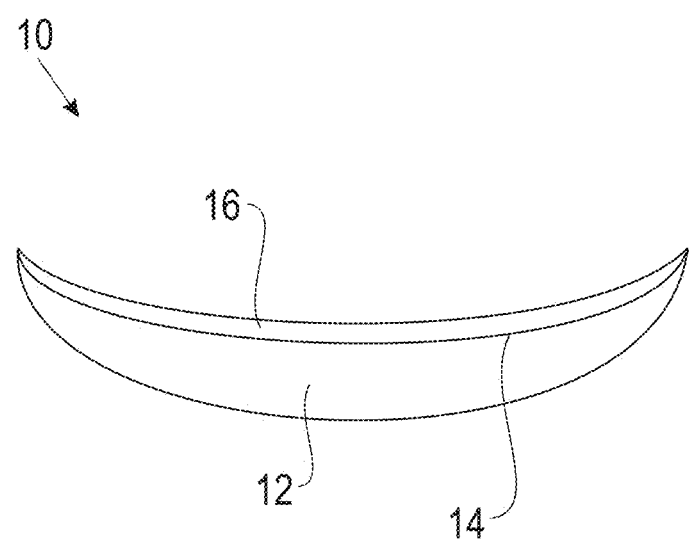
FIG. 1 is a cross-sectional layer diagram showing an antimicrobial film disposed on a surface of an object, such as a contact lens, having a curved surface.

Disclosed are methods for treating and/or inhibiting a bacterial infection using chemically modified polyethylenimines, referred to herein as cationic polyamines. Also disclosed are medical compositions (e.g., drugs) comprising the cationic polyamines. Further disclosed are antimicrobial films comprising the cationic polyamines. The cationic polyamines can be non-hemolytic at a concentration effective in killing a bacterium. In some instances, the cationic polyamines induce less than 20% hemolysis of red blood cells at 1000 mg/L (i.e., the cationic polyamine can have an HC20 value greater than 1000 mg/L), more specifically greater than 1500 mg/L, and even more specifically greater than 2000 mg/L. That is, the HC20 value for a given cationic polyamine can be well above the minimum inhibitory concentration (MIC) against a given microbe. The cationic polyamines can display high activity against Gram-negative microbes, Gram-positive microbes, yeast, and fungi. In particular, the cationic polyamines can be effective in killing a *mycobacterium* responsible for tuberculosis (TB).

Preferably, the cationic polyamines have a number average molecular weight (Mn) of about 100 to about 100,000, more particularly about 1000 to about 25,000, and most particularly about 1,000 to about 15,000.

The cationic polyamines comprise at least one polymer branch having a polymer backbone that comprises a plurality of repeat units referred to herein as ethylenimine units. Each of the ethylenimine units has 1 backbone nitrogen and 2 backbone carbons arranged as follows:

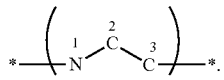

Herein, starred bonds represent attachment points. It should be understood that the nitrogen labeled 1 is trivalent and each carbon is tetravalent. Other substituents on the carbons and nitrogen are not shown in the above structure. The nitrogen labeled 1 represents the head of a given ethylenimine unit, and the carbon labeled 3 represents the tail of a given ethylenimine unit. Adjacent ethylenimine units are covalently linked head to tail (the starred bond of nitrogen 1 of a given ethylenimine unit is linked to carbon 3 of an adjacent ethylenimine unit).

The cationic polyamines can be effective antimicrobial agents without having a backbone nitrogen in the form of a quaternary ammonium salt. Herein, a quaternary ammonium salt comprises a positive-charged nitrogen that is covalently linked only to carbons (e.g., 4 carbons) and is non-covalently associated with a negative-charged counterion $X^\ominus$. The positive charged nitrogen of a quaternary ammonium salt is not covalently bound to any hydrogen. The disclosed cationic polyamines can contain no backbone nitrogens in the form of quaternary ammonium salt.

The cationic polyamines comprise one or more polymer chains (branches) comprising ethylenimine units. A linear cationic polyamine comprises i) one branch comprising a plurality of ethylenimine units and ii) two polymer chain end groups (also referred to as peripheral end groups). A branched cationic polyamine comprises two or more intersecting branches comprising ethylenimine units, and three or more peripheral polymer chain end groups.

Scheme 1 illustrates examples of the alternating arrangement of backbone carbon pairs and backbone nitrogens of the ethylenimine units of a linear cationic polyamine and of a branched cationic polyamine having two branches. The *—C—C—N—* unit enclosed in parentheses represents an ethylenimine unit. End groups, charges, counterions and substituents of the backbone carbons and nitrogens are not shown.

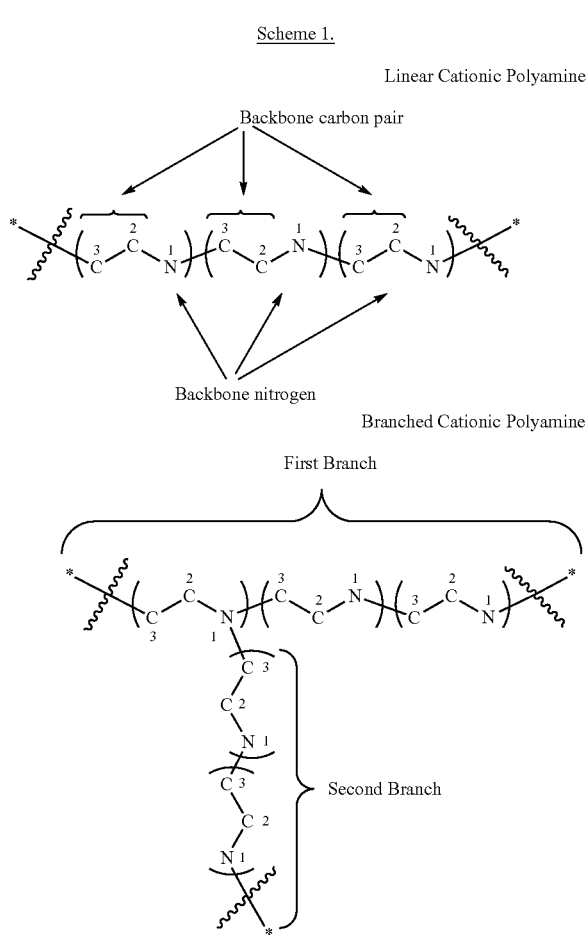

As shown above, adjacent *—C—C—N—* units are linked head to tail (i.e., nitrogen 1 of one ethylenimine unit is linked to carbon 3 of an adjacent ethylenimine unit).

Herein, a urea group is represented by the structure of formula (1):

$$
\begin{array}{c} \text{(1)} \\ R^1_{\phantom{1}N}^{\phantom{1}1} \overset{O}{\underset{}{\overset{\|}{C}}} \overset{2}{\underset{}{N}} R^2 \\ R^1 \phantom{xxxxx} R^2, \end{array}
$$

wherein each 10 is independently selected from the group consisting of hydrogen and groups comprising at least one alkylene carbon linked to nitrogen 1, and each $R^2$ is independently selected from the group consisting of hydrogen and groups comprising at least one alkylene carbon linked to nitrogen 2. Nitrogen 1 and/or nitrogen 2 can be members of a ring formed by R¹ and R¹, R¹ and R², or R² and R².

More specifically, the cationic polyamines have a polymer backbone comprising:

i) a protonated secondary ethylenimine unit (first ethylenimine unit) comprising a positive-charged backbone nitrogen linked to two hydrogens, having a structure according to formula (2):

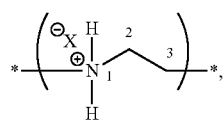
(2)

wherein $X^\ominus$ is a negative-charged counterion bound by non-covalent association with the positive charged nitrogen labeled 1, and ii) a non-charged N-acylated ethylenimine units (second ethylenimine unit) of formula (3):

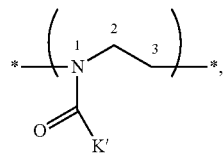
(3)

wherein each K' is an independent group comprising at least one carbon. Non-limiting examples of K' groups include $C_1$-$C_{10}$ alkyl groups, groups comprising a urea group, groups comprising a catechol group, and amine-containing groups that complete a urea group with the backbone nitrogen labeled 1. The cationic polyamine can comprise the K' groups singularly or in combination. In an embodiment, the cationic polyamine comprises the first ethylenimine unit and the second ethylenimine unit in a ratio of about 1:1 to about 400:1, respectively.

The first ethylenimine unit and the second ethylenimine unit are covalently linked. Herein, "covalently linked" means directly and/or indirectly covalently linked. "Directly covalently linked" means joined together by a single covalent bond. "Indirectly covalently linked" means covalently linked by way of a linking group. For example, a portion of the chemical structure of the cationic polyamine that contains one or more other ethylenimine units of the polymer backbone of the cationic polyamine can be a linking group, which covalently links the first ethylenimine unit to the second ethylenimine unit.

Hereinafter, $X^\ominus$ is a negative charged counterion unless otherwise indicated. Exemplary negative-charged counterions include halides (e.g., fluoride, chloride, bromide, iodide), nitrate, methane sulfonate, and carboxylates (e.g., acetate, benzoate). In an embodiment, $X^\ominus$ is chloride.

When K' comprises a urea group, the N-acylated ethylenimine unit has a structure according to formula (4):

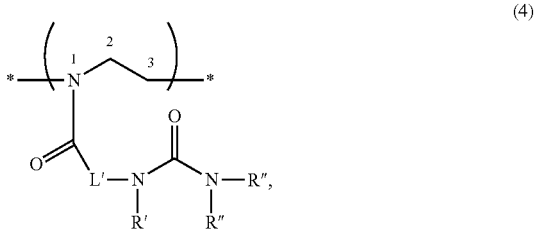
(4)

wherein L' is a divalent linking group comprising 1 to 30 carbons, R' is a monovalent radical selected from the group consisting of hydrogen, alkyl groups comprising 1 to 10 carbons, and aryl groups comprising 6 to 20 carbons, and each R" is a monovalent radical independently selected from the group consisting of hydrogen, alkyl groups comprising 1 to 20 carbons, and aryl groups comprising 6 to 20 carbons.

In an embodiment, R' is hydrogen, one R" is hydrogen, and another R" is phenyl.

In an embodiment L' has a structure according to formula (5):

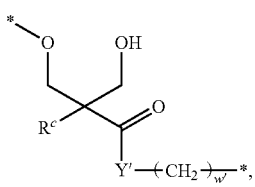
(5)

wherein the oxygen starred bond is linked a carbonyl group and the methylene starred bond is linked to a urea nitrogen, w' is a positive integer having of a value of 2 to about 20, Y' is *—O—* or *—N(H)—*, and $R^c$ is a monovalent alkyl group comprising 1 to 6 carbons.

In another embodiment, Y' is *—O—*.

More specifically, the urea-containing group *—C(=O)—K' of formula (3) can have a structure selected from the group consisting of:

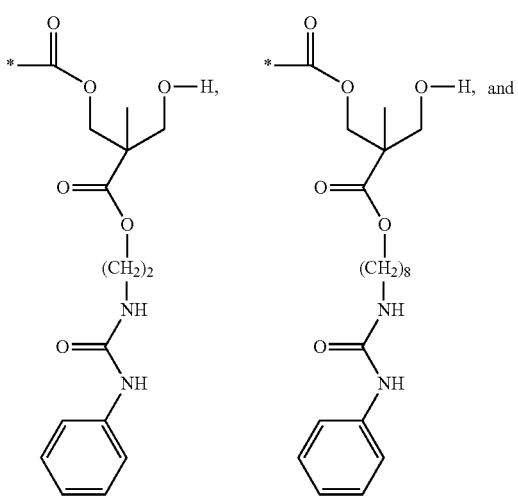

-continued

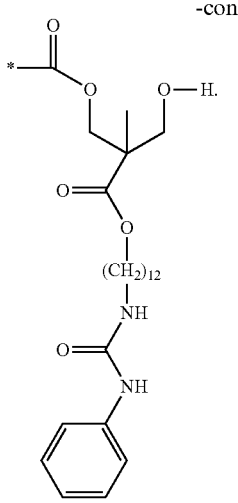

N-acylated ethylenimine units having a *—C(=O)—K' group that complete a urea group with the backbone nitrogen have a structure according to formula (6):

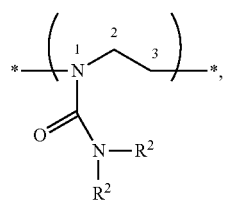

wherein each $R^2$ is a monovalent radical independently selected from the group consisting of hydrogen, alkyl groups comprising 1 to 30 carbons, and aryl groups comprising 6 to 30 carbons.

The cationic polyamines can further comprise one or more ethylenimine units selected from the group consisting of:
i) oxidized ethylenimine units (third ethylenimine units) of formula (7):

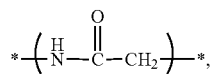

ii) protonated tertiary ethylenimine units (fourth ethylenimine units) comprising a positive-charged backbone nitrogen linked to one hydrogen, of formula (8):

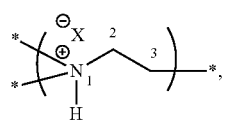

which serve as junction points for intersecting branches, and $X^\ominus$ is a negative-charged counterion bound by non-covalent association with the positive charged nitrogen labeled 1, and
iii) protonated primary ethylenimine units comprising a positive-charged backbone nitrogen linked to three hydrogens (fifth ethylenimine units), of formula (9):

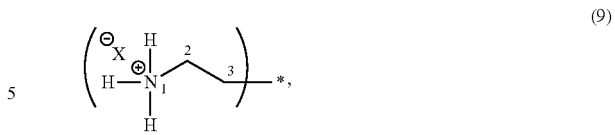

wherein $X^\ominus$ is a negative-charged counterion bound by non-covalent association with the positive charged nitrogen labeled 1.

Protonated primary ethylenimine units serve as branch terminating units. Herein, a hydrogen of the primary amine group of a primary ethylenimine unit can be a polymer chain end group. The cationic polymer can have other polymer chain end groups.

The cationic polyamines comprise at least one of the secondary ethylenimine units (first ethylenimine units) of formula (2) and at least one N-acylated ethylenimine unit (second ethylenimine units) of formula (3).

More specifically, the cationic polyamines can comprise about 100 to about 400 ethylenimine units, and still more specifically about 200 to about 300 ethylenimine units, wherein 1 to about 80 of the ethylenimine units are N-acylated ethylenimine units of formula (3), and all or substantially all of any remaining ethylenimine units comprise a positive charged protonated backbone nitrogen.

The end groups of the linear cationic polyamine can be any suitable end groups such as, for example, hydrogen, alkyl groups, amine groups, hydroxyalkyl groups, and combinations thereof.

In an embodiment, the linear cationic polyamine is a random copolymer comprising about 200 to about 300 ethylenimine units of formula (2), and 1 to about 30 N-acylated ethylenimine units of formula (3), wherein K' is a $C_1$-$C_{10}$ alkyl group. In another embodiment, the linear cationic polyamine comprises at least one oxidized ethylenimine unit of formula (7). In another embodiment, the linear cationic polyamine comprises 1 or more N-acylated ethylenimine units of formula (4) comprising a urea group. The nitrogen starred bond of the N-acylated ethylenimine units of formula (4) can be linked to another ethylenimine unit or an end group, which includes a hydrogen end group.

A branched cationic polyamine comprises 2 or more intersecting branches that together comprise 1 or more secondary ethylenimine units (first ethylenimine units) of formula (2), 1 or more N-acylated ethylenimine units (second ethylenimine units) of formula (3), 1 or more tertiary ethylenimine units (fourth ethylenimine units) of formula (8), and 1 or more primary ethylenimine units (fifth ethylenimine units) of formula (9).

More specifically, a branched cationic polyamine can comprise about 100 to 400 ethylenimine that include a plurality of secondary ethylenimine units of formula (2), at least one tertiary ethylenimine unit (fourth ethylenimine units) of formula (8), at least one primary ethylenimine unit (fifth ethylenimine unit) of formula (9), and at least one N-acylated ethylenimine unit of formula (4) that comprises a urea group. The nitrogen starred bond of the N-acylated ethylenimine units of formula (4) can be linked to another ethylenimine unit or to an end group, which includes a hydrogen end group.

Positive-charged backbone nitrogens of the cationic polyamine are present as ammonium salts of a protic acid (i.e., primary ammonium salt, secondary ammonium salt, or tertiary ammonium salt). A primary ammonium salt comprises a positive-charged nitrogen covalently linked to 1 carbon and 3 hydrogens, and non-covalently associated with a negative-charged counterion. A secondary ammonium salt comprises a positive-charged nitrogen covalently linked to 2 carbons and 2 hydrogens, and non-covalently associated with a negative-charged counterion. A tertiary ammonium salt comprises a positive-charged nitrogen covalently linked to 3 carbons and 1 hydrogen, and non-covalently associated with a negative-charged counterion.

Preparation of Linear Cationic Polyamines

The cationic polyamines can be prepared from a non-protonated polyethylenimine and/or a non-protonated partially N-acylated polyethylenimine. These base polyamines comprise a plurality of non-protonated ethylenimine units of formula (10):

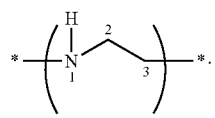

More particularly, linear cationic polyamines can be prepared from base polyamines that are partially or fully hydrolyzed poly(2-alkyloxazoline)s. Poly(2-alkyloxazoline)s can be prepared by cationic ring opening polymerization of 2-alkyl oxazolines (Scheme 2).

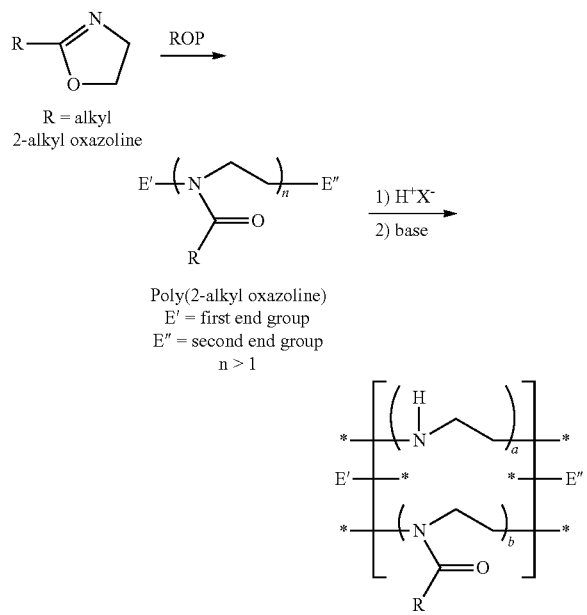

The ring opening polymerization (ROP) of the 2-alkyl oxazoline can be initiated by a cationic initiator $E'^+$, which becomes a first end group $E'$. $E''$ is a chain terminating second end group. R is typically a $C_1$-$C_{10}$ alkyl group. Partial hydrolysis of a poly(2-alkyl oxazoline) using a protic acid followed by neutralization of the hydrolyzed polymer yields a partially hydrolyzed non-protonated poly(2-alkyloxazoline) as shown in Scheme 2, where a+b=n, and a>0 and b>0. A fully hydrolyzed poly(2-alkyloxazoline) is a linear polyethylenimine (LPEI) homopolymer (a=n and b=0). The ethylenimine units of the partially or fully hydrolyzed poly(2-alkyloxazoline) are linked head to tail. In the above bracket notation of Scheme 2, the vertical stacking of the ethylenimine units within the square brackets indicates a random distribution of the ethylenimine units of the polymer chain. The examples further below demonstrate that a commercial non-protonated partially hydrolyzed poly(2-alkyloxazoline) is hemolytic and therefore not a suitable material for in vivo treatment of a bacterial infection, whereas the protonated partially hydrolyzed poly(2-alkyloxazoline) can be non-hemolytic and a highly active against a variety of microbes.

Thus, a first method of preparing an antimicrobial linear cationic polyamine comprises partially hydrolyzing a poly(2-alkyloxazoline) using a protic acid, thereby forming a water-soluble cationic polyamine, and isolating the cationic polyamine. Preferably, 50% to less than 100% of the N-acyl groups of the poly(2-alkyloxazoline) are hydrolyzed and have a structure of formula (2), and the remaining protonated ethylenimine units have a structure of formula (3).

Without being bound by theory, the linear base polyamine may undergo inter-chain aggregation and/or inter-chain coiling at high pH and/or during isolation of the solid form of the base polyamine. Inter-chain coiling may also be assisted by the drying conditions used for the base polymer. The inter-coiled linear polyamine chains may be more thermodynamically stable, more difficult to dissolve and/or protonate, and more prone to hemolysis. N-acyl groups and protonation of the backbone nitrogens may inhibit inter-chain coiling, resulting in non-associated cationic polymer chains having diminished hemolytic properties. The hemolytic properties may therefore be an indicator of the amount of inter-coiled polyamine chains present in solutions of the cationic polymer. Due to the difficulty in re-dissolving the base polyamine, partial hydrolysis of a poly(2-alkyloxazoline) and direct isolation and purification of the cationic polymer may be preferred.

A second method of preparing an antimicrobial linear cationic polyamine comprises dissolving the base form of a partially hydrolyzed poly(2-alkyloxazoline) (base polyamine) in an organic solvent (e.g., methanol), optionally at an elevated temperature, and treating the dissolved base polyamine with a protic acid, thereby forming an antimicrobial and non-hemolytic linear cationic polyamine.

Exemplary non-limiting protic acids include aqueous hydrochloric acid, carboxylic acids (e.g., acetic acid, benzoic acid), methane sulfonic acid, and the like.

A third method of preparing an antimicrobial linear cationic polyamine comprises forming a mixture comprising a base polyamine (e.g., partially or fully hydrolyzed poly(2-alkyloxazoline) and an organic solvent (e.g., chloroform) suitable for conducting an N-acylation. The mixture is optionally heated at an elevated temperature for a period of time sufficient to dissolve the base polyamine. The dissolved base polyamine is treated with one or more N-acylating agents, thereby forming a modified base polyamine comprising one or more of the above-described N-acylated ethylenimine units. Treating the modified base polyamine with a protic acid (e.g., aqueous HCl) forms a linear cationic polyamine.

Also disclosed is a method of introducing oxidized ethylenimine units into a linear base polyamine. A mixture comprising the linear base polyamine and an organic solvent is treated with air and/or a peroxide, thereby forming an oxidized linear base polyamine. This treatment can be performed at an elevated temperature before, during, and/or after dissolution of the linear base polyamine. Treatment of the oxidized linear base polyamine with a protic acid forms a cationic polyamine comprising oxidized ethylenimine units of formula (7):

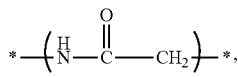
(7)

and
protonated secondary ethylenimine units of formula (2):

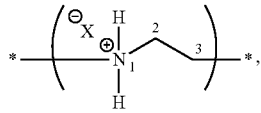
(2)

wherein $X^{\ominus}$ is a negative-charged counterion. The examples below illustrate that low levels of oxidation (<5% of the backbone nitrogens) can be effective in lowering hemolysis without significantly affecting antimicrobial activity of the oxidized cationic polyamine. The backbone amide groups introduced by oxidation can potentially also improve biocompatibility and/or biodegradability. The oxidized cationic polyamines can exhibit less than 20% hemolysis at 1000 mg/L (HC20>1000 mg/L).

Preparation of Branched Cationic Polyamines

The branched cationic polyamines are preferably prepared from a branched polyethylenimine (branched PEI or BPEI), which can be formed, for example, by ring opening polymerization of aziridine. The branched PEI has two or more intersecting polymer chains (branches) comprising backbone nitrogens in the form of primary amine nitrogens, secondary amine nitrogens, and tertiary amine nitrogens, which are alternatingly spaced by backbone ethylene groups (*—CH$_2$CH$_2$—*). The branched PEI comprises:

i) 1 or more non-protonated secondary ethylenimine units of formula (10):

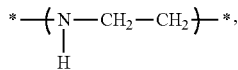
(10)

ii) 1 or more non-protonated tertiary ethylenimine units of formula (11):

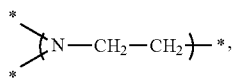
(11)

which serve as junction points for intersecting branches, and
iii) 2 or more non-protonated primary ethylenimine units of formula (12):

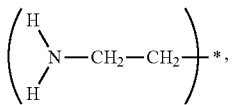
(12)

which serve as branch terminating end units.

A branched PEI is also represented herein by formula (13):

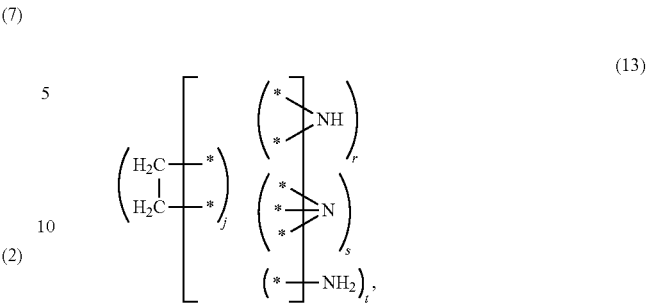
(13)

wherein j, r, s, and t represent average numbers of the respective independent functional groups of a BPEI macromolecule. Subscript j has an average value greater than or equal to 4, and r+s+t have an average value greater than or equal to 4. It should be understood by the notation of formula (13) that each set of parentheses ( ) beginning inside the square brackets [ ] and ending outside the square brackets encloses an independent functional group of the BPEI, not a polymer chain. Additionally, the atoms having starred bonds represent attachment points to the atoms having starred bonds on the opposite bracket. Additionally, the vertical stacking of the functional groups indicates a random distribution of the stacked functional groups in the branched PEI. Lastly, each starred bond of a given nitrogen on the right square bracket is linked to a different ethylene group on the left square bracket, and each starred bond of an ethylene group on the left square bracket is linked to a different nitrogen on the right square bracket, consistent with the head to tail arrangement of adjacent ethylenimine units.

In an embodiment, j has an average value of 180 to about 360, r has an average value of about 90 to about 140, s has an average value of about 45 to about 70, t has an average value of about 45 to about 70, and (r+s+t) has an average value of about 180 to about 360.

As an example, a commercially available branched polyethylenimine has a weight average molecular weight (Mw) of about 25,000, a number average molecular weight (Mn) of about 10,000, and contains an average of 233 ethylene groups (j), 116 backbone secondary nitrogens (r), 58 backbone tertiary nitrogens (s), and 58 primary amine nitrogens (t), based on Mn and an average ethylenimine unit molecular weight equal to 43. In this instance, j=233, r=116, s=58, and t=58. This material is referred to herein as BPEI25.

A branched cationic polyamine can be prepared by treating a base form of a branched PEI with an N-acylating agent capable of introducing one or more of the above-described N-acyl groups, thereby forming a modified branched PEI. Treatment of the modified branched PEI with a protic acid provides the branched cationic polyamine.

If desired, the branched PEI and/or the modified branched PEI can be oxidized as described above to introduce oxidized ethylenimine units of formula (7) for minimizing hemolysis and/or enhancing biodegradability. The oxidation can occur before, during, and/or after formation of the modified branched PEI.

End Groups

No restriction is placed on the cationic polyamine end groups with the proviso that the end group does not degrade the antimicrobial properties of the polymer.

A linear cationic polyamine comprises a first end group E' linked to a backbone nitrogen (labeled 1 above) of an ethylenimine unit. Exemplary first end groups include, hydrogen or $C_1$-$C_{10}$ alkyl or aryl. A linear cationic polyamine can comprise a second end group E' linked to a terminal carbon (labeled 3 above) of an ethylenimine unit. Exemplary second end groups include primary amine groups (*—$NH_2$), hydroxy groups (*—OH), and acylated derivatives thereof resulting from reaction with the N-acylating agents. The end groups of a branched cationic polyamine can consist essentially of primary ethylenimine units of formula (9) and acylated derivatives thereof. The linear and branched cationic polyamines can have other end groups.

Alkyl end groups are exemplified by the following chain terminating units of the cationic polyamine:
i) secondary ethylenimine units linked to an alkyl substituent $R^e$, having formula (14):

$$R^e \!\!-\!\!\left(\!\!\begin{array}{c} N-CH_2-CH_2 \\ | \\ H \end{array}\!\!\right)\!\!-\!\!*, \tag{14}$$

wherein $R^e$ is a $C_1$-$C_{10}$ alkyl or aryl group, and
ii) acylated ethylenimine units linked to an alkyl substituent $R^e$, having formula (15):

$$R^e \!\!-\!\!\left(\!\!\begin{array}{c} \phantom{O}-N-CH_2-CH_2 \\ \phantom{xx} \diagdown\phantom{x}| \\ \phantom{xxx} O \phantom{x} R^d \end{array}\!\!\right)\!\!-\!\!*, \tag{15}$$

wherein $R^e$ is a $C_1$-$C_{10}$ alkyl or aryl group, and $R^d$ is a $C_1$-$C_{10}$ alkyl group. In an embodiment, $R^e$ is methyl or ethyl.

Hydroxy end groups are exemplified by the following chain terminating units of linear PEI:
i) protonated secondary ethylenimine units linked to a hydroxy group:

$$*\!\!-\!\!\left(\!\!\begin{array}{c} H\phantom{x} X^\ominus \\ \oplus| \\ N-CH_2-CH_2 \\ | \\ H \end{array}\!\!\right)\!\!-\!\!OH,$$

and
ii) acylated ethylenimine units linked to a hydroxy group:

$$*\!\!-\!\!\left(\!\!\begin{array}{c} \phantom{O}-N-CH_2-CH_2 \\ \phantom{xx} \diagdown\phantom{x}| \\ \phantom{xxx} O \phantom{x} R^d \end{array}\!\!\right)\!\!-\!\!OH.$$

Amino end groups are exemplified by the following chain terminating units of linear PEI:
i) secondary ethylenimine units linked to a protonated primary amine group:

$$*\!\!-\!\!\left(\!\!\begin{array}{c} H\phantom{x} X^\ominus \\ \oplus| \\ N-CH_2-CH_2 \\ | \\ H \end{array}\!\!\right)\!\!-\!\!\overset{\oplus}{NH_3}\ X^\ominus,$$

and
ii) acylated ethylenimine units linked to a protonated primary amine group:

$$*\!\!-\!\!\left(\!\!\begin{array}{c} \phantom{O}-N-CH_2-CH_2 \\ \phantom{xx} \diagdown\phantom{x}| \\ \phantom{xxx} O \phantom{x} R^d \end{array}\!\!\right)\!\!-\!\!\overset{\oplus}{NH_3}\ X^\ominus.$$

Other end groups include alkoxy, thiol (*—SH), and substituted protonated secondary and tertiary amine groups. Other end groups include derivatives of any of the foregoing groups (e.g., esters and amides of hydroxy and amino end groups, respectively). The cationic polyamine can comprise the end groups singularly or in combination.

N-Acetylating Agents

Exemplary non-limiting N-acylating agents include carboxylic acid chlorides, carboxylic acid anhydrides, active esters, active carbonates, cyclic carbonates, isocyanates, and active carbamates.

Exemplary cyclic carbonate compounds include compounds of formula (B-1):

$$\text{(B-1)}$$

wherein
w' is a positive integer having of a value of 2 to about 20,
Y' is *—O—* or *—N(H)—*,
$R^c$ is a monovalent alkyl group comprising 1 to 6 carbons,
R' is a monovalent radical selected from the group consisting of hydrogen, alkyl groups comprising 1 to 30 carbons, and aryl groups comprising 6 to 30 carbons, and
each R" is a monovalent radical independently selected from the group consisting of hydrogen, alkyl groups comprising 1 to 20 carbons, and aryl groups comprising 6 to 20 carbons.

A primary or secondary nitrogen of the base polyamine can react with a compound of formula (B-1) by a ring opening reaction of the cyclic carbonate to form a modified base polyamine comprising a carbamate group that includes a urea group. The carbamate group of the modified base polyamine has a structure according to formula (B-2):

$$\text{(B-2)}$$

wherein
w' is a positive integer having of a value of 2 to about 20,
Y' is *—O—* or *—N(H)—*,
nitrogen labeled 1 is a nitrogen of the base PEI,
R$^c$ is a monovalent alkyl group comprising 1 to 6 carbons,
R' is a monovalent radical selected from the group consisting of hydrogen, alkyl groups comprising 1 to 30 carbons, and aryl groups comprising 6 to 30 carbons, and
each R" is a monovalent radical independently selected from the group consisting of hydrogen, alkyl groups comprising 1 to 20 carbons, and aryl groups comprising 6 to 20 carbons.

Non-limiting exemplary cyclic carbonate compounds of formula (B-1) include the compounds of Table 1:

TABLE 1

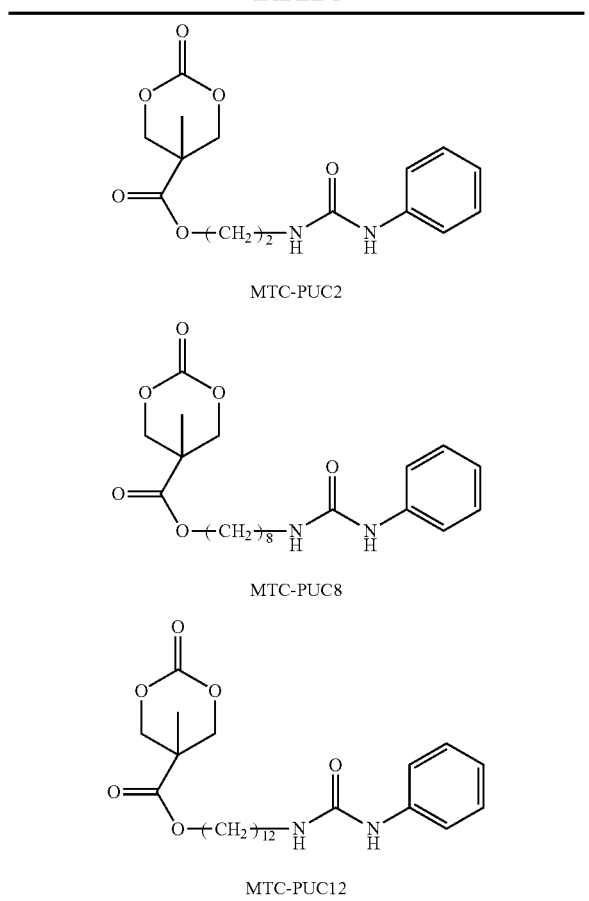

MTC-PUC2

MTC-PUC8

MTC-PUC12

Non-limiting isocyanates include phenyl isocyanate (C-1) and dodecyl isocyanate (C-2):

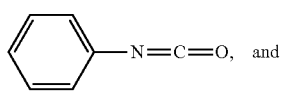
(C-1)

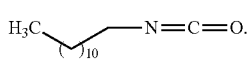
(C-2)

To illustrate, secondary ethylenimine units can react with phenyl isocyanate to form a urea-containing ethylenimine unit having the structure:

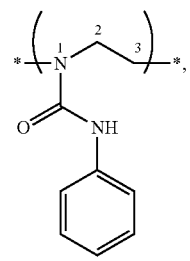

Many isocyanate compounds are commercially available for introducing a wide variety of urea groups having different nitrogen substituents.

Other N-acylating compounds include active carbamates such as, for example, 4-nitrophenyl-N-phenyl carbamate (C-3):

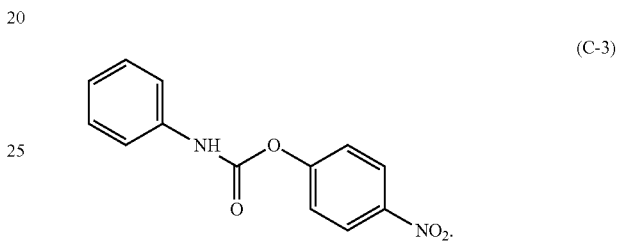
(C-3)

A primary and/or secondary backbone nitrogen can react with C-3 to form a urea group, releasing p-nitrophenol as a byproduct.

Film Formation

The cationic polyamines have utility in preparing articles comprising antimicrobial films disposed on surfaces of objects. The films can be effective in inhibiting growth of a biofilm and/or killing a bacterium (e.g., a fungus). Non-limiting objects include medical instruments (e.g., surgical tools, dental instruments, endoscopes), insertable medical devices (e.g., catheters, needles, stents, joint replacements, tooth implants, birth control devices, stomach tubing, ventilator tubing, hearing aids), bandages, garments, gloves, facial masks, hygiene products, beverage containers, food packaging materials, and contact lenses.

The object can comprise any suitable material. Non-limiting materials include inorganic and/or organic materials, more specifically metals, alloys, composites, woods, plastics, rubbers, glasses, yarns, fibers, cloths, and combinations thereof.

FIG. 1 is a cross-sectional diagram illustrating an article 10 comprising an antimicrobial film 16 disposed on a concave surface 14 of object 12, such as a contact lens. Article 10 is illustrative and not intended to depict relative scale.

The antimicrobial film comprises a cationic polyamine having a polymer backbone that comprises i) a positive-charged first ethylenimine unit of formula (2):

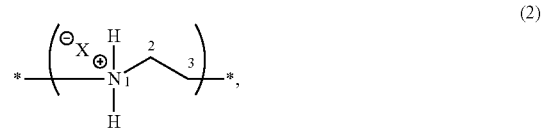
(2)

wherein X$^\ominus$ is a negative-charged counterion, and ii) a non-charged second ethylenimine unit of formula (3):

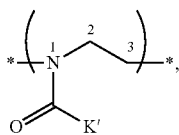
(3)

wherein K' comprises at least one carbon.

The antimicrobial film can be crosslinked or non-crosslinked A crosslinking film-forming composition can comprise a cationic polyamine, a crosslinking agent capable of reacting with the backbone nitrogens of the cationic polyamine to form a bridging group linking two or more cationic polyamine chains, and a solvent.

Exemplary non-limiting crosslinking agents include compounds selected from the group consisting of divinyl sulfones, bis-cyclic carbonates, dicarboxylic anhydrides, di-epoxides, di-isocyanates, and bis-active esters.

The film forming compositions can be applied to a surface of an object using any suitable coating technique (e.g., dip coating, spray coating, spin coating, roll coating, brush coating, and "ink jet" coating). Removing the solvent provides an antimicrobial film. The crosslinking chemistry of the film can be assisted or induced, for example, by heating the antimicrobial film at an elevated temperature for a suitable period of time. Other treatments for assisting or inducing crosslinking include chemical treatments and/or photochemical treatments using a suitable wavelength of radiation.

The cationic polyamines can comprise a catechol-containing moiety for enhancing adhesion of the film to an object surface. In this instance, the cationic polyamine can contain an ethylenimine unit of formula (D-1):

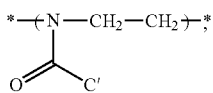
(D-1)

wherein C' is a moiety comprising a catechol group.

Exemplary C' groups include:

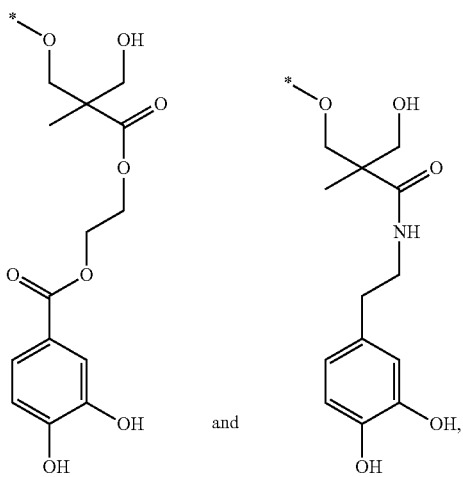 [SMILES: *OCC(C)(CO)C(=O)OCCOC(=O)c1ccc(O)c(O)c1 ; *OCC(C)(CO)C(=O)NCCc1ccc(O)c(O)c1]

the latter containing a dopamine residue.

N-acylating agents for introducing the above catechol moieties have the following structures, respectively:

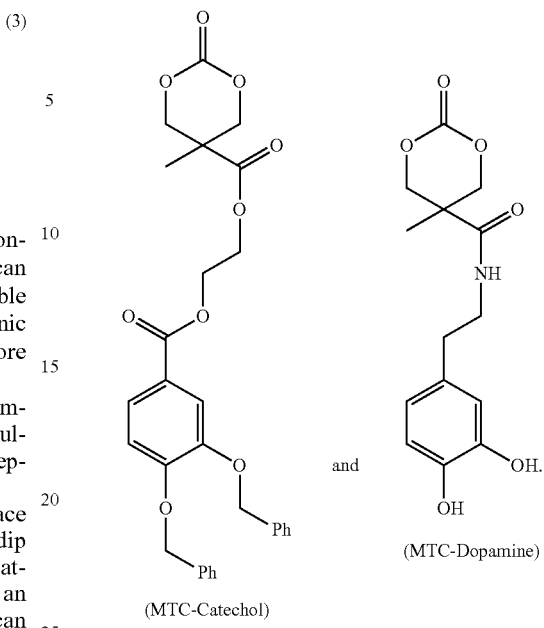

(MTC-Catechol) and (MTC-Dopamine)

The benzyl protecting groups of MTC-Catechol can be removed by reductive hydrogenation before or after chemical modification of the base polyamine. Acidification of the modified base polyamine provides a catechol-containing cationic polyamine.

The cationic polyamines can comprise one or more catechol-containing ethylenimine units. The resulting films can having strong adhesion properties and/or self-crosslinking properties, particularly on a poly(ethylene terephthalate) (PET) used in beverage containers and/or contact lens material.

Antimicrobial Properties

For the examples further below, the following definitions are applicable.

HC50 is defined as the concentration (in mg/L) of cationic polyamine that causes 50% of mammalian red blood cells to undergo hemolysis. HC50 values of 1000 mg/L or higher are desirable.

HC20 is defined as the concentration (in mg/L) of cationic polyamine that causes 20% of mammalian red blood cells to undergo hemolysis. HC20 values of 500 mg/L or higher are desirable.

Minimum inhibitory concentration (MIC) is defined as the minimum concentration (in mg/L) of cationic polyamine required to inhibit growth of a given microbe for an 18 hour period (bacteria) or 42 hour period (fungi). A MIC less than 500 mg/L is desirable. Even more desirable is a MIC of 150 mg/L or less. A lower MIC indicates higher antimicrobial activity.

Minimum bactericidal concentration (MBC) is defined as the minimum concentration (in mg/L) of cationic polyamine required to kill a given microbe. A lower MBC indicates higher antimicrobial activity.

HC50 selectivity is defined as the ratio of HC50/MIC. An HC50 selectivity of 3 or more is desirable. Higher HC50 selectivity values indicate more activity against bacterial cells and less toxicity to mammalian cells. Likewise, HC20 selectivity is defined as the ratio of HC20/MIC. An HC20 selectivity of 3 or more is desirable.

Non-limiting exemplary bacteria include Gram-positive *Staphylococcus aureus* (*S. aureus*), Gram-negative *Escheri*- chia coli (E. coli), fungus *Candida albicans* (*C. albicans*), Gram-negative *Pseudomonas aeruginosa* (*P. aeruginosa*), yeasts, and mycobacteria responsible for tuberculosis. Other microbes include Gram-positive *Staphylococcus epidermidis* (*S. epidermidis*), Gram-positive Methicillin-resistant *Staphylococcus aureus* (MRSA), Gram-positive Vancomycin-resistant *Enterococcus* (VRE), Gram-negative *Acinetobacter baumannii* (*A. baumannii*), and Gram-negative *Klebsiella pneumoniae* (*K. pneumoniae*) and *Cryptococcus neoformans* (*C. neoformans*).

The cationic polyamines can have a minimum inhibitory concentration (MIC) of about 7 mg/L to about 500 mg/L, and more preferably 7 mg/L to about 150 mg/L, and most preferably 7 mg/L to about 75 mg/L against a *mycobacterium*. In an embodiment, the cationic polyamines can have a MIC of about 7 mg/L to about 125 mg/L against *P. aeruginosa* and a tuberculosis *mycobacterium*.

The cationic polyamines can exhibit less than about 20% hemolysis at 1000 mg/L (i.e., can have an HC20 value greater than 1000 mg/L). More specifically, the cationic polyamines can exhibit less than about 20% hemolysis at 2000 mg/L. In some instances the cationic polyamines exhibit less than about 10% hemolysis at 2000 mg/L.

Further disclosed is a method comprising treating a medical condition caused by at least one bacterium by contacting the bacterium with any of the disclosed cationic polyamines, thereby killing the bacterium.

The low average mass, high antimicrobial activity, and low hemolytic tendencies of the cationic polyamines makes these materials attractive as broad spectrum antimicrobial agents for a wide range of medical and household uses, including wound treatments, treatment of infections, antibiotic drugs, treatment of tuberculosis, and disinfectants for household and hospital surfaces and medical instruments.

Also disclosed is a medical composition for treating wounds and/or infections, comprising one or more of the above-described cationic polyamines. The medical composition can be a drug. The drug can have the form of a solution, gel, powder, pill, paste, or ointment. The drug can comprise water. The drug can potentially be delivered orally, by injection, by spray, by inhalant, by dermal patch, and/or as a topically applied ointment.

The following examples demonstrate the preparation and properties of the cationic polyamines.

EXAMPLES

Materials used in the following examples are listed in Table 2.

TABLE 2

| ABBREVIATION | DESCRIPTION | SUPPLIER |
| --- | --- | --- |
| BPEI1.8 | Branched Polyethylenimine, Mw = 2000, Mn = 1800, 10 primary amine groups, 20 secondary amine groups and 10 tertiary amine groups | Sigma-Aldrich |
| BPEI25 | Branched Polyethylenimine, Mw = 25000, Mn = 10000, PDI 2.5, 58 primary amine groups, 116 secondary amine groups and 58 tertiary amine groups | Sigma-Aldrich |
| LPEI2.5 | Linear Polyethylenimine Mw = 2500 | Polysciences |
| LPEI25 | Linear Polyethylenimine Mw = 25000, Mn = 10950, PDI 1.16; 2 primary amine end groups, 246 secondary amine groups, 8 acylated amine groups. | Polysciences |
| LPEI250 | Linear Polyethylenimine Mw = 250000 | Polysciences |
| MTT | (3-(4,5-Dimethylthiazol-2-yl)-2,5-diphenyltetrazolium bromide | Sigma-Aldrich |
| IPMAN | 2,3;5,6-Di-O-Isopropylidene-D-Mannofuranose | Sigma-Aldrich |
|  | 2-Amino-1-Ethanol | Sigma-Aldrich |
|  | 8-Amino-1-Octanol | Sigma-Aldrich |
|  | 12-Amino-1-Dodecanol | Sigma-Aldrich |
| DBU | 1,8-Diazabicyclo[5,4,0]undec-7-ene | Sigma-Aldrich |
| TMC | Trimethylene Carbonate | Sigma-Aldrich |
| Bis-MPA | 2,2-Dimethylol-Propionic Acid | Sigma-Aldrich |
| PFC | Bis-pentafluorophenyl carbonate | Iris Biotech GmbH |

Herein, Mn is the number average molecular weight, Mw is the weight average molecular weight, and MW is the molecular weight of one molecule.

Gel permeation chromatography (GPC) analysis for LPEI2.5, LPEI25, and LPEI250 polymers was carried out using a Waters HPLC system equipped with a 2695 separation module with two ULTRAHYDROGEL 500 and 120 columns (size: 300×7.8 mm) in series and a Waters 2414 refractive index detector. The mobile phase used was 0.1 M citric acid aqueous solution with pH 2.74 at a flow rate of 0.5 mL/min. Number-average molecular weights as well as polydispersity indices were calculated from a calibration curve using a series of poly(ethylene glycol) standards with molecular weights ranging from 633 to 20,600.

Bis-pentafluorophenyl carbonate (PFC) was purchased from Iris Biotech GmbH (Marktredwitz, Germany) and purified by crystallizing twice from a mixture of ethyl acetate and hexanes.

Solid branched polyethylenimine (BPEI25, Mn 10,000, PDI 2.5) was freeze-dried prior to use.

LIVE/DEAD Baclight bacterial viability kits (L-7012) were bought from Invitrogen.

N-bis(3,5-trifluoromethyl)phenyl-N'-cyclohexyl-thiourea (TU) has the following structure:

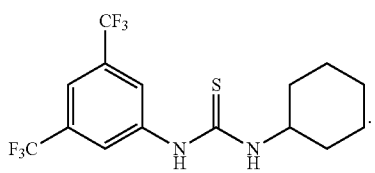
(TU)

TU was prepared as reported by the method of R. C. Pratt, B. G. G. Lohmeijer, D. A. Long, P. N. P. Lundberg, A. Dove, H. Li, C. G. Wade, R. M. Waymouth, and J. L. Hedrick, Macromolecules, 2006, 39 (23), 7863-7871, and dried by stirring in dry THF over CaH$_2$, filtering, and removing solvent under vacuum.

MTC-C6F5 (MW 326.2) has the structure:

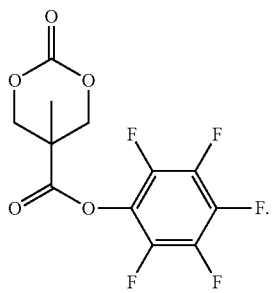

MTC-C6F5 was obtained from Central Glass and purified by crystallizing twice from a mixture of ethyl acetate and hexanes.

Anhydrous solvents were dried using activated alumina columns and stored over molecular sieves (3 Å). DBU was stirred over CaH$_2$ and vacuum distilled before being transferred to a glove box.

$^1$H NMR spectra were acquired on a Bruker Avance 400 instrument at 400 MHz. Gel permeation chromatography (GPC) was performed in tetrahydrofuran (THF) using a Waters system equipped with four 5-micrometer Waters columns (300 mm×7.7 mm) connected in series with increasing pore size (100, 1000, 105, and 106 angstroms), a Waters 410 differential refractometer, and a 996 photodiode array detector. The system was calibrated using polystyrene standards. GPC analysis was also performed in N,N-dimethylformamide (DMF) spiked with 0.01 M LiBr using a Waters system equipped with two Agilent PolyPore columns (300 mm×7.5 mm) connected in series, a Waters 410 differential refractometer. The system was calibrated with poly(methyl methacrylate) standards.

PREPARATIONS

MTC-OBn (shown below) and other cyclic carbonate monomers can be prepared from 2,2-bis(methylol)propionic acid (bis-MPA) using the route shown in Scheme 1.

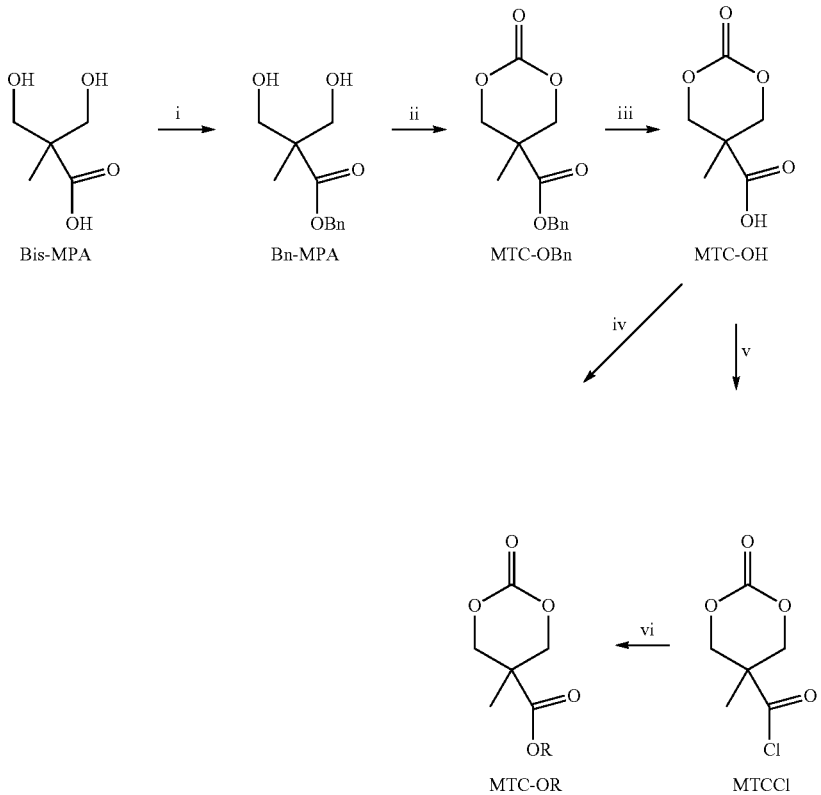

Scheme I.

2,2-Bis(methylol)propionic acid (bis-MPA) is first converted (i) to a benzyl ester Bn-MPA, followed by reaction (ii) of Bn-MPA with triphosgene to form a cyclic carbonyl monomer, MTC-OBn. MTC-OBn is debenzylated (iii) to produce the cyclic carbonyl carboxylic acid, MTC-OH. Two pathways are shown for forming an ester from MTC-OH. In the first pathway, (iv), MTC-OH is treated with a suitable carboxy activating agent, such as dicyclohexylcarbodiimide (DCC), which reacts with ROH to form MTC-OR in a single step. Alternatively, MTC-OH can be converted first (v) to the acid chloride MTCCl followed by treatment (vi) of MTCCl with ROH in the presence of a base to form MTC-OR. Both pathways are illustrative and are not meant to be limiting. The following conditions are typical for the reactions shown in Scheme 1: (i) Benzylbromide (BnBr), KOH, DMF, 100° C., 15 hours, 62% yield of the benzyl ester of bis-MPA; (ii) triphosgene, pyridine, $CH_2Cl_2$, −78° C. to 0° C., 95% yield of MTC-OBn; (iii) Pd/C (10%), H2 (3 atm), EtOAc, room temperature, 24 hours, 99% yield of MTC-OH; (iv) ROH, DCC, THF, room temperature, 1 to 24 hours; (v) $(COCl)_2$, THF, room temperature, 1 hour, 99% yield of MTCCl; (vi) ROH, $NEt_3$, RT, 3 hours yields MTC-OR.

Preparation of MTC-BnCl (MW 298.7)

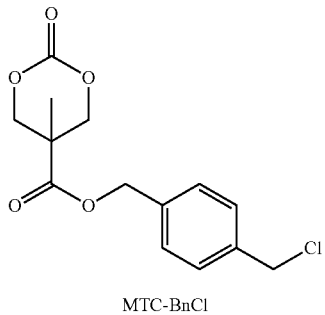

MTC-BnCl

A flask was charged with MTC-C6F5 (10 g, 30.6 mmol), p-chloromethyl benzyl alcohol (4.8 g, 30.6 mmol), PROTON SPONGE (2 g, 9.3 mmol) and THF (30 mL) The reaction mixture was stirred for 12 hours then added directly to a silica gel column. The product was isolated using diethyl ether as the eluent to yield 7.45 g (81%) white crystalline powder. $^1$H NMR (400 MHz, $CDCl_3$, 22° C.): delta 7.40 (dd, 4H, $C_6H_4$), 5.24 (s, 2H, —$OCH_2C_6H_4$), 4.73 (d, 2H, —$CH_2OCOO$), 4.60 (s, 2H, —$CH_2Cl$), 4.22 (d, 2H, —$CH_2OCOO$), 1.35 (s, 3H, —$CH_3$).

Preparation of Chol-OPrOH (MW 444.7)

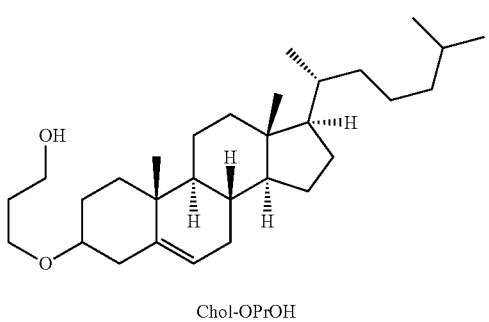

Chol-OPrOH

1) Preparation of Chol-OMes Intermediate (MW 464.7)

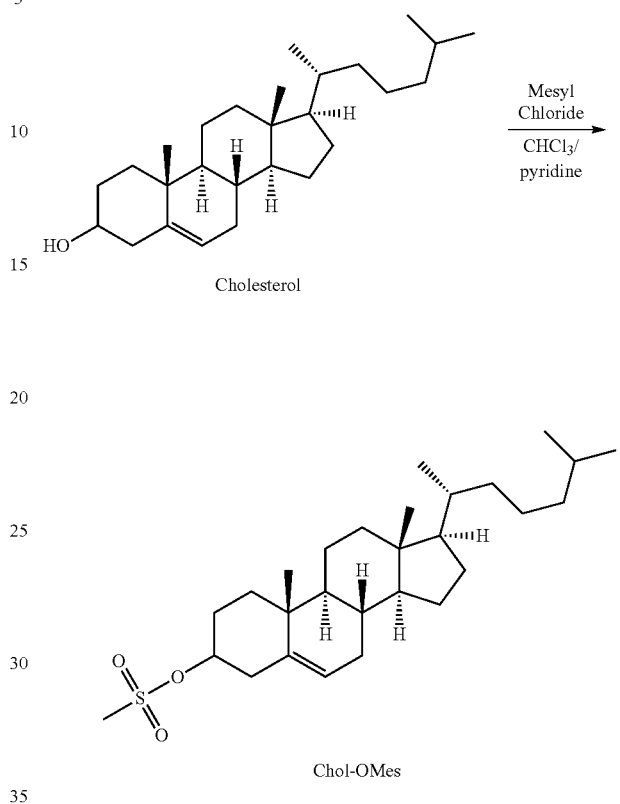

Cholesterol (10 g, 25.8 mmol, MW 386.35) was dissolved in dry chloroform ($CHCl_3$) (15 mL) and pyridine (15 mL) The reaction mixture was then purged with nitrogen and rapidly stirred. Mesyl chloride (3 mL, 38.8 mmol) was then added drop wise. The reaction mixture was stirred for 4 hours at ambient temperature followed by precipitation into MeOH (600 mL) The filtrate was collected via vacuum filtration to yield 9.6 g (80%) of a white powder.

2) Chol-OMes (1 g, 2.15 mmol) was suspended in 1,4-dioxane (10 mL) and 1,3-propanediol (4 g, 53.8 mmol). The reaction mixture was degassed, purged with nitrogen and heated to 110° C. After 1 hour the reaction mixture was allowed to cool to ambient temperature and precipitated into MeOH/$H_2O$ (4:1). The product Chol-OPrOH was further purified using column chromatography producing 0.72 g (75%) of a waxy off-white material.

Cyclic carbonates having a pendant phenylurea group were prepared according to Scheme 2.

Scheme 2.

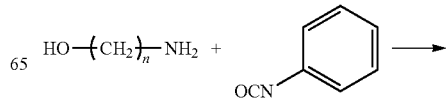

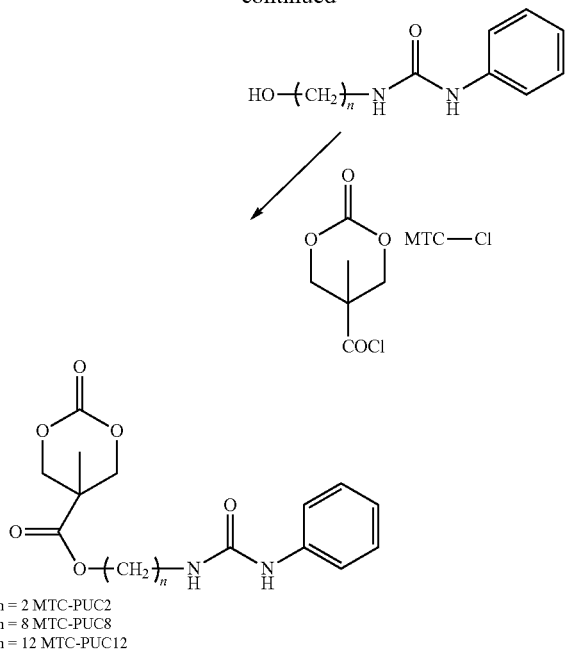

n = 2 MTC-PUC2
n = 8 MTC-PUC8
n = 12 MTC-PUC12

Preparation of MTC-PUC2 (MW 322.3)

This preparation is representative and was performed in two parts.

1) Ethanolamine (5.0 g, 48.5 mmol, 1 eq) was placed in a dry 100 mL round bottom flask equipped with a stir bar, and dry THF (30 mL) was added. The resulting solution was chilled to 0° C. using an ice bath. Phenylisocyanate (5.19 g, 4.74 mL, 43.6 mmol, 0.9 equivalents) and 30 mL of dry THF was added dropwise to the ethanolamine/THF mixture through a dropping funnel over 30 min. The resulting mixture was left to warm to ambient temperature and allowed to stand under stirring for an additional 16 hours. Rotational evaporation was used to remove THF. The resulting crude product was recrystallized from ethyl acetate before being stirred vigorously for an additional 4 hours. The recrystallized solids were isolated by filtration and further washed with ethyl acetate and dried until a constant weight was reached, giving a yield of 7.0 g (~80%) intermediate phenylureaethanol (n=2 in Scheme 2). $^1$H-NMR (400 MHz, DMSO-d$_6$, 22° C.): delta 8.55 (s, 1H, —NHPh), 7.36 (d, 2H, PhH), 7.20 (t, 2H, PhH), 6.88 (t, 1H, PhH), 6.18 (t, 1H, —CH$_2$NHCO—), 4.76 (t, 1H, —OH), 3.43 (q, 2H, —CH$_2$OH), 3.15 (q, 2H, —CH$_2$NHCO—).

2) MTC-OH (4.3 g, 26.8 mmol) was converted to MTC-Cl by using oxalyl chloride as described above. The MTC-Cl was dissolved in 50 mL of dry methylene chloride and charged in an additional funnel. In a dry 500 mL round bottom flask equipped with a stir bar was charged phenylureaethanol (5.55 g, 25 mmol), pyridine (1.97 g, 2.02 mL, 25 mmol) and dry methylene chloride (150 mL) The additional funnel was attached under nitrogen and the flask cooled to 0° C. using an ice bath. The MTC-Cl solution was added dropwise during a period of 30 minutes and the resulting solution was stirred an additional 30 minutes. The ice bath was removed and the solution was allowed to warm up to ambient temperature and left under stirring for an additional 16 hours. The crude product was purified by column chromatography using silica gel. Methylene chloride was initially used as eluent before gradually increasing the polarity finishing with a final concentration of 5 vol % methanol. The product fractions were collected and the solvent was removed through rotational evaporation. The isolated product was dried under vacuum until a constant weight was reached yielding 8.0 g (about 80%) of an off-white/yellowish oil which crystallized upon standing. $^1$H-NMR (400 MHz, DMSO-d$_6$, 22° C.): delta 8.59 (s, 1H, —NHPh), 7.38 (d, 2H, PhH), 7.21 (t, 2H, PhH), 6.89 (t, 1H, PhH), 6.26 (t, 1H, —CH$_2$NHCO—), 4.57 (d, 2H, —COOCH$_2$CH$_2$—), 4.35 (d, 2H, —CH$_2$OCOO—), 4.16, (t, 2H, —CH$_2$OCOO—), 3.35 (q, 2H, —CH$_2$NHCO—), 1.20 (s, 3H, —CH$_3$).

Preparation of MTC-PUC8

MTC-PUC8 (MW 406.5) was prepared according to the procedure for preparing MTC-PUC2 using 8-amino-1-octanol. Yield, 86%, $^1$H-NMR (400 MHz, DMSO-d$_6$, 22° C.): delta 8.37 (s, 1H, —NHPh), 7.38 (d, 2H, PhH), 7.21 (t, 2H, PhH), 6.86 (t, 1H, PhH), 6.10 (t, 1H, —CH$_2$NHCO—), 4.57 (d, 2H, —COOCH$_2$CH$_2$—), 4.39 (d, 2H, —CH$_2$OCOO—), 4.17, (t, 2H, —CH$_2$OCOO—), 3.06 (q, 2H, —CH$_2$NHCO—), 1.26-1.40 (2 s, 15H, —(CH$_2$)$_6$— and —CH$_3$).

Preparation of MTC-PUC12

MTC-PUC12 (MW 462.6) was prepared according to the procedure for MTC-PUC2 using 12-amino-1-dodecanol. Yield, 65%, $^1$H-NMR (400 MHz, DMSO-d$_6$, 22° C.): delta 8.37 (s, 1H, —NHPh), 7.34 (d, 2H, PhH), 7.17 (t, 2H, PhH), 6.83 (t, 1H, PhH), 6.09 (t, 1H, —CH$_2$NHCO—), 4.51 (d, 2H, —COOCH$_2$CH$_2$—), 4.33 (d, 2H, —CH$_2$OCOO—), 4.09, (t, 2H, —CH$_2$OCOO—), 3.02 (q, 2H, —CH$_2$NHCO—), 1.28-1.56 (m, 23H, —(CH$_2$)$_{10}$— and —CH$_3$).

Preparation of 3,4-bis(benzyloxy)benzoic acid 3,4-Dihydroxy benzoic acid, benzyl bromide, and potassium carbonate were dissolved in acetonitrile, and the solution was refluxed for 18 hours. The reaction solution was then cooled to room temperature and filtered. The solution was then concentrated and diluted with hexanes, resulting in a solid that was collected by filtration. The solid was then recrystallized in the mixture of THF and hexanes, giving rise to a pure product.

Preparation of 2-hydroxyethyl 3,4-bis(benzyloxy)benzoate 3,4-Bis(benzyloxy)benzoic acid was dispersed in ethylene glycol, and heated to 80° C. A catalytic amount of KOH was added to the solution that was left to react until all solids were dissolved. The solution was precipitated into cold water and left to stir for several hours, yielding a white solid. The solid was obtained by filtration, rinsed with water, and then freeze dried.

Preparation of MTC-Catechol

2-Hydroxyethyl-3,4-bis(benzyloxy)benzoate 2.81 g, 7.42 mmol), MTC-C6F5 (2.54 g, 7.79 mmol) and PROTON SPONGE (1.59 g, 7.42 mmol) were dissolved in THF (10 mL) and stirred overnight at room temperature. Once the reaction was completed, a mixture of diethyl ether and hexanes was added, and the solution was left for several hours at −40° C. White crystals were obtained and washed with diethyl ether and hexanes.

Preparation of MTC-dopamine

MTC-OH (1.024 g, 6.4 mmol), dicyclohexylcarbodiimide (DCC, 1.319 g, 6.4 mmol) and N-hydroxysuccinimide (NHS, 0.736 g, 6.4 mmol) were charged in a 100 mL round bottom flask and dissolved in 8 mL of dry DMF before put in a ice bath. Dopamine.HCl (1.092 g, 5.76 mmol) and $Et_3N$ (1.685 mL, 12.1 mmol) was dissolved in 8 mL of dry DMF and added dropwise to the above solution under N2 atmosphere. The ice bath was removed after 3 hours and the reaction continued overnight. Then, the reaction solution was precipitated in DCM and a mixture of THF and $Et_2O$ (v/v=1:1) sequentially. Finally, the filtrate was concentrated, precipitated in $Et_2O$ and washed with $Et_2O$ for three times to give MTC-dopamine.

Preparation of MTC-PEG750

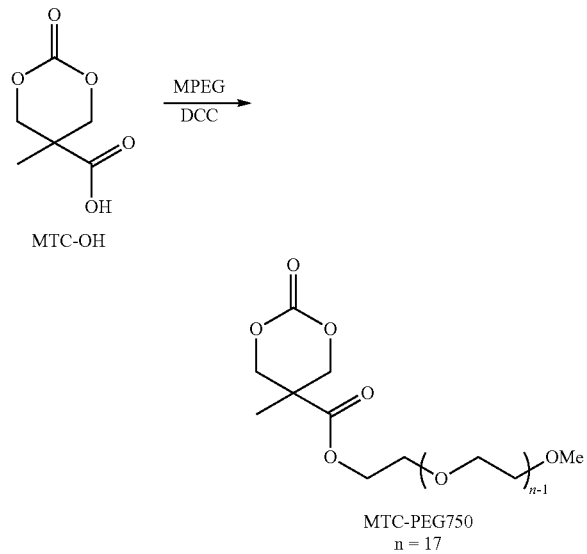

Oligomeric monomethoxy poly(ethylene glycol) (MPEG750, 4.5 g, Mn=750, PDI 1.03, 6 mmol) was charged in a 250 mL three-neck round bottom flask and heated to 82° C. in vacuo with stirring overnight and cooled to room temperature. A solution of MTC-OH (1.44 g, 9 mmol) in dry THF (50 mL) was added to the MPEG under nitrogen atmosphere, followed by gently adding a solution of dicyclohexylcarbodiimide (DCC) (2.48 g, 12 mmol) in dry THF (50 mL) The reaction solution was stirred for 48 hours, filtered, and concentrated to dryness. The resulting crude product was purified by column chromatography on a SEPHADEX LH-20 column with THF as eluent, giving pure MTC-PEG as a white viscous solid (4.6 g, 83%). $^1$H NMR (400 MHz, $CDCl_3$, 22° C.): delta 4.45 (dd, 4H, —$CH_2OCOO$—), 4.35 (d, 2H, —$COOCH_2$-MPEG), 3.65 (s, 68H, H of MPEG), 1.34 (s, 3H, —$CH_3$).

Preparation of MTC-PEG5k

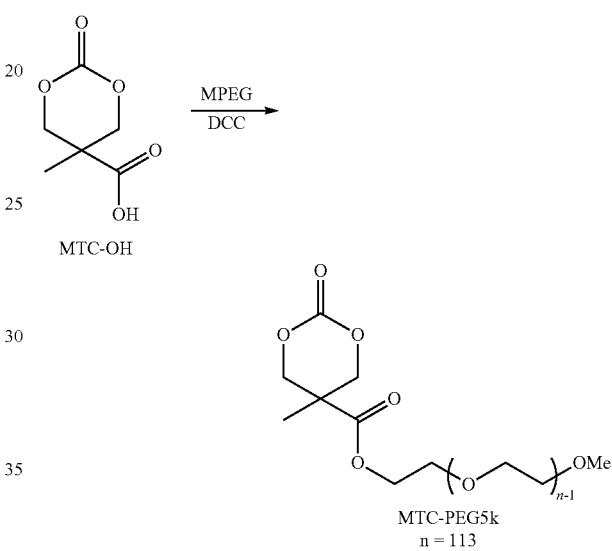

MTC-PEG5k was prepared using the general procedure described above for MTC-PEG750, substituting MPEG750 with MPEG5k (Mn=5000).

Polymer Samples

Example 1

Sample L1 is LPEI2.5 (LPEI, Mn 7460) and was used as purchased. GPC analysis of this sample showed the following: Mw=9750, Mn=7460, 173 secondary amine groups.

Example 2

Sample L2 is LPEI25 (LPEI, Mn 10950) and was used as purchased. GPC analysis of this sample showed the following: Mw=12730, Mn=10950, 255 secondary amine groups.

Example 3

Sample L3 is LPEI250 (LPEI, Mn 11880) and was used as purchased. GPC analysis of this sample showed the following: Mw=13340, Mn=11880, 276 secondary amine groups.

Example 4

Preparation of L4. LPEI2.5 (0.3 g, 0.04 mmol) was dissolved in dioxane (30 mL) and heated to 80° C. for 16 hours while exposed to air. The solution was cooled to room temperature before dioxane was removed by rotary evaporator. The residue was dissolved in 10 mL of MeOH and acidified by adding 10 mL of aqueous HCl solution (1 M).

Example 5

Preparation of sample L5. The procedure of Example 4 was followed using LPEI25 (0.3 g, 0.027 mmol) and dioxane (30 mL) while exposed to air. The solution was cooled to room temperature before dioxane was removed by rotary evaporator. The residue was dissolved in 10 mL of MeOH and acidified by adding 10 mL of aqueous HCl solution (1 M). A proton NMR of the sample indicated approximately 30% oxidation of the PEI nitrogen, forming a backbone amide.

Example 6

Preparation of L6. The procedure of Example 4 was followed using LPEI250 (0.3 g, 0.025 mmol) and dioxane (30 mL) while exposed to air. The solution was cooled to room temperature before dioxane was removed by rotary evaporation. The residue was dissolved in 10 mL of MeOH and acidified by adding 10 mL of aqueous HCl solution (1 M).

Example 7

Preparation of L7. LPEI25 (0.3 g, 0.027 mmol) was dried in vacuum at 65° C. for 2-3 hours, then cooled to room temperature and combined with chloroform (30 mL). The mixture was heated at 85° C. with stirring while exposed to air, achieving homogenous solution in about 1-2 hours. Heating was continued overnight. The solution was then cooled to room temperature, the solvent was removed under vacuum, and the residue was dissolved in MeOH (10 mL) followed by addition of 1 M HCl (10 mL) The solution was stirred for 2-3 hours and concentrated to dryness. The residue was dissolved in a small volume of water, and the resulting solution transferred to a 20-mL vial. The solution was freeze-dried to yield a yellowish powder. No evidence of oxidation of the PEI was found.

Example 8

Preparation of L8. LPEI25 (0.3 g, 0.027 mmol) was dried in vacuum at 65° C. for overnight, then cooled to room temperature. The sticky solid was dissolved in MeOH (10 mL) at 22° C. for 5 minutes followed by addition of 1 M HCl (10 mL) while exposed to air. The solution was stirred for 2-3 hours and concentrated to dryness. The residue was dissolved in a small volume of water, and the resulting solution transferred to a 20-mL vial. The solution was freeze-dried to yield a white powder. No evidence of oxidation of the PEI was found.

Example 9

Preparation of L9. The procedure of Example 7 was followed using LPEI25 (0.3 g, 0.027 mmol) and tetrahydrofuran (THF, 30 mL) A homogenous solution was achieved after 1-2 hours when heated in THF. The freeze-dried solution yielded a white powder. No evidence of oxidation of the PEI was found.

Example 10

Preparation of L10. LPEI25 (0.3 g, 0.027 mmol) was dried overnight in vacuum at 65° C., cooled to room temperature, then heated overnight in open air at 85° C. The solid was dissolved in MeOH (10 mL) at 22° C. for 5 minutes followed by addition of 1 M HCl (10 mL) The solution was stirred for 2-3 hours and concentrated to dryness. The residue was dissolved in a small volume of water, and the resulting solution transferred to a 20-mL vial. The solution was freeze-dried to yield a brown powder. FT-IR and proton NMR of the sample indicated approximately 30% oxidation of the PEI nitrogen, forming a backbone amide.

Example 11

Preparation of L11. The procedure of Example 7 was followed using LPEI25 (0.3 g, 0.027 mmol), heating the LPEI25 in acetonitrile (ACN, 30 mL) at 80° C. for 16 hours. A homogenous solution was achieved overnight when heated in ACN. The freeze-dried solution yielded a yellowish powder. No evidence of oxidation of the PEI was found.

Example 12

Preparation of L12. LPEI25 (0.3 g, 0.027 mmol) was heated in a vacuum at 65° C. for 2-3 hours. The sticky solid was dissolved in 10 mL of MeOH at 22° C. for 5 minutes, followed by adding 10 mL of 1 M HCl. The solution was stirred for 2-3 hours before being concentrated to dryness. The residue was dissolved in a small volume of water and transferred to a 20-mL vial. The solution was freeze-dried to yield a white powder. No evidence of oxidation of the PEI was found.

Example 13

Preparation of L13. The procedure of Example 7 was followed using LPEI25 (0.3 g, 0.027 mmol), heating LPEI25 in ethyl acetate (30 mL) at 85° C. for 16 hours. A homogenous solution was achieved overnight when heated in ethyl acetate. The freeze-dried solution yielded a yellow powder. No evidence of oxidation of the PEI was found.

Example 14

Preparation of L14. LPEI25 (0.3 g, 0.027 mmol) was added to MeOH (10 mL) at 22° C. for 5 minutes followed by addition of 1 M HCl (10 mL). The solution was stirred for 2-3 hours and concentrated to dryness. The residue was dissolved in a small volume of water, and the resulting solution transferred to a 20-mL vial. The solution was freeze-dried to yield a white powder. No evidence of oxidation of the PEI was found.

Example 15

Preparation of L15. The procedure of Example 7 was followed using LPEI25 (0.3 g, 0.027 mmol), heating the LPEI25 in methanol (30 mL) at 85° C. for 16 hours. The freeze-dried solution yielded a yellowish powder. No evidence of oxidation of the PEI was found.

Example 16

Preparation of L16. The procedure of Example 7 was followed using LPEI25 (0.3 g, 0.027 mmol), heating the LPEI in dioxane (30 mL) at 85° C. for 16 hours. The freeze-dried solution yielded a brown powder. FT-IR and proton NMR of the sample indicated approximately 30% oxidation of the PEI nitrogen, forming a backbone amide.

Example 17

Purification of L14 to form L17. Sample L14 (Example 14, 50 mg) was dissolved in deionized water (DI water, 5 mL) The resulting solution (pH 1.9) was transferred to a 15-ml centrifugal concentrator having a molecular weight cutoff (MWCO) of 3,000, and washed with DI-water 3 times prior to lyophilization, yielding a white powder.

Example 18

Neutralization of L14 to form L18. Sample L14 (Example 14, 50 mg) was dissolved in deionized water (DI water, 5 mL) and adjusted to pH 7.2 with 0.1M NaOH solution. The mixture was transferred to a 15-ml centrifugal concentrator (MWCO=3,000) and washed with DI-water for 3 times prior to lyophilization, yielding a white powder.

Example 19

Purification of L15 to form L19. Sample L15 (Example 15, 50 mg) was dissolved in deionized water (DI water, 5 mL) The resulting solution (pH 1.9) was transferred to a 15-ml centrifugal concentrator (MWCO=3,000) and washed with DI-water 3 times prior to lyophilization, yielding a white powder.

Example 20

Neutralization of L15 to produce L20. Sample L15 (Example 15, 50 mg) was dissolved in deionized water (DI water, 5 mL) and adjusted to pH 7.2 with 0.1M NaOH solution. The mixture was transferred to a 15-ml centrifugal concentrator (MWCO=3,000) and washed with DI-water for 3 times prior to lyophilization, yielding a white powder.

In the following examples the structure of LPEI25 is represented by the structure:

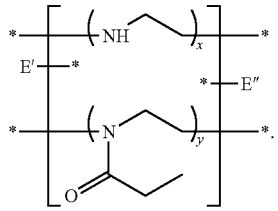

LPEI25
$x = 247$
$y = 8$
$E' = *\text{---}CH_2CH_2NH_2$
$E'' = *\text{---}NH_2$

The quantity x represents the number of secondary amine groups in LPEI25, and x=247. The subscript y represents the number of residual non-hydrolyzed secondary amine sites in the as-purchased LPEI25. The LPEI can be fully hydrolyzed (i.e., y=0). However, in the present examples, y is 8 (calculated from the proton NMR spectrum). The first end group E' of the as-purchase LPEI25 is a primary ethylenimine group. The second end group E" is $*\text{---}NH_2$. That is, the as-purchased LPEI25 contained two primary amine groups per chain. The stacking of the subunits in the square brackets indicates a random distribution of the subunits. The subunits are linked head to tail (nitrogen to carbon). That is, each starred bond from a nitrogen of a given subunit is linked to a carbon of an ethylene group of a different subunit or to a chain end group E', and each starred bond from a methylene carbon of a given subunit is linked to a nitrogen of a different subunit or to an end group E".

Example 21

Preparation of L21, by reaction of LPEI25 with MTC-PUC12 (z=10).

LPEI25 +
$x = 247$
$y = 8$

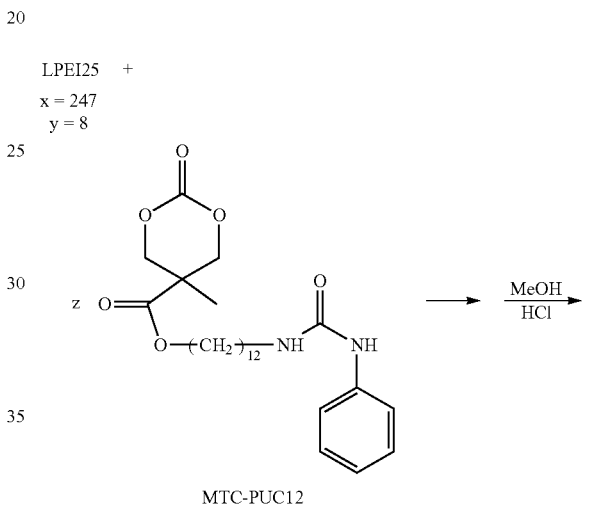

MTC-PUC12

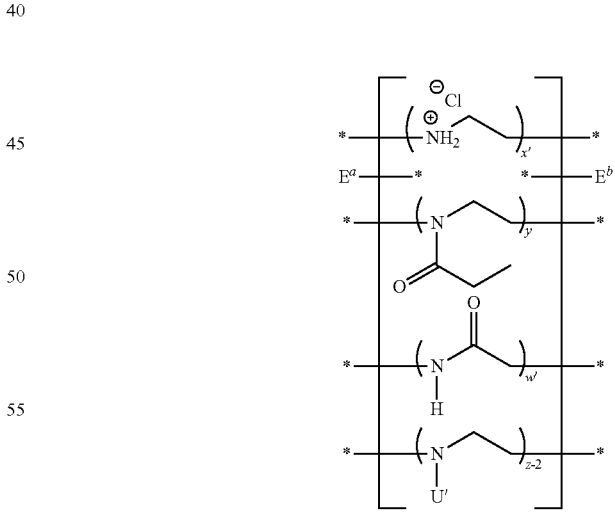

L21
$x' = 209$
$y = 8$
$w' = 30$
$z = 10$
$E^a = *\text{---}CH_2CH_2NH\text{---}U'$
$E^b = NH\text{---}U'$ U' = 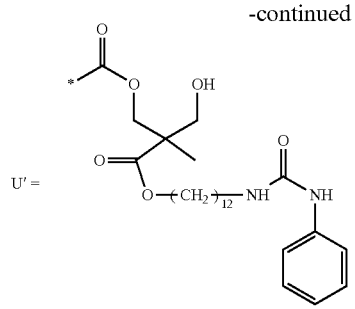

LPEI25 (0.3 g, 0.027 mmol) was heated for 3 hours in a flask at 60° C. in vacuum and cooled to room temperature. Dioxane (30 mL) was added to the flask. The flask was fitted with a condenser and the mixture was heated to 85° C. while exposed to air. After all the LPEI25 was dissolved in the dioxane and a homogeneous solution was obtained (about 2 hours), a solution of MTC-PUC12 (0.11 g. 0.24 mmol) in 10 mL of dioxane was added and the solution was heated overnight at 85° C. with stirring (about 16 hours) while exposed to air. The reaction mixture was cooled to room temperature and the solvent was removed by rotary evaporation. MeOH (10 mL) and aqueous HCl solution (1 M, 10 mL) were sequentially added to the flask, and the resulting mixture was stirred for 2-3 hours. After the solution was concentrated by rotary evaporation, the resulting acidified crude product was precipitated in THF, centrifuged and washed with THF 3 times. The wet solid was dissolved in a small volume of DI water and lyophilized to give L21 as reddish solid (0.55 g, 85%). $^1$H NMR (400 MHz, D$_2$O, 22° C.): δ 7.14 (m, 50H, -PhH), 4.01 (d, 60H, —CH$_2$OCOO— and —OCH$_2$(CH$_2$)$_{10}$CH$_2$NH—), 2.80-3.90 (m, 1040H, —CH$_2$CH$_2$NH$^⊕$— and —OCH$_2$(CH$_2$)$_{10}$CH$_2$NH—), 2.37 (m, 16H, —NC(O)CH$_2$CH$_3$), 0.98-1.14 (m, 230H, —OCH$_2$(CH$_2$)$_{10}$CH$_2$NH— and —CH$_3$), 0.93 (t, 24H, —NC(O)CH$_2$CH$_3$). In the above structure for L21 and those structures below derived from LPEI25, x' represents the remaining number of secondary amine sites in the form of a protonated salt after modification. The subscript z' represents the total number of U' groups in the cationic polyamine. In this instance, z'=10, with each end group E$^a$ and E$^b$ comprising a U' group (*—CH$_2$CH$_2$NH—U' and *—NH—U', respectively). The quantity z-2 represents the number of secondary ethylenimine units bearing a U' moiety. The quantity w' represents the number of oxidized ethylenimine units in the product. In L21, about 3.8% of the 247 secondary amine groups of LPEI25 were modified to contain a urea group (x'=209, y=8, w'=30, and z=10).

Example 22

Purification of L21 to form L22. L21 (50 mg) was dissolved in 5 ml of DI-water (pH 1.9), transferred to a 15-ml centrifugal concentrator (MWCO=3,000) and then washed with DI-water for 3 times prior to lyophilization, to give L22 as a reddish solid (43 mg).

Example 23

Neutralization of L21 to form L23. L21 (50 mg) was dissolved in deionized water (DI water, 5 mL) and adjusted to pH 7.2 with 0.1M NaOH solution. The mixture was transferred to a 15-ml centrifugal concentrator (MWCO=3,000) and washed with DI-water for 3 times prior to lyophilization, yielding a yellow powder.

Example 24

Preparation of L24 by reaction of LPEI25 with MTC-PUC12 (z=16).

LPEI25 + 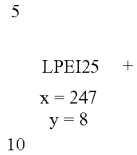
x = 247
y = 8

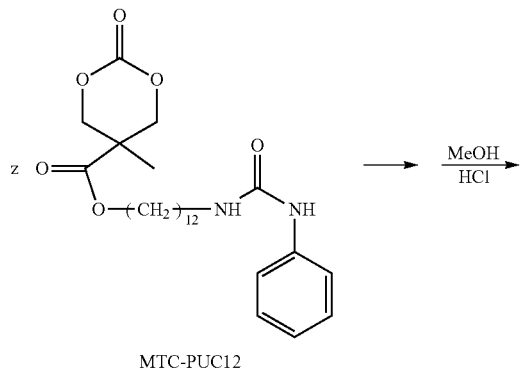

MTC-PUC12

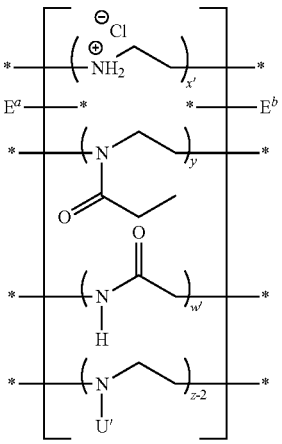

L24
x' = 203
y = 8
w' = 30
z = 16
E$^a$ = *—CH$_2$CH$_2$NH—U'
E$^b$ = NH—U'

U' = 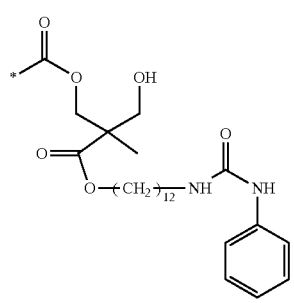

The procedure of Example 21 was followed using LPEI25 (0.3 g, 0.027 mmol) in dioxane (30 mL) and MTC-PUC12 (0.17 g, 0.36 mmol) in dioxane (30 mL) to provide the conjugate L24 isolated as a reddish solid (yield 0.57 g, 81%, x'=203, y=8, w'=30, and z=16). About 6.9% of the 247 secondary amine groups of LPEI25 were modified to contain a urea group. $^1$H NMR (400 MHz, D$_2$O, 22° C.): delta 7.17 (m, 80H, -PhH), 4.03 (d, 96H, —CH$_2$OCOO— and —OCH$_2$(CH$_2$)$_{10}$CH$_2$NH—), 2.78-3.90 (m, 1052H, —CH$_2$CH$_2$NH$^{\oplus}$— and —OCH$_2$(CH$_2$)$_{10}$CH$_2$NH—), 2.39 (m, 16H, —NC(O)CH$_2$CH$_3$), 0.96-1.15 (m, 368H, —OCH$_2$(CH$_2$)$_{10}$CH$_2$NH— and —CH$_3$), 0.94 (t, 24H, —NC(O)CH$_2$CH$_3$).

Example 25

Purification of L24 to form L25. L24 (50 mg) was dissolved in 5 ml of DI-water (pH 1.9), transferred to a 15-ml centrifugal concentrator (MWCO=3,000) and then washed with DI-water for 3 times prior to lyophilization, to give L25 as a reddish solid (45 mg).

Example 26

Neutralization of L24 to form L26. L24 (50 mg) was dissolved in deionized water (DI water, 5 mL) and adjusted to pH 7.2 with 0.1M NaOH solution. The mixture was transferred to a 15-ml centrifugal concentrator (MWCO=3,000) and washed with DI-water for 3 times prior to lyophilization, yielding a yellow powder.

Example 27

Preparation of L27, by reaction of LPEI25 with MTC-IPMAN (z=8).

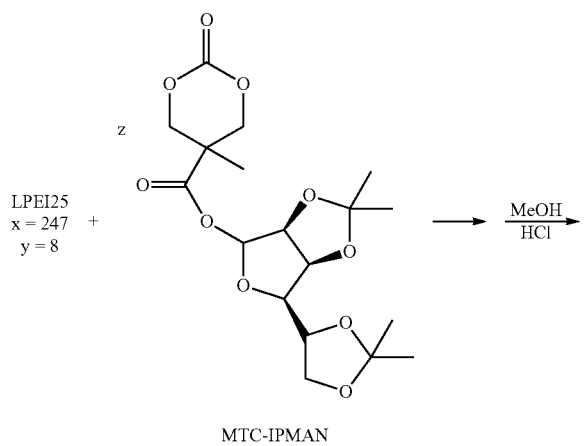

MTC-IPMAN

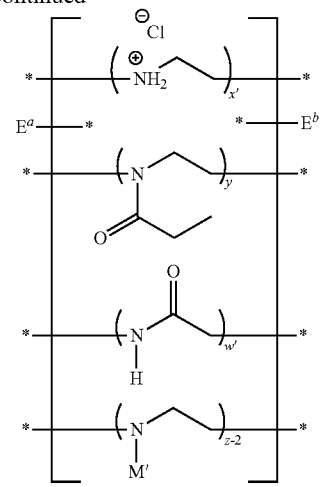

L27

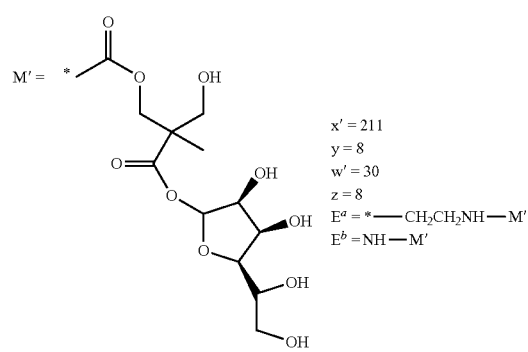

The procedure of Example 21 was followed using LPEI25 (0.36 g, 0.033 mmol) in dioxane (20 mL) and MTC-IPMAN (0.06 g, 0.15 mmol) in dioxane (10 mL) The acidification step was slightly different because the protecting groups of mannose moiety could be removed while the amine groups of LPEI were acidified. Therefore, after the addition of 10 mL of MeOH and 10 mL of 1 M HCl aqueous solution to the initial polyamine, the flask was heated to 102° C. and the solution was refluxed for 2 hours. The flask was cooled to room temperature and the solution was concentrated by rotary evaporation. The crude product was purified by centrifugal filtration (MWCO=3,000) and washed twice with DI water, to give the conjugate L27 isolated as a brown solid (yield 0.53 g, 76%, x'=211, y=8, w'=30, and z=8). $^1$H NMR (400 MHz, D$_2$O, 22° C.): delta 3.95 (s, 32H, —CH$_2$OCOO—), 3.00-3.90 (m, 1044H, —CH$_2$CH$_2$NH$^{\oplus}$— and H of mannose moieties), 2.37 (m, 16H, —NC(O)CH$_2$CH$_3$), 1.08 (m, 24H, —CH$_3$), 0.94 (t, 24H, —NC(O)CH$_2$CH$_3$).

Example 28

Preparation of L28, by reaction of LPEI25 with MTC-IPMAN (z=14).

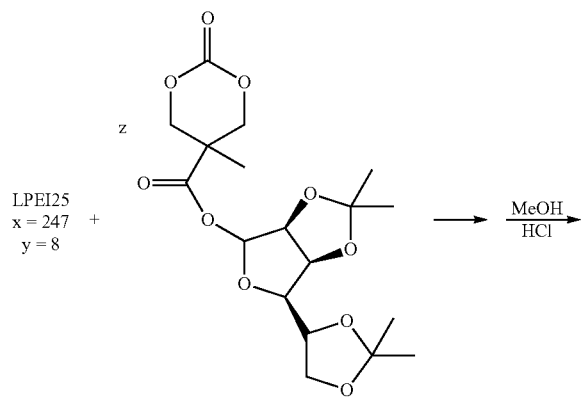
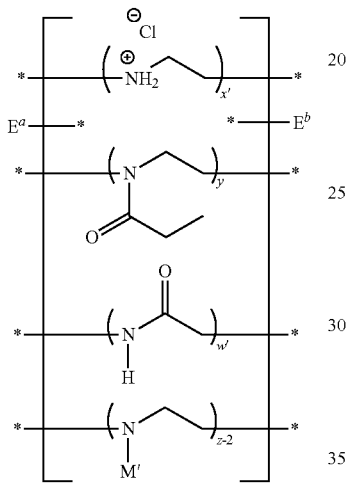
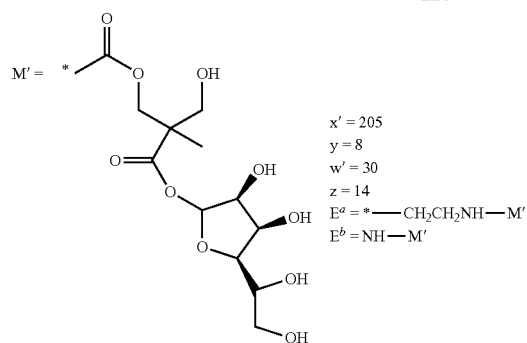

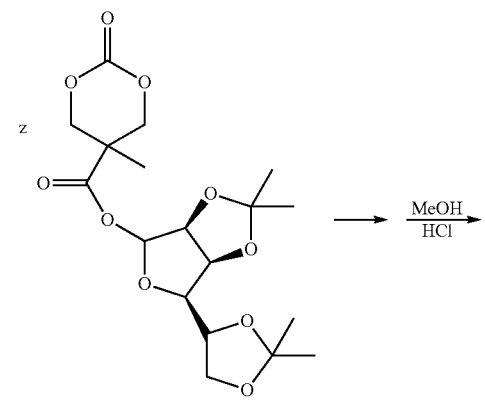
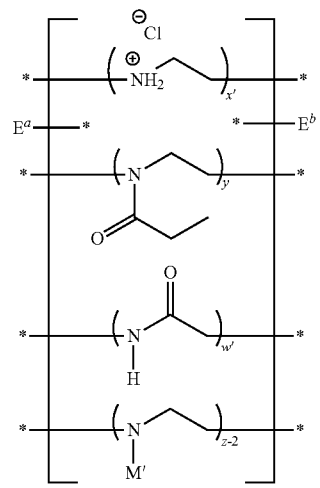
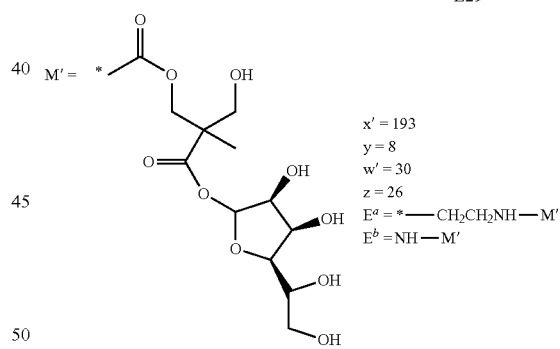

The procedure of Example 27 was followed using LPEI25 (0.375 g, 0.034 mmol) in dioxane (30 mL) and MTC-IPMAN (0.125 g, 0.31 mmol) in dioxane (10 mL) to provide the conjugate L28 isolated as a brown solid (yield 0.58 g, 76%, x'=205, y=8, w'=30, and z=14). $^1$H NMR (400 MHz, D$_2$O, 22° C.): delta 3.97 (s, 56H, —CH$_2$OCOO—), 3.05-3.90 (m, 1062H, —CH$_2$CH$_2$NH$^\oplus$— and H of mannose moieties), 2.38 (m, 16H, —NC(O)CH$_2$CH$_3$), 1.03 (m, 42H, —CH$_3$), 0.94 (t, 24H, —NC(O)CH$_2$CH$_3$).

The procedure of Example 27 was followed using LPEI25 (0.25 g, 0.023 mmol) in dioxane (30 mL) and MTC-IPMAN (0.25 g, 0.62 mmol) in dioxane (10 mL) to provide the conjugate L29 isolated as a brown solid (yield 0.45 g, 71%, x'=193, y=8, w'=30, and z=26). $^1$H NMR (400 MHz, D$_2$O, 22° C.): δ 3.96 (s, 104H, —CH$_2$OCOO—), 3.08-3.88 (m, 1098H, —CH$_2$CH$_2$NH$^\oplus$— and H of mannose moieties), 2.37 (m, 16H, —NC(O)CH$_2$CH$_3$), 1.07 (m, 78H, —CH$_3$), 0.95 (t, 24H, —NC(O)CH$_2$CH$_3$).

Example 29

Preparation of L29, by reaction of LPEI25 with MTC-IPMAN (z=26).

Example 30

Preparation of L30, by reaction of LPEI25 with trimethylene carbonate (TMC, z=6).

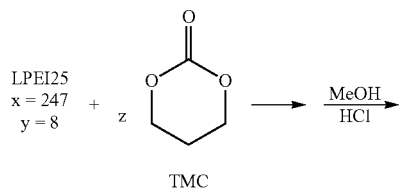

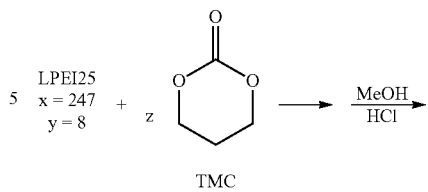

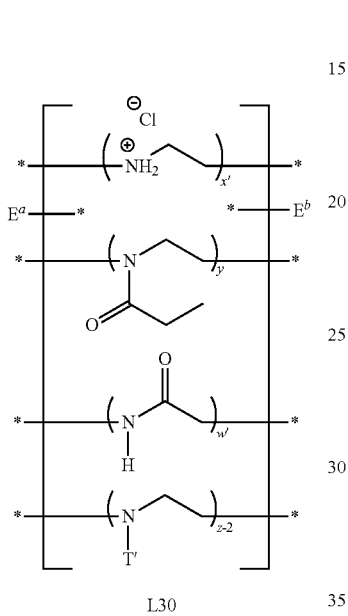

L30

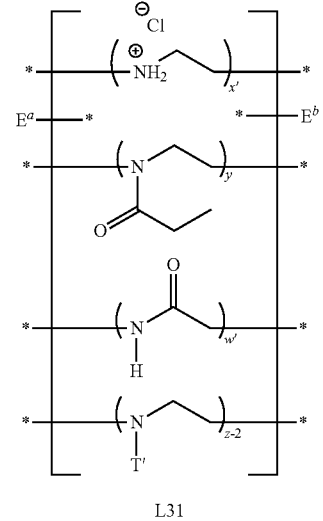

L31

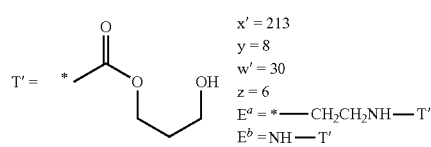

The procedure of Example 21 was followed using LPEI25 0.36 g, 0.033 mmol) in dioxane (20 mL) and TMC (0.06 g, 0.59 mmol) in dioxane (10 mL) to provide the conjugate L30 isolated as a brown solid (yield 0.57 g, 81%, x'=213, y=8, w'=30 and z=6). $^1$H NMR (400 MHz, D$_2$O, 22° C.): delta 4.10 (m, 24H, —CH$_2$OCOO—), 3.06-3.98 (m, 1020H, —CH$_2$CH$_2$NH$^\oplus$—), 2.36 (m, 16H, —NC(O)CH$_2$CH$_3$), 1.78 (m, 12H, —CH$_2$— of TMC), 0.94 (t, 24H, —NC(O) CH$_2$CH$_3$).

Example 31

Preparation of L31, by reaction of LPEI25 with TMC (z=11).

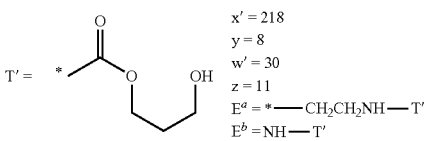

The procedure of Example 30 was followed using LPEI25 (0.3 g, 0.027 mmol) in dioxane (20 mL) and TMC (0.1 g, 0.98 mmol) in dioxane (10 mL) to provide the conjugate L31 isolated as a brown solid (yield 0.53 g, 84%, x=218, y=8, w'=30, and z=11). $^1$H NMR (400 MHz, D$_2$O, 22° C.): delta 4.11 (m, 44H, —CH$_2$OCOO—), 3.05-3.89 (m, 1020H, —CH$_2$CH$_2$NH$^\oplus$—), 2.37 (m, 16H, —NC(O)CH$_2$CH$_3$), 1.80 (m, 22H, —CH$_2$— of TMC), 0.94 (t, 24H, —NC(O) CH$_2$CH$_3$).

Example 32

Preparation of L32 by reaction of LPEI25 with TMC (z=16).

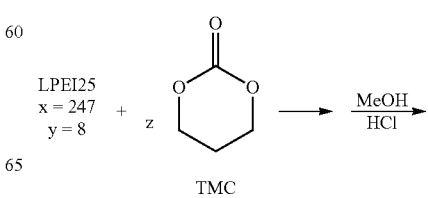

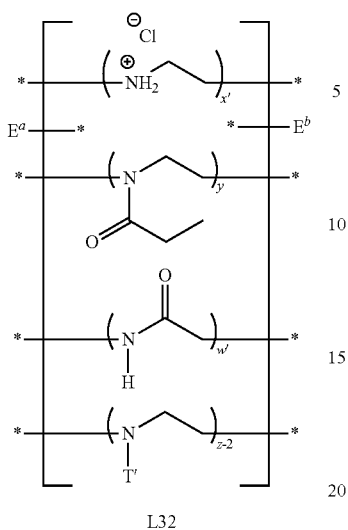

L32

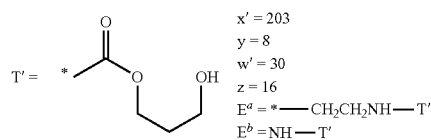

$x' = 203$
$y = 8$
$w' = 30$
$z = 16$
$E^a = *\text{—CH}_2\text{CH}_2\text{NH—T}'$
$E^b = \text{NH—T}'$ The procedure of Example 30 was followed using LPEI25 (0.18 g, 0.016 mmol) in dioxane (20 mL) and TMC (0.18 g, 1.76 mmol) in dioxane (10 mL) to provide the conjugate L32 isolated as a brown solid (yield 0.41 g, 83%, x=203, y=8, w'=0, and z=16). $^1$H NMR (400 MHz, $D_2O$, 22° C.): delta 4.11 (m, 64H, —$CH_2OCOO$—), 3.05-3.89 (m, 1020H, —$CH_2CH_2NH^\oplus$—), 2.36 (m, 16H, —NC(O)$CH_2CH_3$), 1.79 (m, 32H, —$CH_2$— of TMC), 0.94 (t, 24H, —NC(O)$CH_2CH_3$).

Example 33

Preparation of L33, by reaction of LPEI25 with MTC-PUC8 (z=10) in chloroform.

LPEI25
x = 247
y = 8
+

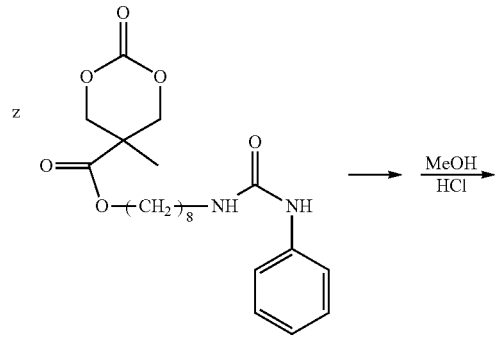

MTC-PUC8

→ MeOH/HCl

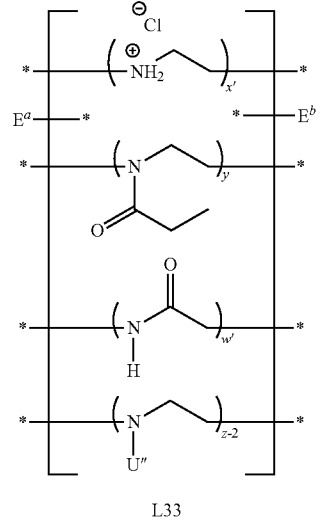

L33

$U'' =$ 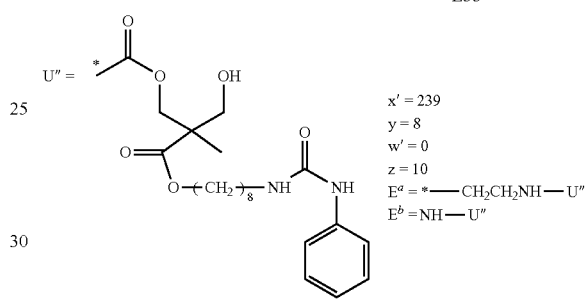

$x' = 239$
$y = 8$
$w' = 0$
$z = 10$
$E^a = *\text{—CH}_2\text{CH}_2\text{NH—U}''$
$E^b = \text{NH—U}''$ The procedure of Example 21 was followed using LPEI25 0.36 g, 0.033 mmol) in chloroform (20 mL) and MTC-PUC8 (0.06 g, 0.59 mmol) in chloroform (10 mL) to provide the conjugate L33 isolated as a light yellow solid (yield 0.57 g, 81%, x'=239, y=8, w'=0 and z=10). $^1$H NMR (400 MHz, $D_2O$, 22° C.): delta 4.10 (m, 24H, —$CH_2OCOO$—), 3.06-3.98 (m, 1020H, —$CH_2CH_2NH^\oplus$—), 2.36 (m, 16H, —NC(O)$CH_2CH_3$), 1.78 (m, 12H, —$CH_2$— of TMC), 0.94 (t, 24H, —NC(O)$CH_2CH_3$).

Example 34

Purification of L33 to form L34. L34 (50 mg) was dissolved in 5 ml of DI-water (pH 1.9), transferred to a 15-ml centrifugal concentrator (MWCO=3,000) and then washed with DI-water for 3 times prior to lyophilization, to give L34 as a light yellow solid (45 mg).

Example 35

Neutralization of L33 to form L35. L33 (50 mg) was dissolved in deionized water (DI water, 5 mL) and adjusted to pH 7.2 with 0.1 M NaOH solution. The mixture was transferred to a 15-ml centrifugal concentrator (MWCO=3,000) and washed with DI-water for 3 times prior to lyophilization, yielding a light yellow powder.

Example 36

Preparation of L36 by reaction of LPEI25 with MTC-OBn (z=12).

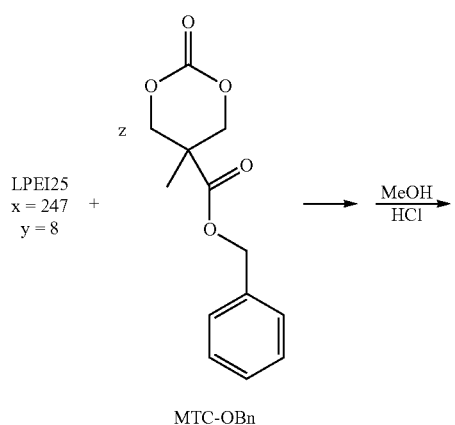

MTC-OBn

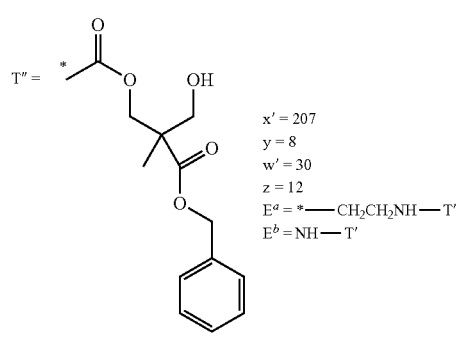

L36

The procedure of Example 30 was followed using LPEI25 (0.18 g, 0.016 mmol) in dioxane (20 mL) and MTC-OBn (0.18 g, 1.76 mmol) in dioxane (10 mL) to provide the conjugate L36. The product was further purified by washing the polymer according to the procedure of Example 34. L36 was isolated as a red solid (yield 0.41 g, 83%, x=207, y=8, w'=30, and z=12). $^1$H NMR (400 MHz, D$_2$O, 22° C.): delta 7.34 (m, 60H, PhH), 5.21 (s, 24H, —CH$_2$Ph), 4.11 (m, 48H, —CH$_2$OCOO—), 3.05-3.89 (m, 1020H, —CH$_2$CH$_2$NH$^\oplus$—), 2.36 (m, 16H, —NC(O)CH$_2$CH$_3$), 1.18 (s, 36H, —CH$_3$), 0.94 (t, 24H, —NC(O)CH$_2$CH$_3$).

Example 37

Preparation of L37 by reaction of LPEI25 with MTC-OBn (z=12). The procedure of Example 36 was followed, and the product was neutralized according to Example 35, resulting in a yellow solid.

Example 38

Purification of L27 to form L38. L27 (50 mg) was dissolved in 5 ml of DI-water (pH 1.9), transferred to a 15-ml centrifugal concentrator (MWCO=3,000) and then washed with DI-water for 3 times prior to lyophilization, to give L38 as a brown solid (42 mg).

Example 39

Neutralization of L27 to form L39. L27 (50 mg) was dissolved in deionized water (DI water, 5 mL) and adjusted to pH 7.2 with 0.1M NaOH solution. The mixture was transferred to a 15-ml centrifugal concentrator (MWCO=3,000) and washed with DI-water for 3 times prior to lyophilization, yielding a yellow powder.

Example 40

Purification of L28 to form L40. L28 (50 mg) was dissolved in 5 ml of DI-water (pH 1.9), transferred to a 15-ml centrifugal concentrator (MWCO=3,000) and then washed with DI-water for 3 times prior to lyophilization, to give L40 as a brown solid (46 mg).

Example 41

Neutralization of L28 to form L41. L28 (50 mg) was dissolved in deionized water (DI water, 5 mL) and adjusted to pH 7.2 with 0.1M NaOH solution. The mixture was transferred to a 15-ml centrifugal concentrator (MWCO=3,000) and washed with DI-water for 3 times prior to lyophilization, yielding a yellow powder.

Example 42

Preparation of cationic polycarbonate PC1 by ring opening polymerization of MTC-BnCl (degree of polymerization (DP)=20) initiated with cholesterol.

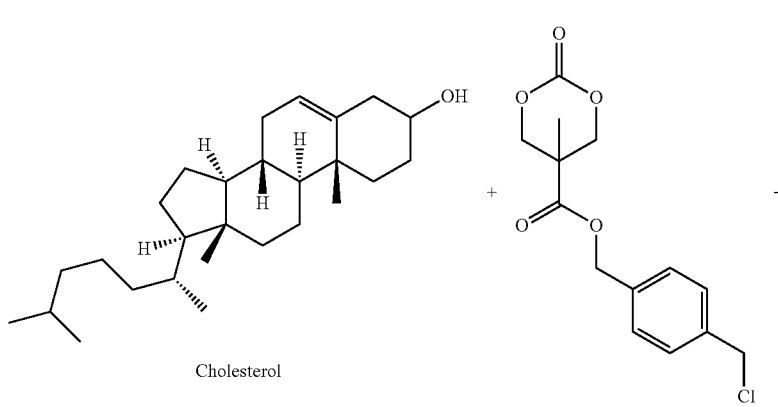
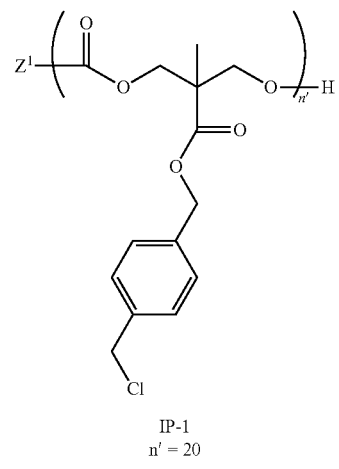
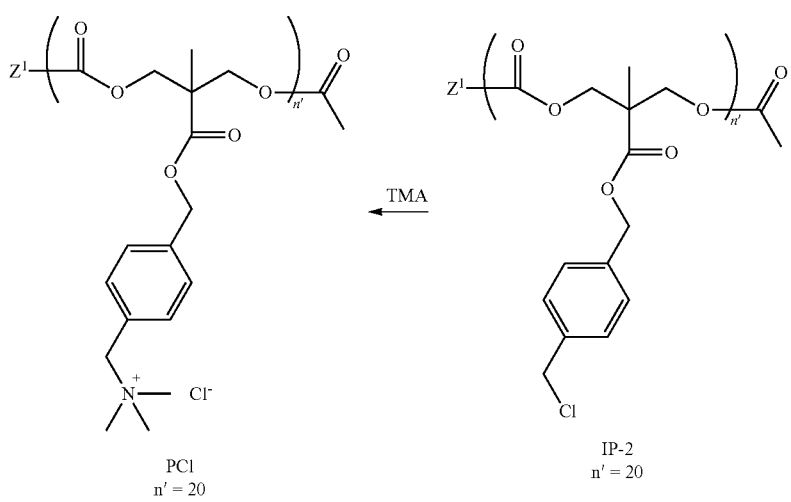
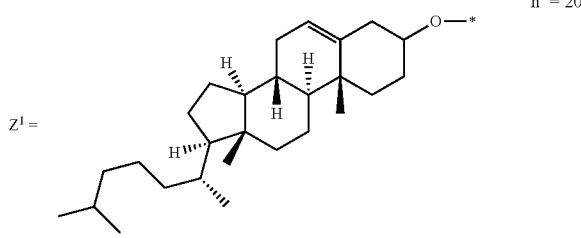

Part 1. In an inert glovebox a vial was charged with cholesterol (0.0645 g, 0.167 mmol), MTC-BnCl (1.0 g, 3.34 mmol), dichloromethane (DCM) (3.0 mL) and a stir bar. The reaction mixture was stirred and the polymerization started by the addition of DBU (0.01 g, 0.0657 mmol). After 15 minutes excess acetyl chloride was added to quench the reaction and acetylate the IP-1 termini to form IP-2. Acetylated intermediate polymer IP-2 was precipitated into isopropanol yielding 0.93 g (87%) white waxy polymer. The polymer was characterized using $^1$HNMR (CDCl$_3$) and GPC (THF, 37° C.). Complete polymerization was verified by the disappearance of a carbonate doublet (2H, —OCOOCH$_2$—, 4.7 ppm) with corresponding appearance of broad multiplet (6H, 4.2 ppm) encompassing both newly formed linear carbonate methylenes (—CH$_2$OCOOCH$_2$—) and the benzyl ester. Molecular weight was verified by GPC and found to be 2.6 kDa with a PDI of 1.2. The average degree of polymerization (DP) was calculated by taking the ratio of cholesteryl methyl shift integration (3H, 0.87 ppm) against the benzyl chloride signal (2H, 5.0 ppm) which was in good agreement with GPC values.

Part 2. Quaternization of IP-2 with trimethylamine (TMA) to form CP-1. A vial was charged with acetylated intermediate polymer IP-2 (0.4 g), acetonitrile (6 mL) and a stir bar. The reaction mixture was then placed in a dry ice/acetone bath (−78° C.) and excess TMA gas was bubbled through the stirred solution. The vial was then sealed and allowed to warm to ambient temperature with stirring. After 4 hours the diethyl ether (5 mL) was added to precipitate the product polymer. The reaction vial was then centrifuged for 10 minutes and the supernatant was decanted. The product was washed with excess diethyl ether and dried under high vacuum to yield 0.45 g (94%) translucent waxy material. The quaternization was verified using $^1$H NMR. A diagnostic chemical shift attributable to quaternized TMA (9H, 3.2 ppm) appeared and could be integrated against the benzyl ammonium signal (2H, 5.0 ppm) verifying complete conversion. DP=20 (n'=20).

Example 43

Preparation of cationic polycarbonate PC2 by ring opening polymerization of MTC-BnCl (DP=10, n'=10) initiated with Chol-OPr—OH.

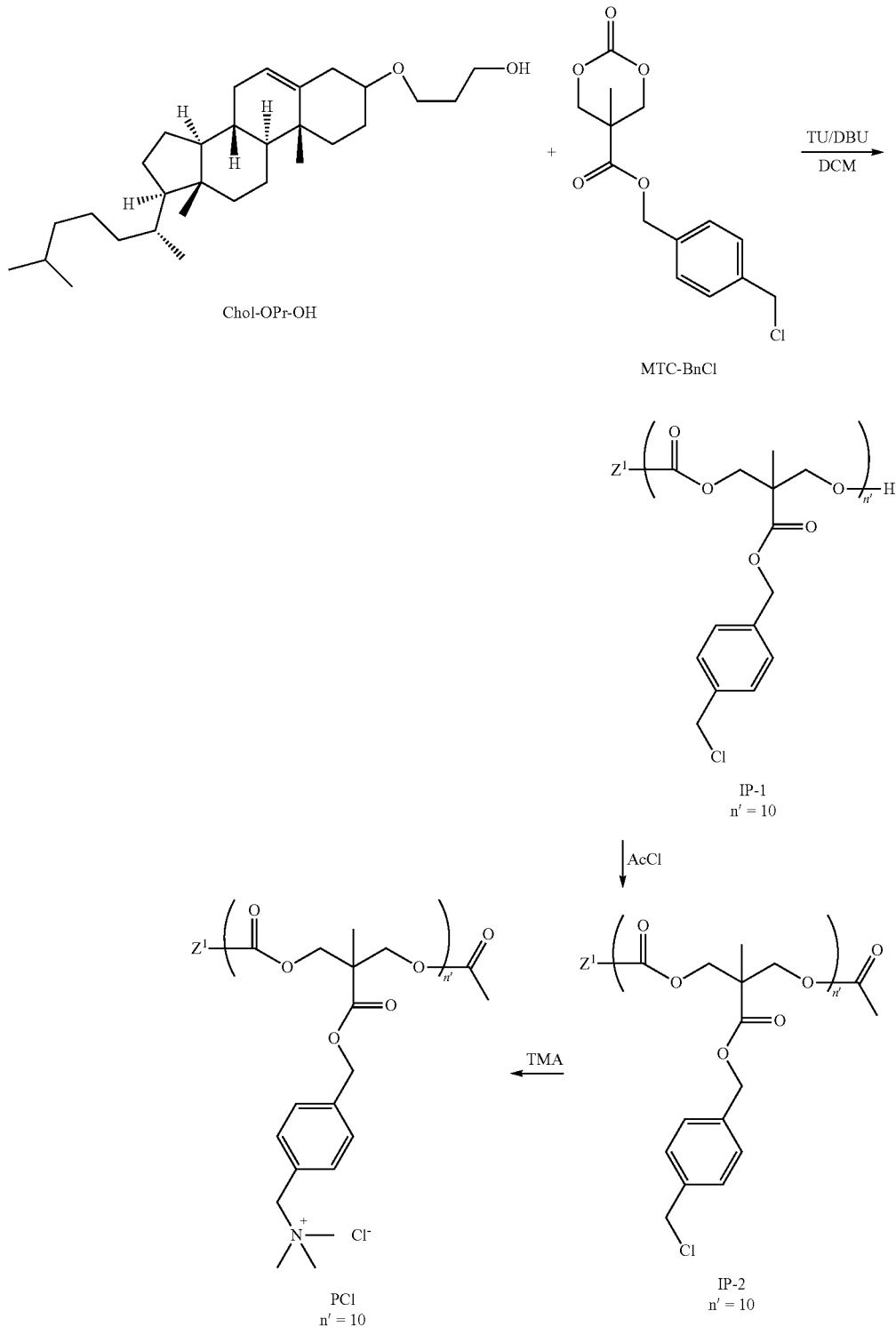

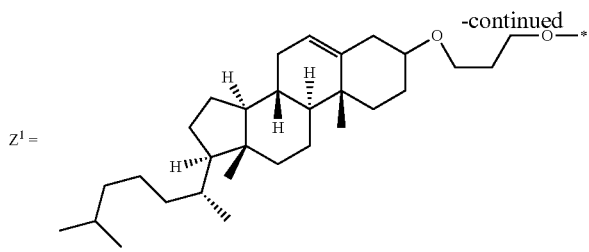

Cationic polyamine PC2 was prepared according to procedure of Example 33 using Chol-OPr—OH (0.0645 g, 0.167 mmol), MTC-BnCl (0.5 g, 1.67 mmol), dichloromethane (DCM) (1.5 mL) and DBU (0.01 g, 0.0657 mmol).

In the following examples the structure of BPEI25 is represented by the structure:

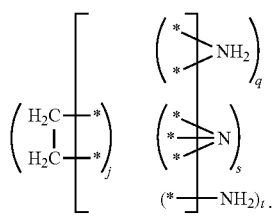

BPEI25
Mw = 25 kDa
Mn = 10 kDa
q = 116
s = 58
t = 58
j = 233

The subscript q represents the number of secondary nitrogen groups. For BPEI25, q=116. The subscript s represents the number of tertiary amine groups. For BPEI25, s=58. The subscript t represents the number of primary amine end groups. For BPEI25, t=58. The subscript j represents the number of ethylene groups. For BPEI25, j=233. BPEI25 has an average of 58 primary amine groups, 116 secondary amine groups, 58 tertiary amine groups per mole based on 1 mole=10000 g. It should be understood that each starred bond of a given nitrogen of the right bracket is linked to a different ethylene group of the left bracket. The tertiary, secondary and primary amine groups are randomly distributed in BPEI25, indicated by the vertical stacking of the amine groups on the right square bracket. BPEI25 contains numerous branches that intersect at the tertiary amine sites. Branches terminate at a peripheral end with a primary amine group.

Example 44

Preparation of B1, branched polyethylenimine (BPEI25, Mn 10,000) modified with MTC-IPMAN (67 mannose groups introduced).

The MTC-IPMAN was used in excess of the primary amine groups of BPEI25; therefore the primary amine groups and secondary amine groups of BPEI25 react with MTC-IPMAN without ring opening polymerization of MTC-IPMAN. The reaction introduces 67 protected mannose units into BPEI25, modifying about 100% of the BPEI25 primary amine groups and about 8% of the secondary amine sites, each with a single ring opened subunit of MTC-IPMAN. Hydrolysis of the isopropylidene ketal protecting groups results in 67 mannose units linked to BPEI25. The subscripts q', s', t', u, and v in the structure for B1 below represent average number of functional groups in a macromolecule of the cationic polyamine. Theoretical values of the subscripts in the final structure of B1 are q'=107, s'=58, t'=0, u=9, and v=58. Actual values found by NMR were q'=116, s'=58, t'=38, u=0, v=20.

BPEI25
Mw = 25 kDa
Mn = 10 kDa
q = 116
s = 58
t = 58
j = 233

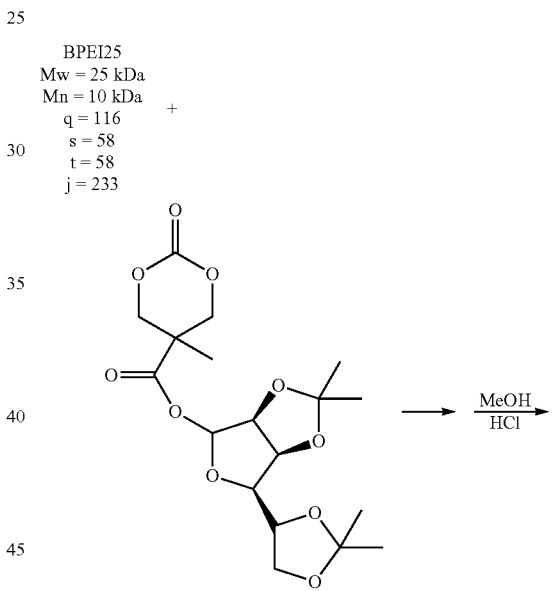

MTC-IPMAN

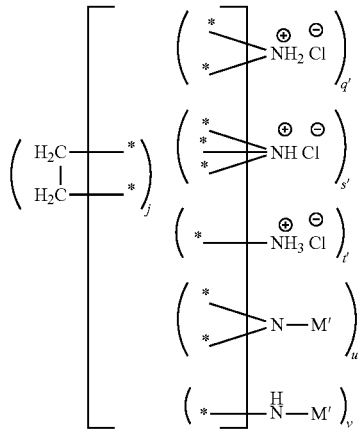

B1

-continued

M' = 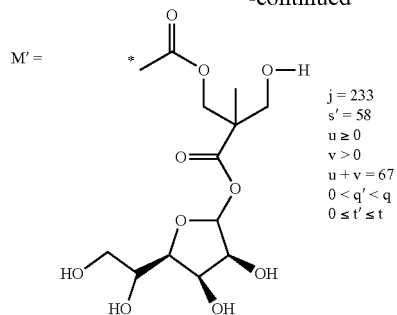

j = 233
s' = 58
u ≥ 0
v > 0
u + v = 67
0 < q' < q
0 ≤ t' ≤ t

In a glove box, MTC-IPMAN (0.375 g, 0.933 mmol, MW=402.15 g) was added to the solution of BPEI25 (0.125 g, 0.0125 mmol based on 1 mole=10,000 g=Mn) in 2 mL of dichloromethane (DCM). The BPEI25:MTC-IPMAN feed mass ratio was 1:3, the molar ratio was 1:75. The reaction solution was stirred for 1 hour. 10 mL of methanol and 10 mL of 1 M HCl (aq.) were added. The resulting reaction mixture was heated at reflux for 2 hours before cooling to room temperature. Finally, the above mixture was purified by ultrafiltration in a Vivaspin 20 concentrator (MWCO=3000). In the above structure for B1 and in the structures that follow, s'=58 and represents the number of protonated tertiary amine groups, q' represents the number of remaining secondary amine groups in the form of a protonated salt, t' represents the number of remaining primary amine end groups in the form of a protonated salt, u represents the number of modified secondary amine groups bearing the moiety M', and v represents the number of modified primary amine groups bearing the moiety M'. In B1, the quantity u+v=67.

Example 45

Preparation of B2, branched polyethyleneimine (BPEI25, Mn 10,000) modified with MTC-PUC8 (16 urea groups introduced).

BPEI25
Mw = 25 kDa
Mn = 10 kDa
q = 116
s = 58
t = 58
j = 233

+

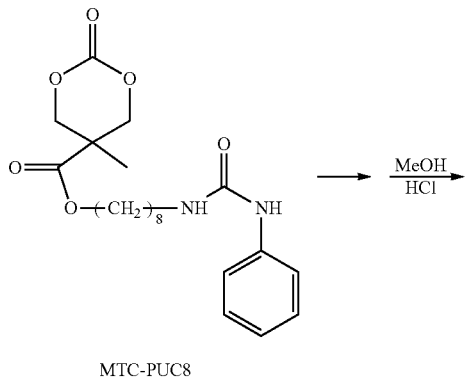

MTC-PUC8

$\xrightarrow{\text{MeOH}}{\text{HCl}}$

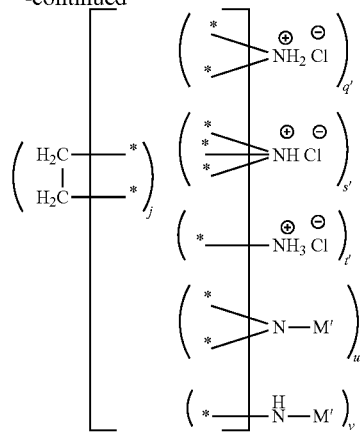

B2

U' = 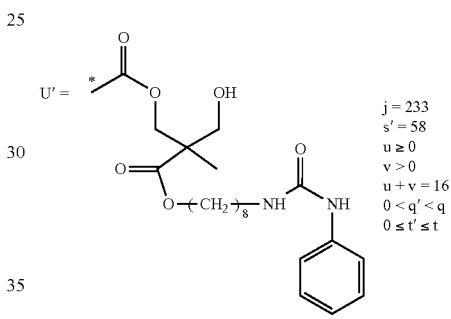

j = 233
s' = 58
u ≥ 0
v > 0
u + v = 16
0 < q' < q
0 ≤ t' ≤ t

In a glove box, MTC-PUC8 (0.122 g, 0.3 mmol) was added to the solution of BPEI25 (0.3 g, 0.03 mmol based on 1 mole=10,000 g=Mn) in 2 mL of dichloromethane (DCM). The BPEI25:MTC-PUC8 feed mass ratio was 1:0.41, the molar ratio was 1:10. The reaction solution was stirred for 1 hour. 10 mL of methanol and 10 mL of 1 M HCl (aq.) were added, and stirred for 2-3 hours. Finally, the above mixture was purified by ultrafiltration in a Vivaspin 20 concentrator (MWCO=3000). About 16 sites (9.1% of the 174 secondary amine plus primary amine sites of BPEI25) were modified to contain a urea group.

Example 46

Preparation of B3, branched polyethyleneimine (BPEI25, Mn 10,000) modified with MTC-PUC8 (33 urea groups introduced).

BPEI25
Mw = 25 kDa
Mn = 10 kDa
q = 116
s = 58
t = 58
j = 233

+

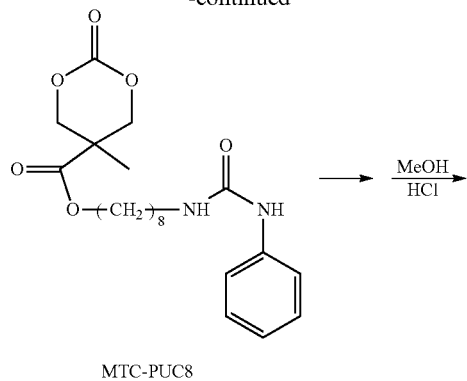

MTC-PUC8

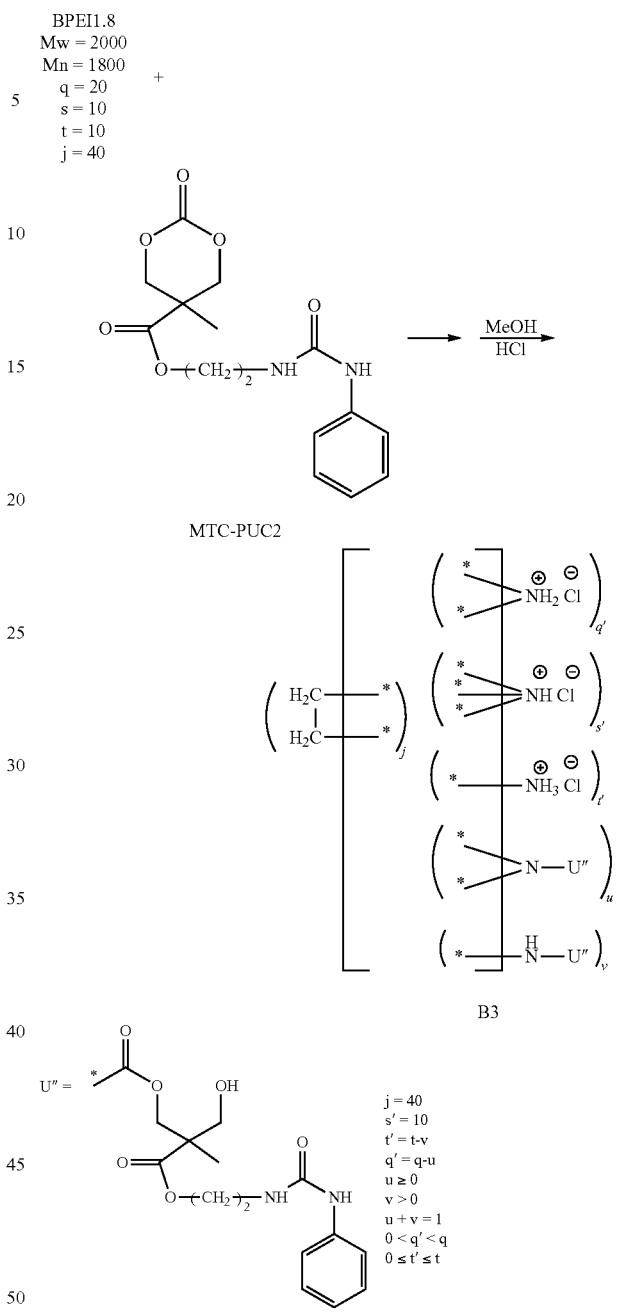

MTC-PUC2

In a glove box, MTC-PUC8 (0.163 g, 0.4 mmol) was added to the solution of BPEI25 (0.2 g, 0.02 mmol based on 1 mole=10,000 g=Mn) in 2 mL of DCM. The BPEI25:MTC-PUC8 feed mass ratio was 1:0.82, and the molar ratio was 1:20. The reaction solution was stirred for 1 hour. 10 mL of methanol and 10 mL of 1 M HCl (aq.) were added, and stirred for 2-3 hours. Finally, the above mixture was purified by ultrafiltration in a Vivaspin 20 concentrator (MWCO=3000). About 33 sites (18.9% of the 174 secondary amine plus primary amine groups of BPEI25) were modified to contain a urea group.

Example 47

Preparation of B4, branched polyethyleneimine (BPEI1.8, Mn=1800) modified with MTC-PUC2 (1 urea group introduced).

In a glove box, MTC-PUC2 (64.4 g, 0.2 mmol) was added to the solution of BPEI1.8 (0.36 g, 0.2 mmol based on 1 mole=1800 g=Mn) in 2 mL of DCM. The BPEI1.8:MTC-PUC2 feed mass ratio was 5.6:1, the molar ratio was 1:1. The reaction solution was stirred for 1 hour, precipitated in $Et_2O$, and washed with $Et_2O$ three times. Finally, the residue was dried in vacuo to give B4. An average of 1 site of the BPEI1.8 was modified to contain a urea group. $^1$H NMR (400 MHz, MeOD, 22° C.): delta 7.36 (s, 2H, PhH), 7.27 (s, 2H, PhH), 6.99 (s, 1H, PhH), 4.21 (m, 4H, —$CH_2OCOO$— and —$COOCH_2$—), 3.68 (m, 4H, —$CH_2OCOO$— and —$CH_2NHC(O)NHPh$), 2.50-2.94 (m, 167H, H of BPEI1.8), 1.21 (s, 3H, —$CH_3$).

Catechol-Modified LPEI25 and BPEI25

The PEIs were modified using a cyclic carbonate monomer functionalized with a benzyl-protected catechol group (MTC-Catechol) or dopamine group (MTC-dopamine) through ring opening of the cyclic carbonate by the PEI nitrogens. The benzyl protecting groups of the MTC-Catechol modified PEI were removed by hydrogenation catalyzed by Pd/C, and the deprotected polymer was acidified with 1 M HCl (aq.). The resulting cationic modified linear and branched PEI derivatives were coated onto a contact lens and a poly(ethylene terephthalate) (PET) plastic water bottle, via a one-step immersion procedure. The antimicrobial activities of the coatings were assessed, and the effects of catechol groups on the coating of the different surfaces was examined.

Example 48

Preparation of L42 by reaction of LPEI25 with MTC-catechol (total of 11 catechol groups introduced in the form of $H^a$ and $H^b$ below, where the ratio $H^a$:$H^b$=9:2). Each end group can have an $H^a$ substituent ($E^a$=*—$CH_2CH_2NH$—$H^a$, $E^b$=*—NH—$H^a$) or an $H^b$ substituent ($E^{a'}$=*—$CH_2CH_2NH$—$H^b$, $E^{b'}$=*—NH—$H^b$).

LPEI25
x = 247
y = 8

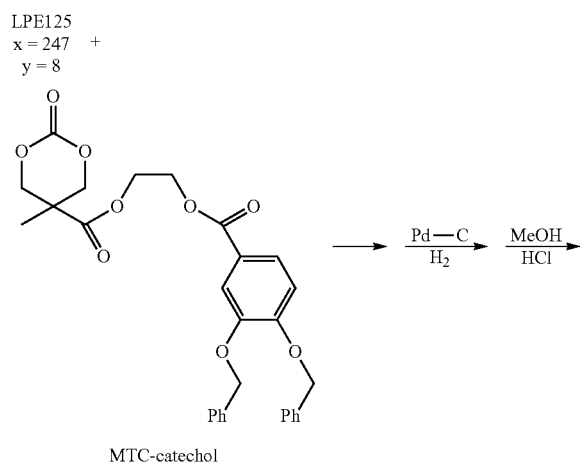

MTC-catechol

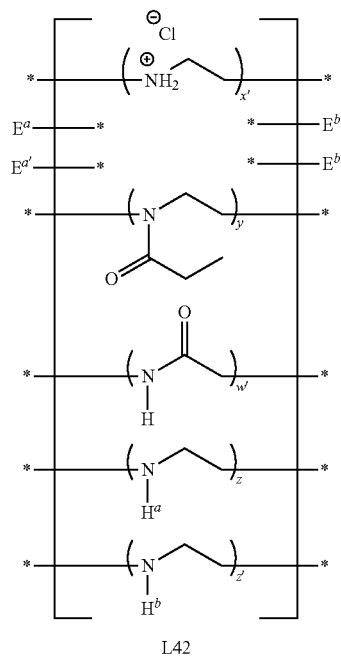

L42

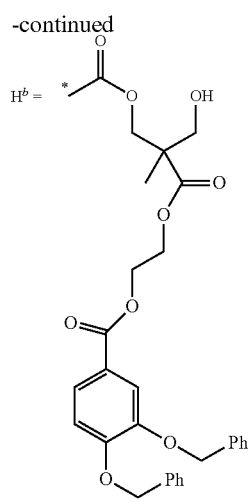

x' = 208
y = 8
w' = 30
z' + z = 9
$H^a$:$H^b$ = 9:2
$E^a$ = *——$CH_2CH_2NH$——$H^a$
$E^{a'}$ = *——$CH_2CH_2NH$——$H^b$
$E^b$ = * NH——$H^a$
$E^{b'}$ = * NH——$H^b$

LPEI25 (0.4 g, 0.037 mmol) was heated for 3 hours in a flask at 65° C. in vacuum. When the flask cooled to room temperature, 30 mL of dioxane was added to the flask. Then, the flask was charged with condenser and heated to 85° C. After all the LPEI25 was dissolved in dioxane and a homogeneous solution was obtained, a solution of MTC-Catechol (83 mg, 0.16 mmol) in 10 mL of dioxane was added. The reaction mixture was stirred overnight at 85° C. in contact with air. The flask cooled to room temperature, and the solvent was removed by rotary evaporation. The resulting product was dried in vacuum.

A mixture of the above conjugate, MeOH (7.5 mL), THF (7.5 mL), and Pd—C (10% w/w, 0.2 g) was swirled under $H_2$ (7 atm) overnight. After evacuation of the hydrogen atmosphere, the mixture was filtered by syringe and the filtrate was concentrated to dryness. Then, MeOH (10 mL) and 1 M HCl (10 mL) were added sequentially and the reaction solution was stirred for 2 to 3 hours. After acidification, the solution was purified by centrifugal filtration (MWCO=3,000) and washed twice with deionized (DI) water. Finally, the concentrated solution in the centrifuge tube was freeze-dried, yielding the deprotected and acidified LPEI-Catechol conjugate L42 (0.43 g, 53%). $^1$H-NMR (400 MHz, $D_2O$, 22° C.): delta 6.70-7.60 (m, 53H, PhH), 5.13 (d, 8H, —$OCH_2Ph$ of protected catechol moiety), 2.80-3.90 (br, m, 1019H, H of LPEI), 2.36 (m, 8H, $CH_3CH_2CONH$—), 1.83 (m, 57H, $CH_3CH_2CONH$— and —$CH_3$).

Example 49

L43 was prepared by reaction of LPEI25 (0.3 g, 0.0274 mmol) with MTC-catechol (156 mg, 0.3 mmol) following the procedure of Example 48. A total of 21 catechol groups in the form of $H^a$ and $H^b$ were introduced, where the ratio $H^a$:$H^b$=18:3.

Example 50

B5 was prepared by reaction of BPEI25 (0.3 g, 0.03 mmol) with MTC-catechol (62.4 mg, 0.12 mmol) in dichloromethane following the general procedure of Example 48. A total of 5 catechol groups were introduced.

Example 51

B6 was prepared by reaction of BPEI25 (0.3 g, 0.03 mmol) with MTC-catechol (124.8 mg, 0.24 mmol) in dichloromethane following the general procedure of Example 48. A total of 12 catechol groups were introduced.

Example 52

Figure 2A:
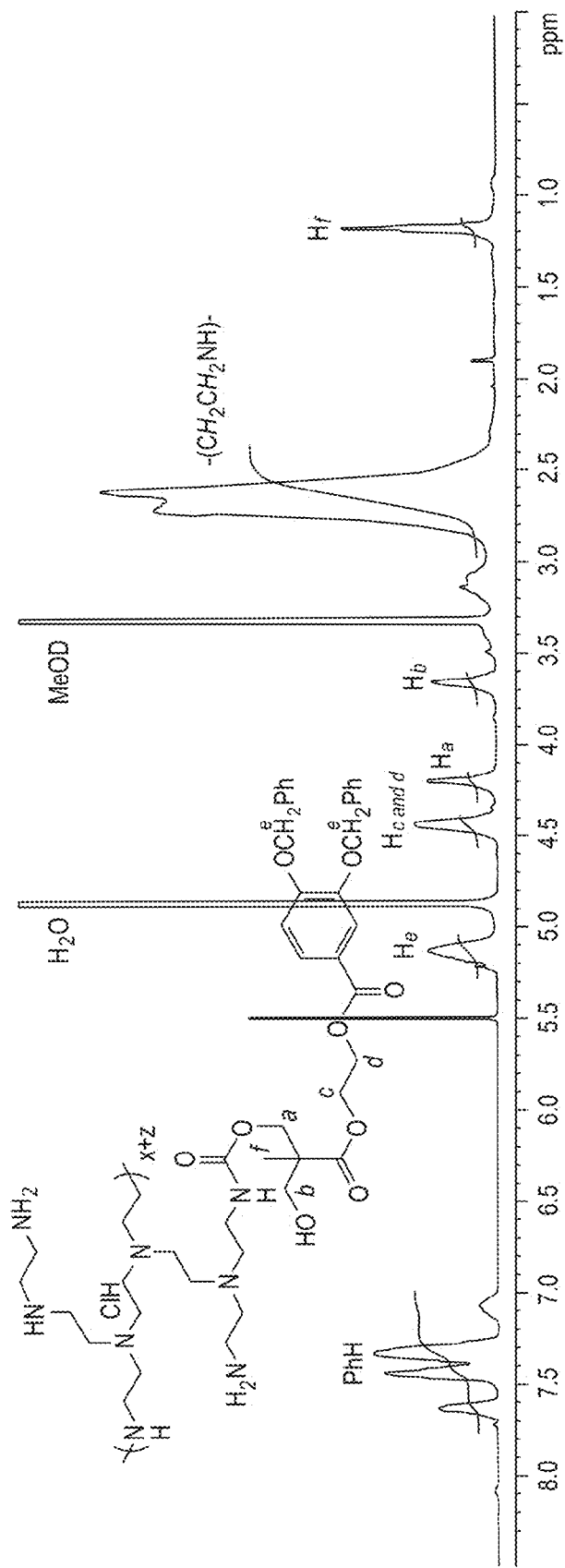
FIG. 2A is a $^1$H NMR spectra taken in MeOD of B7 (Example 52), a catechol modified BPEI25 comprising 20 catechol groups, before hydrogenolysis.
Figure 2B:
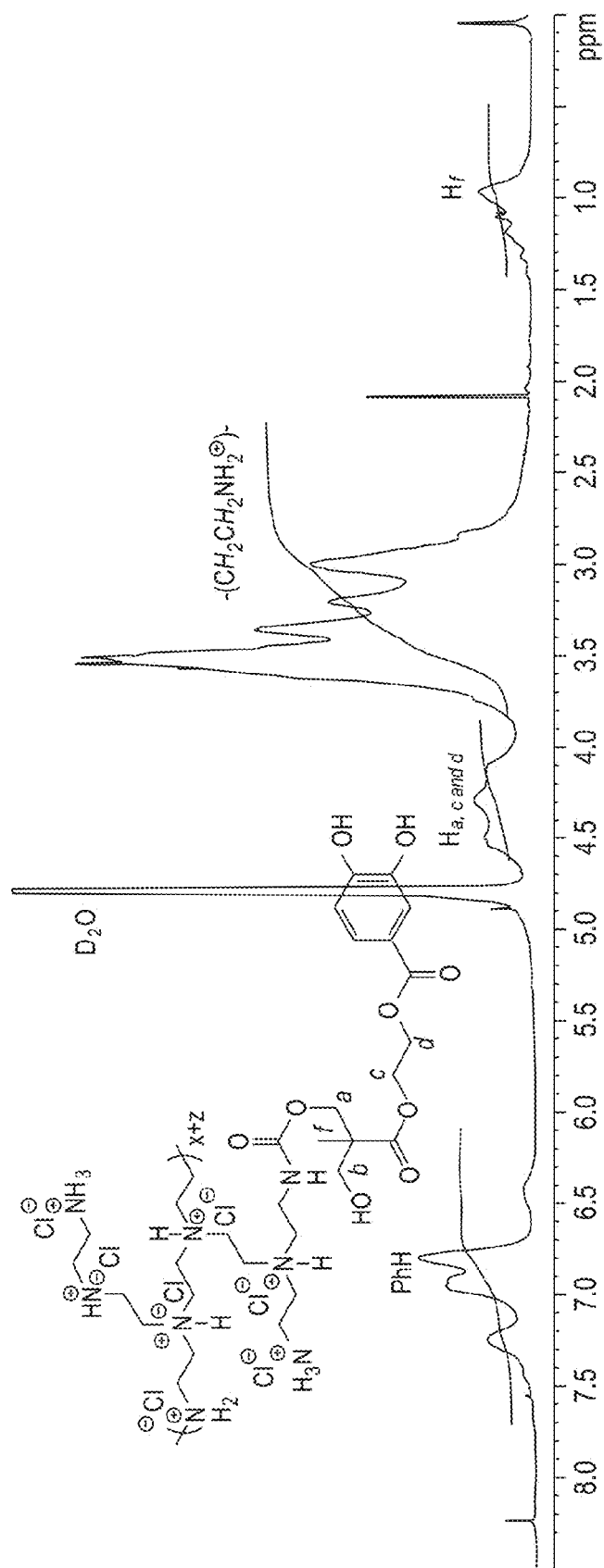
FIG. 2B is a $^1$H NMR spectra taken in $D_2O$ of B7 (Example 52), a catechol modified BPEI25 comprising 20 catechol groups, after hydrogenolysis and acidification.

B7 was prepared by reaction of BPEI25 (0.2 g, 0.02 mmol) with MTC-catechol (167 mg, 0.32 mmol) in dichloromethane following the general procedure of Example 48. A total of 20 catechol groups were introduced. FIG. 2A is a $^1$H NMR spectra taken in MeOD before hydrogenolysis. FIG. 2B is a $^1$H NMR spectra taken in $D_2O$ of B7 after hydrogenolysis and acidification.

Example 53

B8 was prepared by reaction of BPEI25 (0.2 g, 0.02 mmol) with MTC-catechol (10 catechol groups introduced) and MTC-PEG750 (4 PEG groups introduced) in dichloromethane following the general procedure of Example 48. MTC-Catechol (0.104 g, 0.2 mmmol) and MTC-PEG750 (0.093 g, 0.1 mmol) were dissolved in 2 mL of DCM, and the solution was added to BPEI25 (Mn 10 kDa, 0.25 g, 0.025 mmol) in 2 mL of DCM solution. The resulting reaction solution was stirred for 1 hour before being concentrated to dryness. Then, MeOH (7.5 mL), THF (7.5 mL) and Pd—C (0.2 g) were added to the residue, and the resulting mixture was swirled under $H_2$ (7 atm) overnight. Thus, the benzyl groups of catechol moieties were removed by hydrogenolysis. The reaction mixture was filtered and concentrated to dryness, and then 10 mL of methanol and 10 mL of 1 M HCl (aq.) were added and stirred for 1 hour. Finally, the mixture was purified by ultrafiltration in a Vivaspin 20 concentrator (MWCO=2 k, Sartorius AG, Goettingen, Germany), washed 3 times with de-ionized (DI) water, and freeze-dried to give the final product B8 (0.45 g, 70%). $^1$H-NMR (400 MHz, $D_2O$, 22° C.): delta 6.60-7.45 (m, br, 30H, PhH), 4.23 (m, br, 28H, —$CH_2$OC(O)NH—), 2.60-3.76 (m, br, 1230H, —$CH_2$OH and H of MTC-PEG750 and BPEI), 1.08 (m, 42H, —$CH_3$).

Dopamine Modified LPEI and BPEI

Example 54

L44 was prepared by reaction of LPEI25 0.3 g, 0.0274 mmol) with MTC-dopamine (177 mg, 0.6 mmol) in dioxane using the general procedure of Example 48 without hydrogenating the base polymer. A total of 5 catechol groups were introduced.

Example 55

B9 was prepared by reaction of BPEI25 (0.2 g, 0.02 mmol) with MTC-dopamine (177 mg, 0.6 mmol) in dichloromethane using the general procedure of Example 48 without hydrogenating the base polymer. A total of 10 catechol groups were introduced.

BPEI1.8 Conjugates with MTC-PUC2 and MTC-PUC12

Example 56

B10 was as-purchased BPEI1.8 (non-protonated).

Example 57

B11 was prepared by reaction of BPEI1.8 (0.315 g, 0.175 mmol) with MTC-PUC2 (113 mg, 0.35 mmol) in dichloromethane using the general procedure of Example 47. A total of 2 urea groups were introduced.

Example 58

B12 was prepared by reaction of BPEI1.8 (0.225 g, 0.125 mmol) with MTC-PUC2 (202 mg, 0.625 mmol) in dichloromethane using the general procedure of Example 47. A total of 5 urea groups were introduced.

Example 59

B13 was prepared by reaction of BPEI1.8 (0.36 g, 0.2 mmol) with MTC-OBn (50 mg, 0.2 mmol) in dichloromethane using the general procedure of Example 47. A total of 1 benzyl group was introduced.

Example 60

B14 was prepared by reaction of BPEI1.8 (0.36 g, 0.2 mmol) with MTC-PUC12 97.3 mg, 0.2 mmol) in dichloromethane using the general procedure of Example 47. A total of 1 urea group was introduced.

Examples 61 to 86

Oxidation studies of LPEI25 and BPEI25. The same protocol was followed except where noted below. The amount of $H_2O_2$ was also varied. Example 61 is representative. LPEI25 (0.219 g, 0.02 mmol, ethylenimine units (EI): 5.1 mmol) was put in a 20 mL of vial and DI-water (5 mL) was added. The mixture was heated to 85° C. under stirring. After a clear solution was obtained, $H_2O_2$ (30%, 52 microliters, 0.51 mmol) was added dropwise to the solution, and the solution was stirred overnight at 85° C. The reaction solution was then cooled to room temperature, transferred to a 15-ml centrifugal concentrator (MWCO=3,000), and washed with DI-water (3 times) prior to lyophilization, resulting in Example 61. For Examples 67-73, the reaction was carried out at room temperature. For Examples 74-81, 5 mL of 1 M HCl was added instead of 5 mL of DI-water to adjust to pH 2.3, and then the oxidation reaction was carried out at room temperature. For Examples 82-86, BPEI25 was used in the reaction instead of LPEI25, and the reaction was carried at room temperature.

Example 87

B15 was prepared by reacting BPEI25 (0.25 g, 0.025 mmol) with MTC-catechol (104 mg, 0.2 mmol) and MTC-PEG5k (Mn of PEG is 5,000, 129 mg, 0.025 mmol) in dichloromethane using the general procedure of Example 53. A total of 9 catechol groups and 1 PEG group (Mn=5000) were introduced. $^1$H-NMR (400 MHz, $D_2O$, 22° C.): delta 6.57-7.48 (m, br, 27H, PhH), 4.21 (m, br, 20H, —$CH_2$OC(O)NH—), 2.55-3.78 (m, br, 1405H, —$CH_2$OH and H of MTC-PEG5k and BPEI25), 1.04 (m, 30H, —$CH_3$).

Hemolysis

Fresh rat blood cells were subjected to 25× dilution with phosphate buffered saline (PBS) to obtain an approximate 4% v/v suspension for use in this experiment. Red blood cell suspension (300 microliters) was added to each tube containing an equal volume (300 microliters) of polymer sample solution in PBS (with final polymer concentrations ranging from 4.0-4000 mg/L). The tubes were then incubated at 37° C. for 1 hour before they were centrifuged at 1000×g for 5 min. Aliquots (100 microliters) of supernatant were transferred to each well of a 96-well plate and analyzed for hemoglobin release at 576 nm using a microplate reader (TECAN, Switzerland). Red blood cells suspension incubated with PBS was used as negative control. Absorbance of red blood cells lysed with 0.1% v/v Triton X-100 was used as the positive control and taken to be 100% hemolytic. Percentage of hemolysis was calculated using the following formula:

Hemolysis (%)=[(O.D.$_{576\,nm}$ of treated sample−O.D.$_{576\,nm}$ of negative control)/(O.D.$_{576\,nm}$ of positive control−O.D.$_{576\,nm}$ of negative control)]×100.

Data are expressed as mean±standard deviations of 4 replicates.

Figure 3:
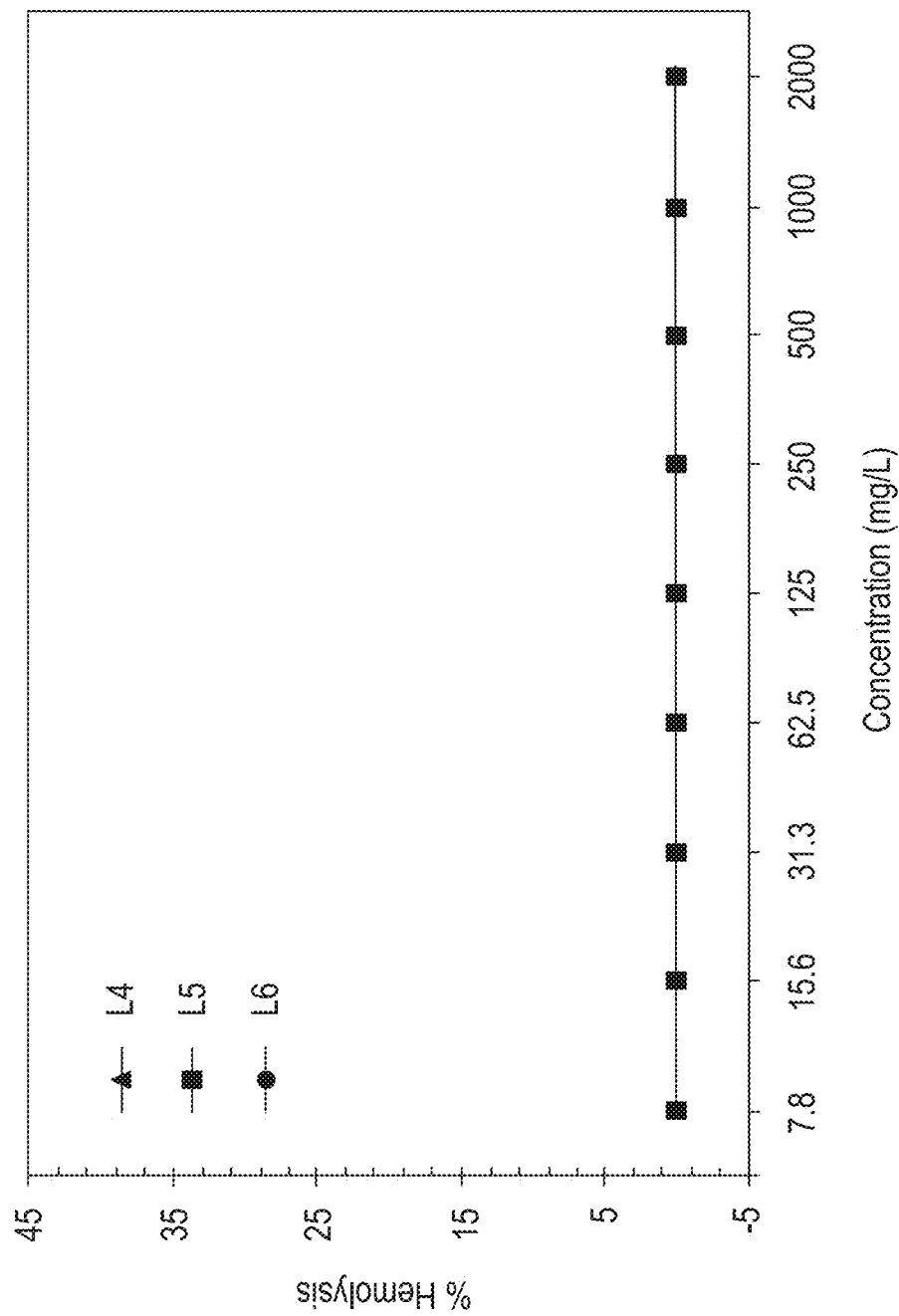
FIG. 3 is a graph showing the relative hemolytic properties of linear PEI samples L4-L6.
Figure 4:
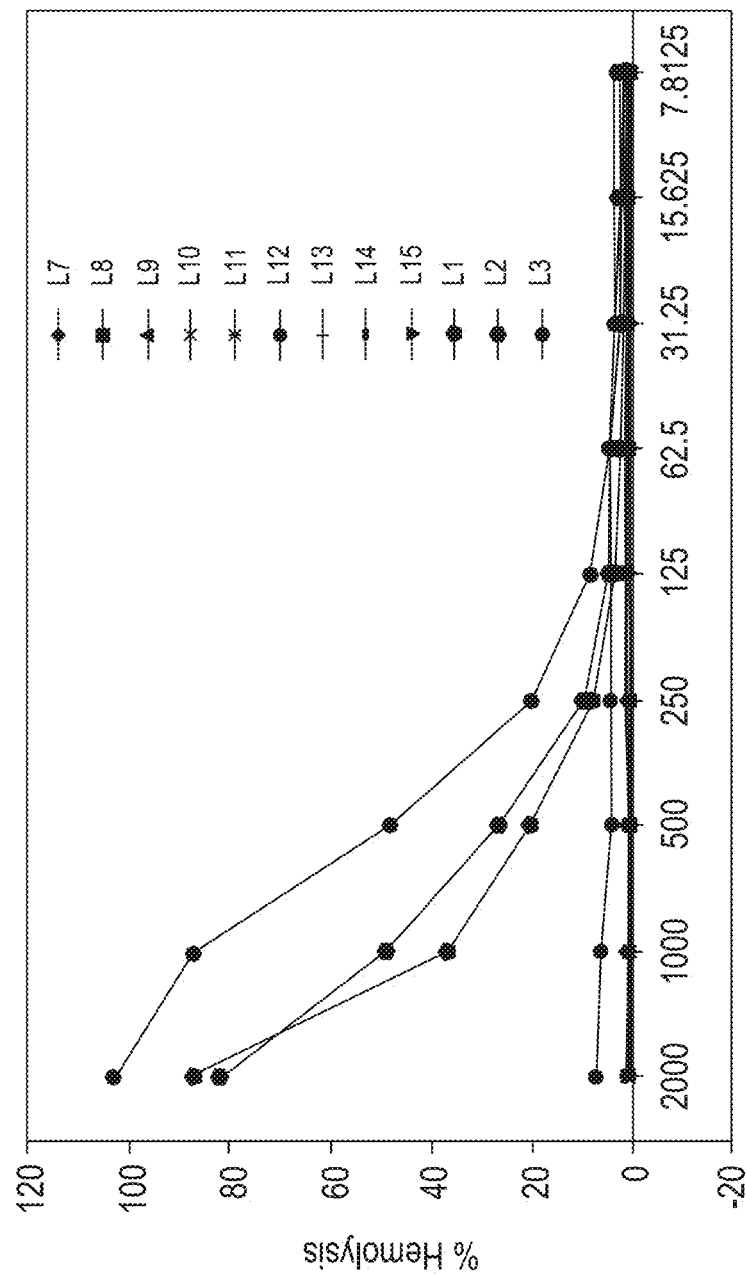
FIG. 4 is a graph showing the relative hemolytic properties of linear PEI samples L7-L15 compared to L1-L3.
Figure 5:
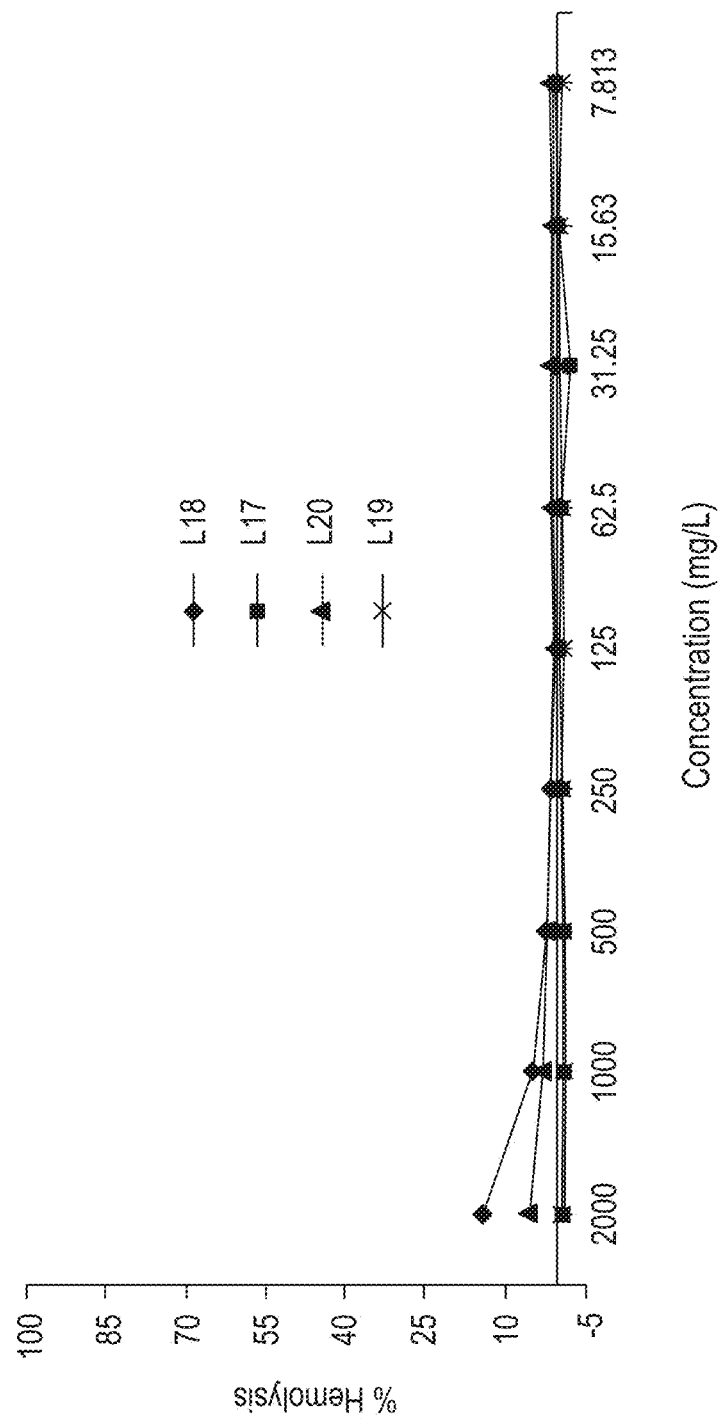
FIG. 5 is a graph showing the relative hemolysis properties of purified linear PEI samples L17 and L19, and neutralized linear PEI samples L18 and L20.
Figure 6:
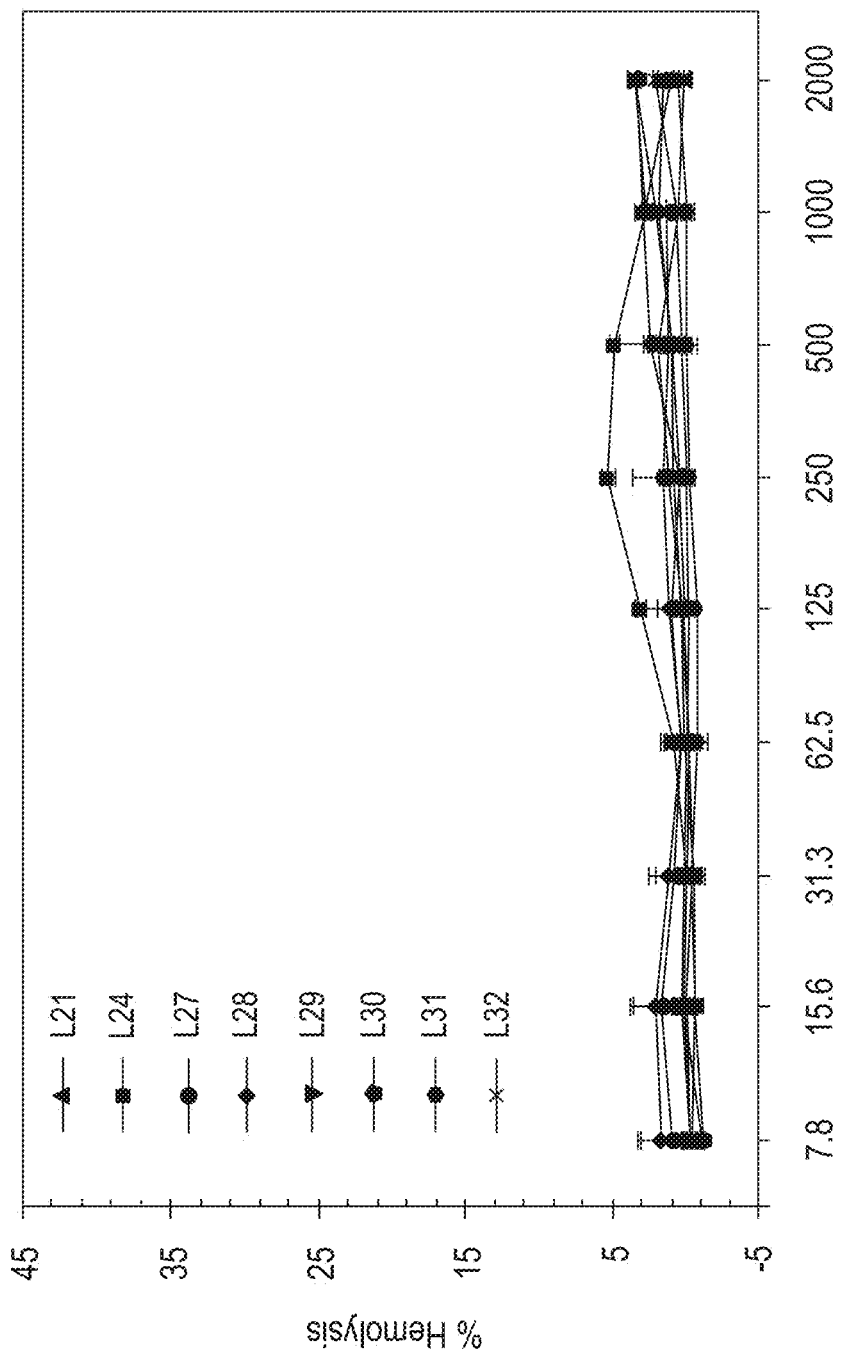
FIG. 6 is a graph showing the relative hemolysis properties of urea modified linear PEI samples L21 and L24, mannose modified linear PEI samples L27-L29, and TMC modified linear PEI samples L30-L32.
Figure 7:
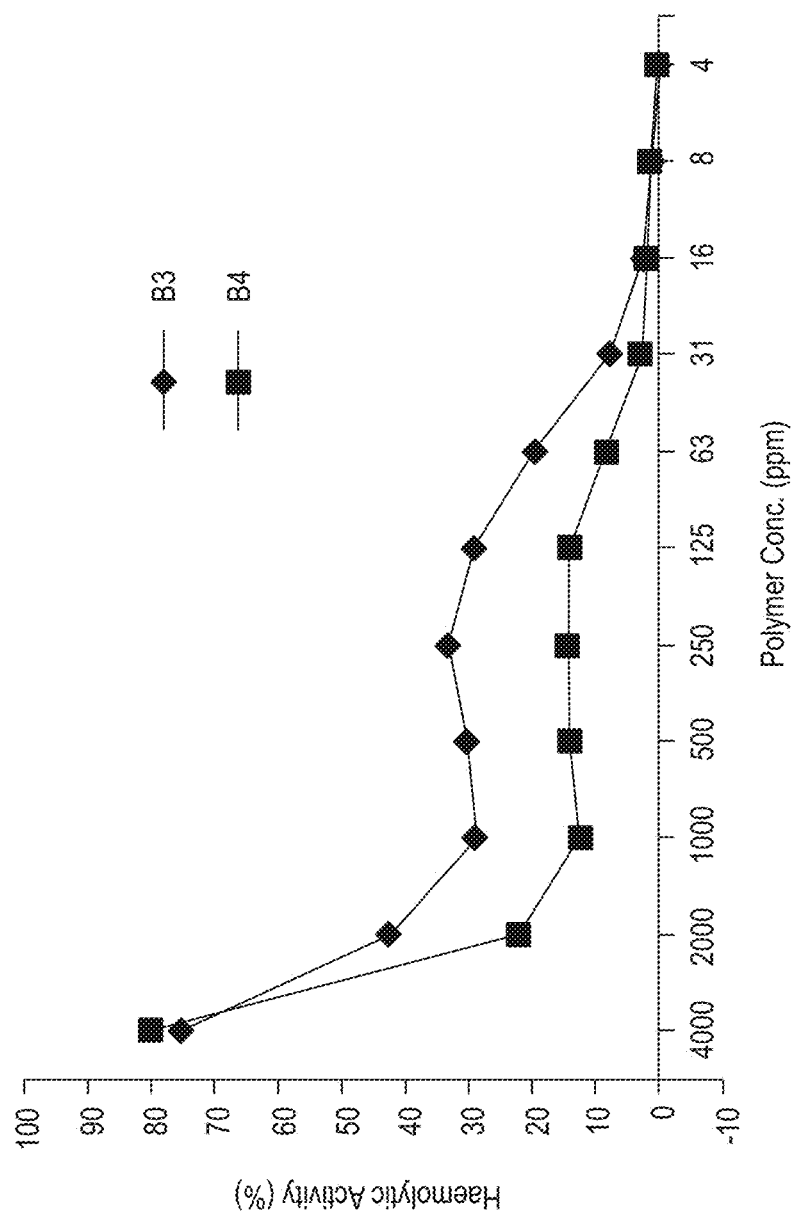
FIG. 7 is a graph showing the hemolysis behavior of urea-modified branched PEI samples B3 and B4.

FIG. 3 and FIG. 4 are graphs showing the % hemolysis of rat red blood cells as a function of concentration (mg/L) of as purchased linear PEI samples L1-L3, and treated linear PEI samples L4-L15 (see also Table 3 below). FIG. 5 is a graph showing the hemolysis behavior of purified linear PEI samples L17 and L19, and neutralized linear PEI samples L18 and L20 of Table 3. FIG. 6 is a graph showing the hemolysis behavior of urea modified linear PEI samples L21 and L24, mannose modified linear PEI samples L27-L29, and TMC modified linear PEI samples L30-L32. FIG. 7 is a graph showing hemolysis behavior of urea-modified branched PEI samples B3 and B4. The as-purchased linear PEI (basic form of the LPEI) was the most hemolytic of the samples. The acidified as-purchased LPEI and acidified modified LPEIs were essentially non-hemolytic at the MIC values.

Antimicrobial Activity
Minimal Inhibitory Concentration (MIC) Measurements

*Staphylococcus aureus* (*S. aureus*) (ATCC No. 6538), *Escherichia coli* (*E. coli*) (ATCC No. 25922), *Pseudomonas aeruginosa* (*P. aeruginosa*) (ATCC No. 9027), and *Candida albicans* (*C. albicans*, a fungus) (ATCC No. 10231) were re-constituted from the lyophilized form. Bacterial and fungal samples were cultured in Mueller Hinton II broth (MHB II) at 37° C. and room temperature (~22° C.), respectively, under constant shaking at 300 rpm.

The MICs of the polymers against tuberculosis (TB) mycobacteria (clinical samples 1348 and 1351, and H37Ra from ATCC) were measured using the broth microdilution method. 100 microliters of Middlebrook 7H9 broth containing a polymer at various concentrations was placed into each well of a 96-well tissue culture plate. An equal volume of bacterial suspension ($3\times10^5$ CFU/ml), where CFU means colony forming units, was added into each well. Prior to mixing, bacterial frozen stocks were defrosted, and cultured on Lowenstein-Jensen agar at 37° C. for 10 days. A freshly isolated colony was taken out and cultured in 4 mL of Middlebrook 7H9 broth containing 0.1% TWEEN 80 at 37° C. for 10 days. The bacterial culture was diluted using phosphate buffered saline (PBS, pH 7.4) to the concentration of McFarland 1 solution ($3\times10^8$ CFU/ml), which was further diluted by 100 times with Middlebrook 7H9 broth containing TWEEN 80 to achieve an initial loading of $3\times10^6$ CFU/ml. The 96-well plate was kept in an incubator at 37° C. for 10 days. The MIC was taken as the concentration of the antimicrobial polymer at which no microbial growth was observed with unaided eyes. Broth containing bacterial cells and broth alone were used as controls, and each test was carried out in 3 replicates.

The MICs of the polymers against other microbes were measured using the broth microdilution method. 100 microliters of MHB II containing a polymer at various concentrations was placed into each well of a 96-well tissue culture plate. An equal volume of bacterial suspension ($3\times10^5$ CFU/ml), where CFU means colony forming units, was added into each well. Prior to mixing, the bacterial sample was first inoculated overnight to enter its log growth phase. The concentration of bacterial solution was adjusted to give an initial optical density (O.D.) reading of approximately 0.07 at 600 nm wavelength on microplate reader (TECAN, Switzerland), which corresponds to the concentration of McFarland 1 solution ($3\times10^8$ CFU/ml). The bacterial solution was further diluted by 1000 times to achieve an initial loading of $3\times10^5$ CFU/ml. The 96-well plate was kept in an incubator at 37° C. under constant shaking of 300 rpm for 18 hours (bacteria, *S. aureus*, *E. coli*, *P. aeruginosa*) or 42 hours (fungi, *C. albicans*). The MIC was taken as the concentration of the antimicrobial polymer at which no microbial growth was observed with unaided eyes and microplate reader (TECAN, Switzerland) at the end of 18 hours incubation. Broth containing microbial cells alone was used as negative control, and each test was carried out in 6 replicates. Since the samples L1-L3 (as-purchased linear PEI) are not water soluble, 4 mg of each was first dissolved in 50 microliters of ethanol. The solution was then diluted to various concentrations using microbial culture media prior to testing.

Table 3 summarizes the polymer samples, their MICs and % hemolysis values of Examples 1-60 and 87. A lower MIC and a lower % hemolysis are desirable. When two tests were performed, each test result is listed. TB refers to tuberculosis *mycobacterium*.

TABLE 3

| Example | Name | Description | Solvent | Color | MIC (mg/L) E. coli | S. aureus | P. aeruginosa | C. albicans | TB (Clinical sample 1348) | TB (Clinical sample 1351) | TB (H37Ra, deactivated-not infectious) | % Hemolysis @ 2000 mg/L |
|---|---|---|---|---|---|---|---|---|---|---|---|---|
| 1 | L1 | LPEI2.5 As purchased | | white | 31.3 | 31.3 | 125 | 62.5 | | | | 88 |
| 2 | L2 | LPEI25 As purchased | | white | 31.3 | 31.3 | 125 | 62.5 | | | | 82 |
| 3 | L3 | LPEI250 As purchased | | white | 31.3 | 125 | 125 | 62.5 | | | | 105 |
| 4 | L4 | LPEI2.5 a) 80 C., 16 h, solvent b) MeOH/HCl | Dioxane | brown | 250 | 250 | >1000 | 31.3 | | | | <5 |
| 5 | L5 | LPEI25 a) 80 C., 16 h, solvent b) MeOH/HCl | Dioxane | brown | 62.5 | 62.5 | 1000 | 31.3 | | | | <5 |
| 6 | L6 | LPEI250 a) 80 C., 16 h, solvent b) MeOH/HCl | Dioxane | brown | 62.5 | 62.5 | 500 | 31.3 | | | | <5 |
| 7 | L7 | LPEI25 a) Heat in vacuum b) 85 C., 1-2 h, solvent c) MeOH/HCl | Chloroform | yellow | 62.5 | 15.6 | 62.5 | 125 | | | | <5 |
| 8 | L8 | LPEI25 a) Heat in vacuum b) MeOH/HCl | none | white | 62.5 | 15.6 | 62.5 | 125 | | | | <5 |
| 9 | L9 | LPEI25 a) Heat in vacuum b) 85 C., 1-2 h, solvent c) MeOH/HCl | THF | white | 62.5 | 15.6 | 62.5 | 125 | | | | <5 |
| 10 | L10 | LPEI25 a) Heat in vacuum b) Heat open air c) MeOH/HCl | | brown | 62.5 | 62.5 | 500 | 62.5 | | | | <5 |
| 11 | L11 | LPEI25 a) Heat in vacuum b) 85 C., 1-2 h, solvent c) MeOH/HCl | ACN | yellow | 31.3 | 31.3 | 125 | 62.5 | 250 | 500 | | <5 |
| 12 | L12 | LPEI25 a) Heat in vacuum b) MeOH/HCl | | white | 125 | 125 | 125 | 125 | | | | 8 |
| 13 | L13 | LPEI25 a) Heat in vacuum b) 85 C., 1-2 h, solvent c) MeOH/HCl | EtOAc | yellow | 31.3 | 31.3 | 125 | 62.5 | | | | <5 |
| 14 | L14 | LPEI25 a) MeOH/HCl | MeOH | white | 31.3 | 31.3, 15.6 | 62.5 | 62.5 | | | 8 | <5 |

TABLE 3-continued

| Example | Name | Description | Solvent | Color | E. coli | S. aureus | P. aeruginosa | C. albicans | TB (Clinical sample 1348) | TB (Clinical sample 1351) | TB (H37Ra, deactivated-not infectious) | % Hemolysis @ 2000 mg/L |
|---|---|---|---|---|---|---|---|---|---|---|---|---|
| 15 | L15 | LPEI25 a) Heat in vacuum b) 85 C., 1-2 h, solvent c) MeOH/HCl | MeOH | yellow | 31.3 | 15.6 | 62.5 | 62.5 | | | | <5 |
| 16 | L16 | LPEI25 a) Heat in vacuum b) 85 C., 1-2 h, solvent c) MeOH/HCl | Dioxane | brown | 125 | 125 | >1000 | 62.5 | | | | |
| 17 | L17 | L14 washed with DI water | | white | 62.5, 31.3 | 15.6 | 31.3, 62.5 | 62.5 | | | 8 | <5 |
| 18 | L18 | L14 neutralized to pH 7.2, washed with DI water | | white | 62.5, 31.3 | 7.8 | 31.3 | 62.5 | | | 8 | 15 |
| 19 | L19 | L15 washed with DI water | | white | 62.5, 31.3 | 62.5, 15.6 | 62.5, 31.3 | 62.5 | | | | <5 |
| 20 | L20 | L15 neutralized to pH 7.0, washed with DI water | | white | 62.5, 15.6 | 7.8 | 62.5, 31.3 | 31.3 | | | | <5 |
| 21 | L21 | LPEI25/ MTC-PUC12 conjugate, z = 10 | Dioxane | red | 31.3 | 15.6 | 31.3, 15.6 | 125, 15.6 | 62.5 | | 15.6 | <5 |
| 22 | L22 | L21 washed with DI water | | red | 62.5, 31.3 | 7.8, 15.6 | 31.3, 15.6 | 31.3, 15.6 | | | 31.3 | 18 |
| 23 | L23 | L21 neutralized to pH 7.2 | | yellow | 62.5, 15.6 | 15.6, 15.6 | 31.3, 15.6 | 31.3, 15.6 | | | 31.3 | 25 |
| 24 | L24 | LPEI25/ MTC-PUC12 conjugate, z = 16 | Dioxane | red | 62.5, 31.3 | 15.6, 7.8 | 31.3 | 125, 15.6 | | | 15.6, 8.0 | 25 |
| 25 | L25 | L24 washed with DI water | | red | 31.3 | 7.8 | | 15.6 | | | 7.8, 8.0 | 40 |
| 26 | L26 | L24 neutralized to pH 7.2 | | yellow | 15.6 | 7.8 | | 15.6 | | | 7.8, 8.0 | 78 |
| 27 | L27 | LPEI25/ MTC-IPMAN conjugate, z = 8 | Dioxane | brown | 31.3 | 31.3 | 250 | 62.5 | | | | <5 |
| 28 | L28 | LPEI25/ MTC-IPMAN conjugate, z = 14 | Dioxane | brown | 62.5 | 31.3 | 250 | 62.5 | | | | <5 |
| 29 | L29 | LPEI25/ MTC-IPMAN conjugate, z = 26 | Dioxane | brown | 125 | 62.5 | 500 | 125 | | | | <5 |
| 30 | L30 | LPEI25/TMC conjugate z = 6 | Dioxane | brown | 125 | 62.5 | 250 | 62.5 | | | | <5 |
| 31 | L31 | LPEI25/TMC conjugate z = 1 | Dioxane | brown | >500 | 500 | >500 | 62.5 | | | | <5 |

TABLE 3-continued

| Example | Name | Description | Solvent | Color | E. coli | S. aureus | P. aeruginosa | C. albicans | TB (Clinical sample 1348) | TB (Clinical sample 1351) | TB (H37Ra, deactivated-not infectious) | % Hemolysis @ 2000 mg/L |
|---|---|---|---|---|---|---|---|---|---|---|---|---|
| 32 | L32 | LPEI25/TMC conjugate, z = 16 | Dioxane | brown | 500 | 250 | >500 | 125 | | | | <5 |
| 33 | L33 | LPEI25/MTC-PUC8 conjugate, z = 10 a) 80 C., 16 h, solvent b) MeOH/HCl c) precipitate in THF | Chloroform | Light yellow | 31.3 | 15.6 | | 31.3 | | | 8.0 | ~72% |
| 34 | L34 | L33 washed with DI water | | Light yellow | 15.6 | 7.8 | | 31.3 | | | 8.0 | ~78% |
| 35 | L35 | L33 neutralized to pH 7.2 | | Light yellow | 15.6 | 7.8 | | 31.3 | | | 8.0 | ~85% |
| 36 | L36 | LPEI25/MTC-OBn conjugate, z = 12 a) 80 C., 16 h, solvent b) MeOH/HCl | Dioxane | red | 250 | 62.5 | | 125 | | | 8.0 | <5 |
| 37 | L37 | LPEI25/MTC-OBn conjugate, z = 12 a) 80 C., 16 h b) MeOH/HCl c) washed with DI water neutralized to pH 7.2 | Dioxane | yellow | 250 | 62.5 | | 62.5 | | | 8.0 | <5 |
| 38 | L38 | L27 washed with DI water | | brown | 31.3 | 15.6 | 125 | 62.5 | | | | |
| 39 | L39 | L27 neutralized to pH 7.2 | | yellow | 31.3 | 15.6 | 125 | 62.5 | | | | |
| 40 | L40 | L28 washed with DI water | | brown | 62.5 | 62.5 | 1000 | 62.5 | | | | |
| 41 | L41 | L28 neutralized to pH 7.2 | | yellow | 62.5 | 62.5 | 500 | 62.5 | | | | |
| 42 | PC1 | ROP of MTC-BnCl, cholesterol as initiator, TMA, end-capped with AcCl, DP 20 | DCM | white | | | | | >500 mg/L | >500 mg/L | | |
| 43 | PC2 | ROP of MTC-BnCl, cholesterol-(CH2)3OH initiator, TMA, end-capped with AcCl, DP 11 | DCM | white | | | | | >500 mg/L | >500 mg/L | | |
| 44 | B1 | BPEI25/ MTC-IPMAN conjugate, 67 mannose groups | DCM | light yellow | | | | | >500 mg/L | >500 mg/L | | |
| 45 | B2 | BPEI25/ MTC-PUC8 conjugate, z = 16 | DCM | light yellow | 125 | 31.3 | 62.5 | | | | 32 | 22 |
| 46 | B3 | BPEI25/ MTC-PUC8 conjugate, z = 33 | DCM | light yellow | 62.5 | 31.3 | 62.5 | | | | 32 | 42 |

TABLE 3-continued

| Example | Name | Description | Solvent | Color | E. coli | S. aureus | P. aeruginosa | C. albicans | TB (Clinical sample 1348) | TB (Clinical sample 1351) | TB (H37Ra, deactivated-not infectious) | % Hemolysis @ 2000 mg/L |
|---|---|---|---|---|---|---|---|---|---|---|---|---|
| 47 | B4 | BPEI1.8/MTC-PUC2 conjugate, z = 1 | DCM | light yellow | 250 | 31.3 | | 7.8 | | | 4.0 | 7 |
| 48 | L42 | LPEI25/MTC-Catechol conjugate, 11 catechol groups | DCM | light yellow | | 15.6 | 125 | 31.3 | | | | |
| 49 | L43 | LPEI25/MTC-Catechol conjugate, 21 catechol groups | Dioxane | light yellow | | | | | | | | |
| 50 | B5 | BPEI25/MTC-Catechol conjugate, 5 catechol groups | DCM | light yellow | | 15.6 | 125 | 31.3 | | | | |
| 51 | B6 | BPEI25/MTC-Catechol conjugate, 12 catechol groups | DCM | light yellow | | | | 31.3 | | | | |
| 52 | B7 | BPEI25/MTC-Catechol conjugate, 20 catechol groups | DCM | brown | 1000 | 31.3 | | 15.6, 500 | | | | |
| 53 | B8 | BPEI25/MTC-Catechol and MTC-PEG750 conjugate, 10 catechol groups, 4 for MTC-PEG750 | DCM | white | | | | 125 | | | | |
| 54 | L44 | LPEI25/MTC-Dopamine conjugate, 5 catechol groups | DCM | Light yellow | >1000 | 125 | | 31.3 | | | | |
| 55 | B9 | BPEI1.8/MTC-Dopamine conjugate, 10 catechol groups | DCM | Light yellow | 1000 | 15.6 | | 7.8 | | | | |
| 56 | B10 | BPEI1.8 (as purchased) | | | | | | | | | 256.0 | |
| 57 | B11 | BPEI1.8/MTC-PUC2 conjugate, 2 urea groups | DCM | Light yellow | 1000 | 31.3 | | 15.6 | | | | 6.0 at 1000 mg/L |
| 58 | B12 | BPEI1.8/MTC-PUC2 conjugate, 5 urea groups | DCM | Light yellow | >1000 | 125 | | 31.3 | | | | 8.5 at 1000 mg/L |
| 59 | B13 | BPEI1.8/MTC-OBn conjugate, 1 benzyl group | DCM | Light yellow | 1000 | 15.6 | | 7.8 | | | | 2.3 at 1000 mg/L |
| 60 | B14 | BPEI1.8/MTC-PUC12 conjugate, 1 urea group | DCM | Light yellow | 62.5 | 7.8 | | 15.6 | | | 16.0 | 119 at 1000 mg/L |
| 87 | B15 | BPEI25/MTC-Catechol and MTC-PEG750 conjugate, 9 catechol groups, 1 for MTC-PEG5k | DCM | white | | | | 62.5 | | | | |

Cationic linear polyethylenimines LPEI25 (Example 14, L14) and LPEI25 conjugates having 10 urea groups (Example 21, L21) and 16 urea groups (Example 24, L24) were highly active against the TB mycobacterium and the other microbes, though none of the samples contained any quaternary amine groups. L18, L21 and L24 also exhibited low hemolysis (<5% at concentration of 2000 mg/L). Purification of each sample by washing the sample with DI water (Examples 17, 22 and 25, respectively) or neutralizing each sample using NaOH to a pH of 7.2 (Examples 18, 23 and 26, respectively) resulted in similar activity against the microbes and increased (but acceptable) levels of hemolysis (25% or less at 2000 mg/L). LPEI25 modified with MTC-IPMAN (Examples 27-29) or TMC (Examples 30-32) displayed borderline activity against *P. aeruginosa* compared to the urea modified LPEI25 samples, and therefore were not tested against TB.

The branched polyethylenimine (BPEI25) modified with urea groups (Examples 45-47, B2-B4, respectively) were also active against TB and the other microbes. Hemolysis levels for B2 and B3 were 22% and 42%, respectively, at 2000 mg/L. These values are higher than the linear polyethylenimines samples, yet still acceptable. B4, which was prepared from BPEI1.8 and MTC-PUC2, was non-hemolytic (7% at 2000 mg/L). B4 was also highly active against the fungus *C. albicans* (7.8 mg/L) and against the TB mycobacterium H37Ra (4.0 mg/L). Mannose modified branched polyethylenimine (Example 35, B1) and cationic polycarbonates comprising quaternary amine groups (Example 33, PC1 and Example 34, PC2) were not active against the TB mycobacterium.

Mouse Intravenous LD50

Intravenous (IV) LD50 values were determined using female Balb/c mice (6-7 weeks old, 18-22 g) according to the Up-and-Down-Procedure described in the Organisation for Economic Cooperation and Development Guideline for the Testing of Chemicals (OECD 425). The animals were allowed to acclimatize for 5 days and then randomly distributed into groups. Polymers were dissolved in sterilized saline and administered via intravenous injection (injection volume: 100 microliters). Polymer solution was firstly given to one mouse at a dose of 17.6 mg/kg. If the first mouse survived after 48 hours, two more mice were further used for the test. After injection, all the animals were observed every 30 minutes for the first 4 hours and daily thereafter, for a total of 14 days. The second dose at 56 mg/kg was given. If the mice survived the dose of 56 mg/kg, the third dose at 176 mg/kg was given. If the mice did not survive, the test was repeated on live mice using a first dose of 17.5 mg/kg and a second dose of 5.6 mg/kg was given. LD50 was determined using the maximum likelihood method. As-purchased LPEI25 was not tested for LD50 as it is not water soluble. If ethanol were used to dissolve as-purchased LPEI25 for injection, the ethanol could easily kill the mice. Thus, it would not give an accurate LD50 value.

Table 4 lists the LD50 values obtained for two samples L5 and L21. Mouse intravenous LD50 values of other commercially available compounds are shown for comparison. The data were obtained at the designated sources.

TABLE 4

| Example | Name | Description | Mouse Intravenous LD50 (mg/kg) | Source |
|---|---|---|---|---|
| 5 | L5 | LPEI25 a) 80 C., 16 h, dioxane b) MeOH/HCl | 98.2 | |
| 21 | L21 | LPEI25/MTC-PUC12 conjugate, dioxane, z = 10 | 31.5 | |
| | | Ethambutol (TB drug) | 240 | National Institute of Health (NIH), US |
| | | Rifampin (TB drug) | 260 | NIH |
| | | Isoniazid (TB drug) | 149 | NIH |
| | | Codeine (pain medication) | 54 | NIH |
| | | Caffeine (beverages) | 62 | NIH |
| | | Nicotine (tobacco products) | 0.3 | NIH |
| | | Doxorubicin (Cancer Drug) | 10 | NIH |
| | | Methotrexate (Cancer Drug) | 65 | NIH |

Polymer Coating on Contact Lens and PET Surfaces

Contact lens (Air Optics, Singapore) and poly(ethylene terephthalate) (PET) materials were punched into discs having a diameter of 4 mm. Before coating, contact lens surfaces were washed with phosphate buffered saline (PBS) three times, and PET surfaces were thoroughly cleaned with deionized water in a sonication bath and dried with nitrogen flow. The surfaces were then soaked for 4 hours with gentle shaking at room temperature in a Tris-buffered saline (10 mM, pH 8.5) containing the catechol modified LPEI25 or BPEI25 polymers at the following concentrations (L42: 22.6 g/L, L43: 41.6 g/L, B5: 21.6 g/L, B6: 29.1 g/L, B7: 48.4 g/L). The treated surfaces were then rinsed three times with phosphate-buffered saline (PBS) and dried with nitrogen flow. These polymer-treated surfaces were used immediately after preparation. The catechol modified BPEI25 (B5, B6 and B7) solutions were colorless, but the catechol modified LPEI25 (L42 and L43) solutions were slightly pinkish. However, the treated contact lens and PET surfaces coated with LPEI25 or BPEI25 were transparent and showed no significant difference in appearance compared with the untreated surfaces.

*C. albicans* Biofilm Formation and *E. coli* Attachment on Surfaces

Yeast *C. albicans* was grown in yeast mould broth (YMB) at room temperature overnight to reach mid-logarithmic growth phase. The concentration of yeast was adjusted by obtaining an optical density (O.D.) reading of 0.07 at a wavelength of 600 nm by a microplate reader (TECAN, Switzerland). The yeast cells were then seeded on untreated and polymer-treated contact lens surfaces and incubated for 4 hours in a 96-well plated at room temperature. Following 4 hours of incubation, non-adherent cells in YMB were removed. The contact lens surfaces were washed three times with sterile PBS, and fresh YMB was added. The plate was incubated for 48 hours to allow for *C. albicans* biofilm formation.

Gram-negative bacteria *E. coli* ($10^5$ cells/mL, 10 microliters) were seeded on the untreated and polymer-treated PET surfaces, followed by incubation at 37° C. for 24 hours before further tests.

LIVE/DEAD Microbial Viability Assay

To visualize the viable yeast and bacterial cells on the untreated and polymer-treated contact lens and PET surfaces, a LIVE/DEAD Baclight bacterial viability kit (L-7012, Invitrogen) with two staining agents was used. Propidium iodide, a red-nucleic acid staining agent, was used to label dead bacterial cells by penetrating damaged cell membrane. Meanwhile, SYTO® 9, a green-fluorescent nucleic acid staining agent, was used to label both live and dead microbes by penetrating cells with either intact or damaged membrane. After a 48 hour incubation of C. albicans on a contact lens surface and 24 hour incubation of E. coli on a PET surface, the surfaces were soaked in a dye solution (5.01 μM of SYTO and 30 μM of propidium iodide in PBS) at room temperature in the dark for 15 minutes. The stained microbes were observed using an oil immersed 63× objective lens of a Zeiss LSM 5 DUO laser scanning confocal microscope (Germany). The number of bacterial cells in the images was analyzed by the open-source software ImageJ (Fiji).

Antifungal Surface Results

Figure 8:
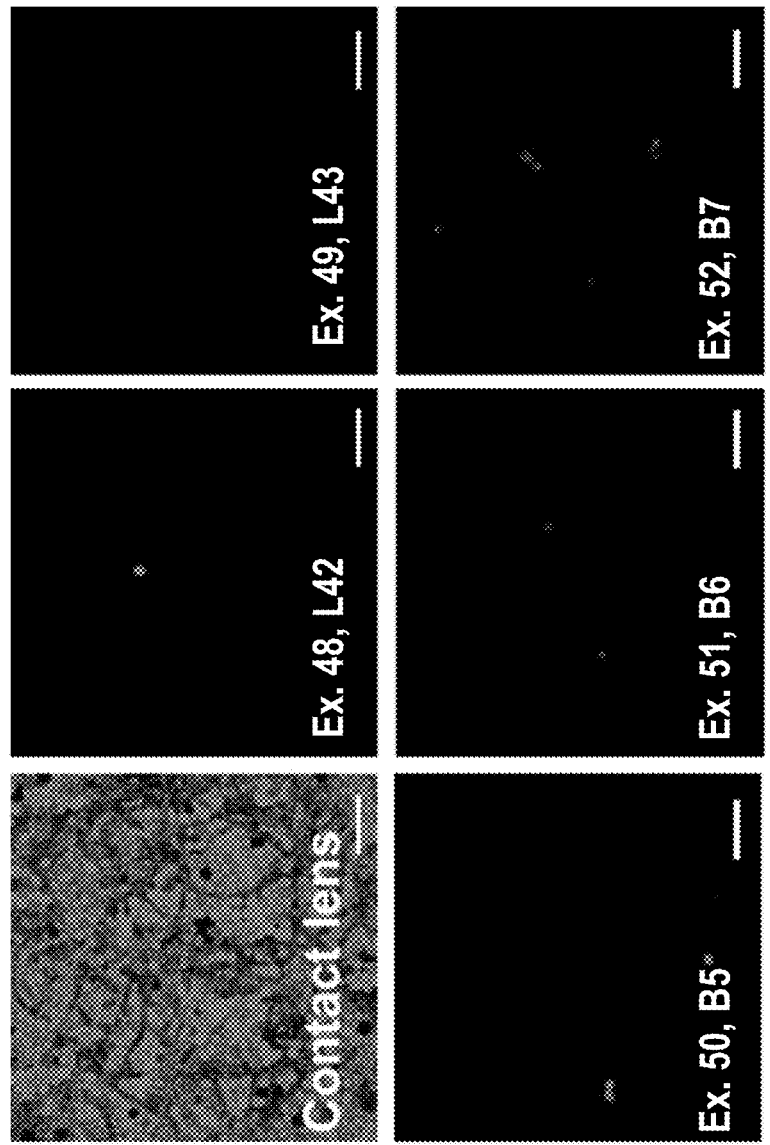
FIG. 8 is a series of LIVE/DEAD cell staining images after incubation with *Candida albicans* for two days of an untreated contact lens and contact lens surface treated with catechol-modified LPEI25 and BPEI25 samples L42 (Example 48), L43 (Example 49), B5 (Example 50), B6 (Example 51), and B7 (Example 52).

Since fungal keratitis results in perforation requiring keratoplasty more often than bacterial keratitis, C. albicans (a typical fungus) was used in this study to test the antimicrobial and antifouling activities of contact lens surface. The contact lens material was a silicone hydrogel material consisting of 67% lotrafilcon B and 33% water. FIG. 8 shows LIVE/DEAD staining results for an untreated contact lens, L42 (Example 48), L43 (Example 49), B5 (Example 50), B6 (Example 51), and B7 (Example 52). The entire surface of the untreated contact lens was almost fully covered by C. albicans after incubation with C. albicans for two days. A mixture of yeast and filamentous cell (hyphae) was found. The hyphal form has been reported to be more virulent and responsible for tissue invasion. By comparison, only several round yeast cells and no hyphae formation were observed on surfaces treated with catechol-modified LPEI25 and catechol-modified BPEI25 surfaces. The LIVE/DEAD fungus staining results also indicated no apparent difference in the antifungal properties based on numbers of catechol moieties of the cationic polyamines.

Figure 9:
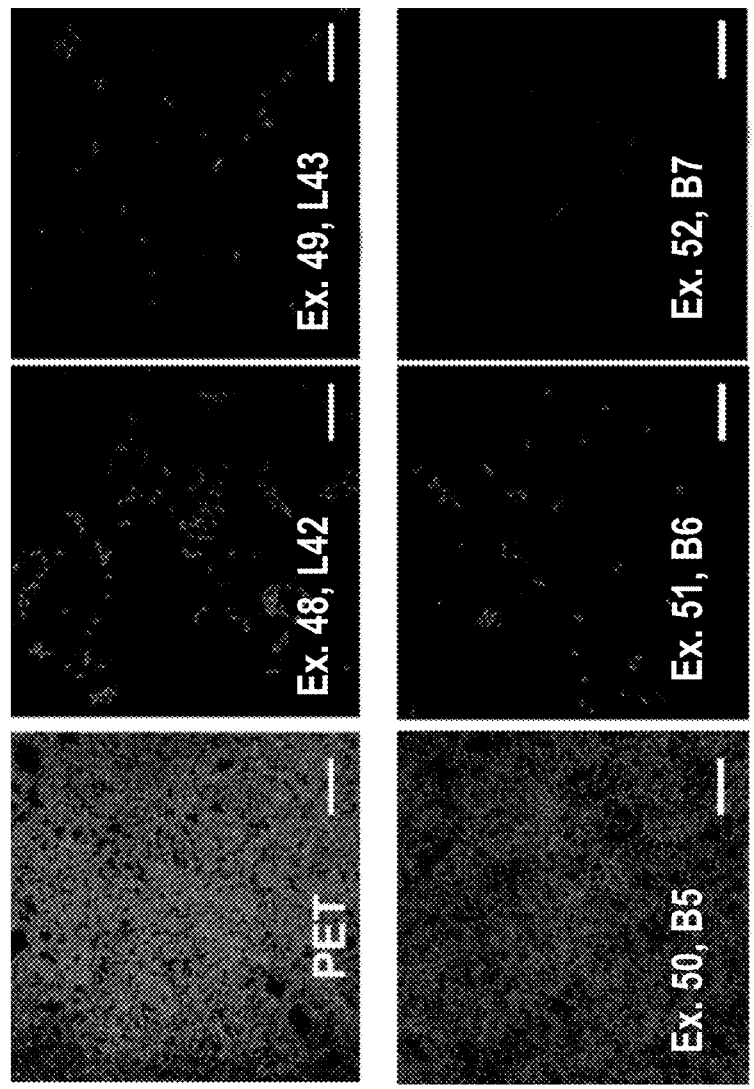
FIG. 9 is a series of LIVE/DEAD cell staining images after incubation with *E. coli* for 24 hours of untreated PET and PET surfaces treated with catechol-modified LPEI25 and BPEI25 samples L42 (Example 48), L43 (Example 49), B5 (Example 50), B6 (Example 51), and B7 (Example 52).

PET, as a common material of beverage and food containers, has been reported to be an ideal surface for E. coli adhesion. Bacterial biofilm can develop on the contaminated PET surface. This biofilm can act as a reservoir of pathogens and exhibit resistance to antimicrobial treatment. In this study, the LIVE/DEAD cell staining results shown in FIG. 9 for "PET" (untreated poly(ethylene terephthalate)), L42 (Example 48), L43 (Example 49), B5 (Example 50), B6 (Example 51), and B7 (Example 52) confirmed that PET has a favorable surface for E. coli cell adhesion. However, much fewer E. coli cells were found on the surfaces that were coated with catechol-modified LPEI25 compared to catechol-modified BPEI25 treated surfaces. In particular, the surface coated with L43, which had more catechol moieties than L42 possessed stronger antibacterial activity, and the number of E. coli cells attached on the L43-coated surface was reduced by about 99% as compared to the untreated PET surface. The catechol-modified BPEI25 coated surface also showed the same trend that more catechol moieties led to fewer E. coli cells on the PET surface. This could be due to enhanced adhesion of polymer to the PET surface as the content of catechol in the polymer increased. The B7 treated PET surface had the best antibacterial activity, having the fewest number of E. coli cells. For this sample, the reduction of bacterial cells was more than 99.9%.

Figure 10:
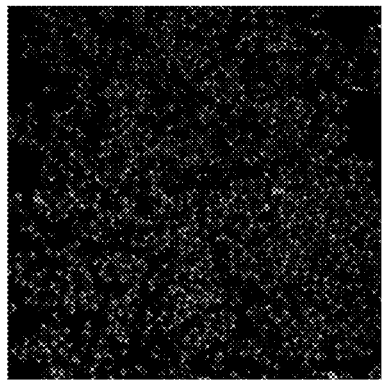
FIG. 10 is a series of LIVE/DEAD cell staining images after incubation with *Candida albicans* for two days of an untreated contact lens and contact lens surface treated with catechol-modified LPEI25 and BPEI25 samples B5 (Example 50), B6 (Example 51), B7 (Example 52), and B8 (Example 53).
Figure 10:
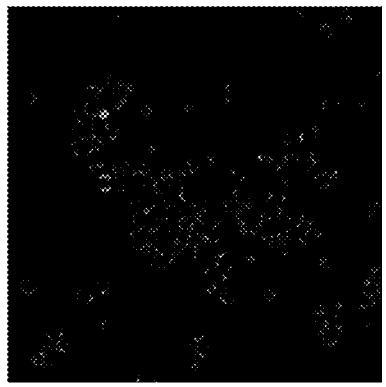
Figure 10:
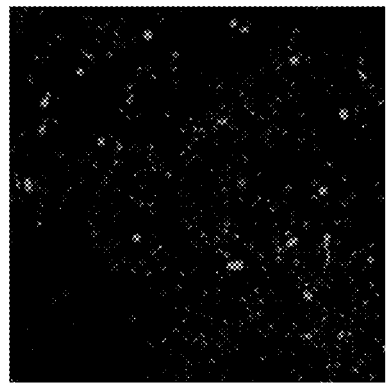
Figure 10:
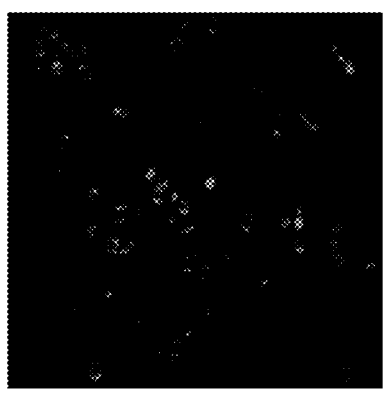
Figure 10:

In a similar protocol, B5, B6, B7 and B8 were coated onto the contact lens except that the polymer concentration was 1M (B5: 11.6 g/L, B6: 13.9, B7: 16.7 g/L, B8: 17.8 g/L) and the Tris-buffered saline pH value was 8.0. The catechol and PEG750 modified BPEI25 (B8) solution was colorless, and the contact lens (CL) material coated with B8 was transparent. FIG. 10 shows the LIVE/DEAD staining results for this series. B8 showed more activity against the C. albicans than B5, B6, and B7. Optical density (OD) values at 490-600 nm of the final films are listed below in Table 5. A lower OD indicates higher activity against C. albicans biofilm growth. In a separate experiment, the contact lens material was coated with B15 (Example 87) at a concentration of 1M and Tris-buffered saline pH=8.0 (not shown in FIG. 10). The B15 coated lens material, which had the lowest OD reading, was the most effective in inhibiting C. albicans growth.

TABLE 5

| Example | Contact Lens Treatment | OD (490-600 nm) |
|---|---|---|
|  | Untreated | 0.2978 |
| 51 | B5 | 0.0662 |
| 52 | B6 | 0.0339 |
| 53 | B7 | 0.0491 |
| 54 | B8 | 0.0545 |
| 87 | B15 | 0.0081 |

Static Contact Angle

Figure 11:
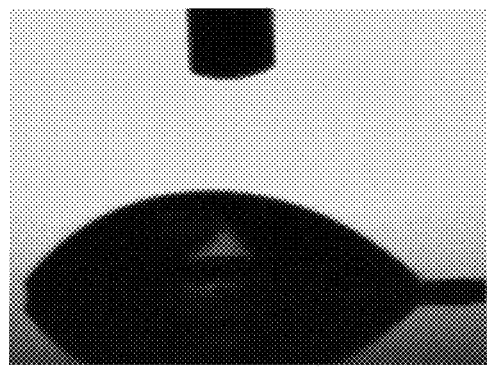
FIG. 11 is a series of static contact angle measurements of an untreated contact lens and contact lens surface treated with catechol-modified BPEI25 samples B5 (Example 50), B6 (Example 51), and B7 (Example 52).
Figure 11:
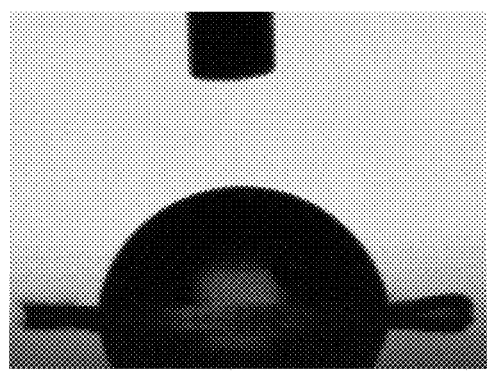
Figure 11:
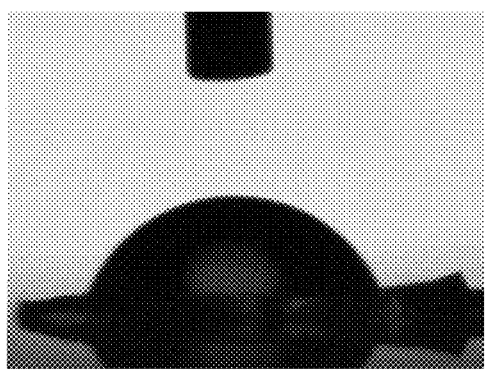
Figure 11:
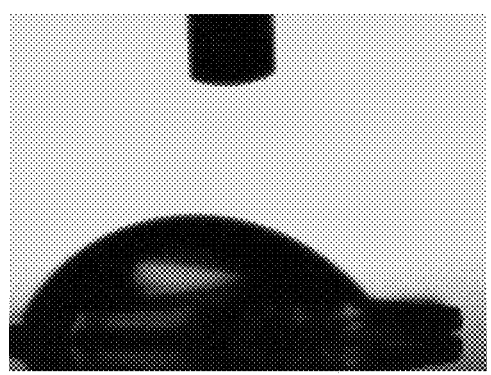

The static contact angles on uncoated and polymer-coated contact lens surfaces treated with different polymers at 1 mM for 4 hours were measured by an OCA30 contact angle measuring devise (Future Digital Scientific Corp., U.S.A.). DI water (20 microliters) was used for the measurements. All samples were analyzed in triplicates. FIG. 11 shows the static contact angle data for B5, B6, and B7 presented as mean±SD. Contact angle increased after polymer coating. Increasing catechol content from B5 to B7 led to a slightly reduced contact angle. The static contact angle for B15 was 66.1°±2.5° (not shown in FIG. 11).

Summary of Antimicrobial Results

Broad spectrum antimicrobial activity was observed with cationic linear and branched polyethylenimines comprising N-acylated ethylenimine units and positive-charged protonated ethylenimine units. In some instances, the cationic polyamines displayed high activity against a TB mycobacterium and other bacteria and were non-hemolytic at concentrations of 2000 mg/L without employing quaternary amine groups. The TB active cationic polyamines are soluble in water and are not crosslinked, making them attractive as injectable and aerosol delivered drugs. Mouse intravenous LD50 values for two samples were in a range corresponding to other commercially available drugs. Contact lens and PET surfaces treated with cationic polyamines comprising a catechol moiety were effective in inhibiting biofilms formed by C. albicans and E. coli.

Results of Hydrogen Peroxide Oxidation of LPEI25 and BPEI25

Figure 12:
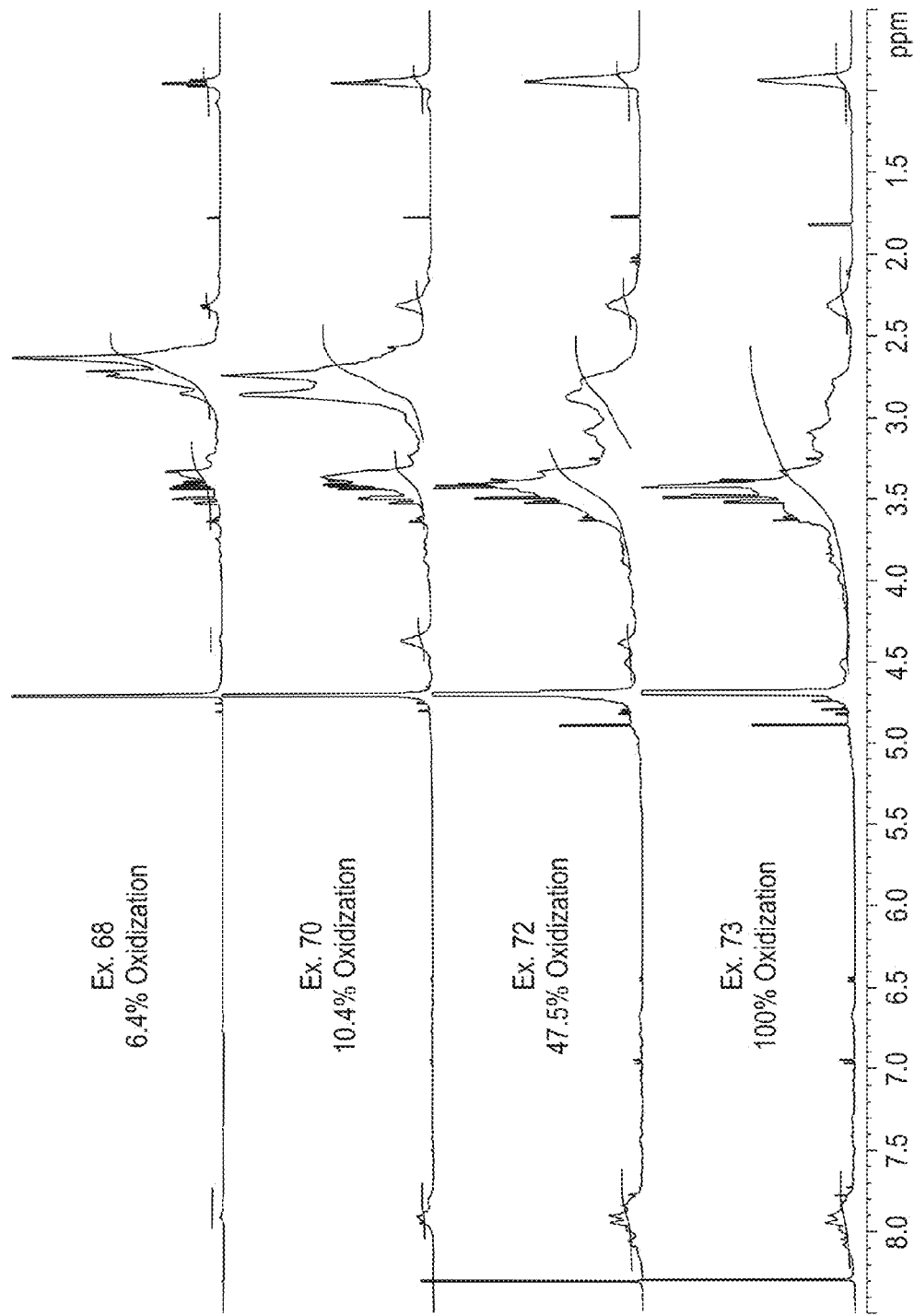
FIG. 12 is a set of $^1$H NMR spectra of Examples 68, 70, 72, and 73 showing different levels of hydrogen peroxide oxidation of LPEI25.

FIG. 12 is a set of proton NMR spectra of Examples 68, 70, 72, and 73 showing different levels of oxidation of LPEI25.

Table 6 summarizes the oxidation conditions, the % oxidation of ethylenimine (EI) units as determined by NMR, and the MICs against E. coli, S. aureus, and C. albicans of each hydrogen peroxide oxidized LPEI25 and BPEI25 sample (Examples 61-86). Only Examples 74-81 of Table 6 were acidified before testing against the microbes.

TABLE 6

| Example | Polymer | Conditions | $H_2O_2$ mole % | EI % oxidation | Color | MIC (mg/L) E. coli | S. aureus | C. albicans |
|---|---|---|---|---|---|---|---|---|
| 61 | LPEI25 | 85 C. | 10 | 7.8 | yellow | 250 | 125 | 62.5 |
| 62 | LPEI25 | 85 C. | 20 | 11.5 | yellow | 1000 | 250 | 250 |
| 63 | LPEI25 | 85 C. | 30 | 17.3 | yellow | >1000 | >1000 | 500 |
| 64 | LPEI25 | 85 C. | 50 | 44.6 | brown | >1000 | >1000 | >1000 |
| 65 | LPEI25 | 85 C. | 75 | 100.0 | brown | >1000 | >1000 | >1000 |
| 66 | LPEI25 | 85 C. | 100 | 100.0 | brown | | | |
| 67 | LPEI25 | r.t. | 10 | 6.2 | white | | | |
| 68 | LPEI25 | r.t. (not soluble) | 20 | 6.4 | white | 500 | 31.3 | 62.5 |
| 69 | LPEI25 | r.t. | 30 | 6.9 | white | 1000 | 62.5 | 62.5 |
| 70 | LPEI25 | r.t. | 50 | 10.4 | yellow | >1000 | 1000 | >1000 |
| 71 | LPEI25 | r.t. | 75 | 28.2 | yellow | >1000 | >1000 | >1000 |
| 72 | LPEI25 | r.t. | 100 | 47.5 | yellow | >1000 | >1000 | >1000 |
| 73 | LPEI25 | r.t. | 200 | 100.0 | white | >1000 | >1000 | >1000 |
| 74 | LPEI25 | pH 2.3, r.t. | 5 | 2.3 | white | 31.3 | 15.6 | 62.5 |
| 75 | LPEI25 | pH 2.3, r.t. | 10 | 2.8 | white | | | |
| 76 | LPEI25 | pH 2.3, r.t. | 20 | 3.8 | white | 31.3 | 15.6 | 31.3 |
| 77 | LPEI25 | pH 2.3, r.t. | 30 | 4.2 | white | | | |
| 78 | LPEI25 | pH 2.3, r.t. | 50 | 5.8 | white | 31.3 | 31.3 | 31.3 |
| 79 | LPEI25 | pH 2.3, r.t. | 75 | 6.5 | yellow | | | |
| 80 | LPEI25 | pH 2.3, r.t. | 100 | 7.0 | yellow | 31.3 | 31.3 | 62.5 |
| 81 | LPEI25 | pH 2.3, r.t. | 200 | 8.6 | yellow | 62.5 | 31.3 | 62.5 |
| 82 | BPEI25 | r.t. | 10 | 11.7 | white | >1000 | 31.3 | 15.6 |
| 83 | BPEI25 | r.t. | 25 | 24.9 | white | >1000 | 31.3 | 15.6 |
| 84 | BPEI25 | r.t. | 50 | 43.4 | white | >1000 | 62.5 | 62.5 |
| 85 | BPEI25 | r.t. | 75 | 56.3 | white | >1000 | 500 | 500 |
| 86 | BPEI25 | r.t. | 100 | 71.9 | yellowish | >1000 | >1000 | >1000 |

Figure 13:
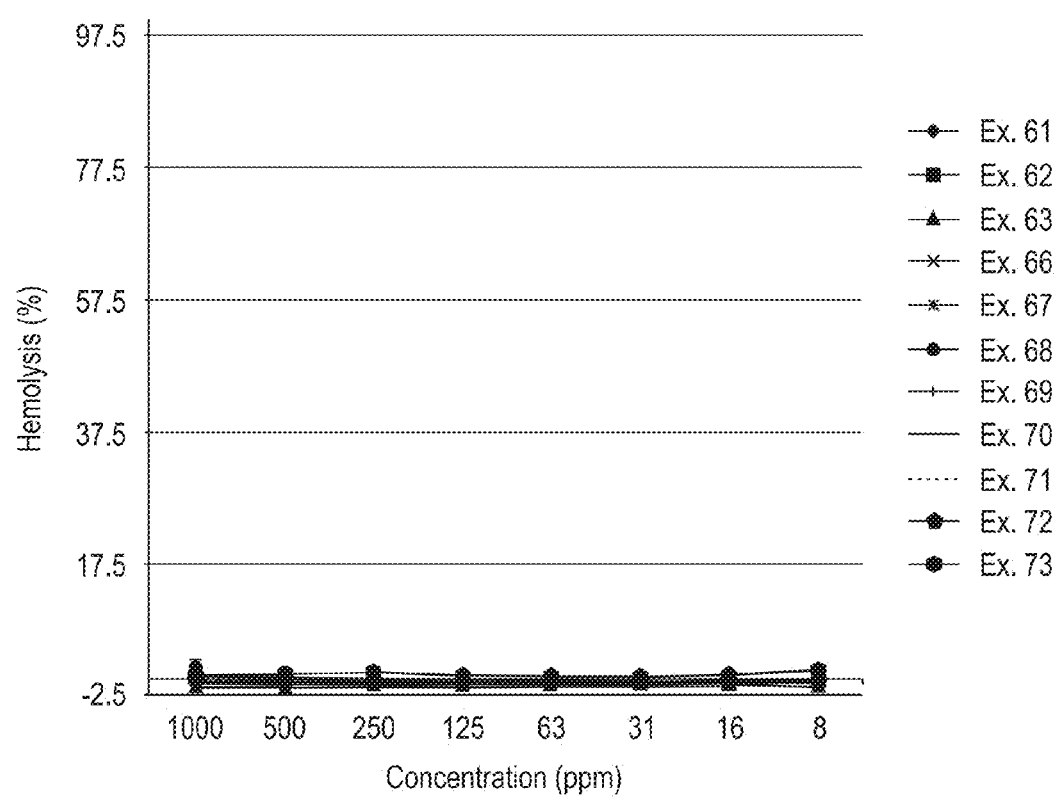
FIG. 13 is a bar graph showing the hemolysis behavior of hydrogen peroxide oxidized LPEI25 samples of Examples 61-63 and 66-73 at concentrations as high as 1000 mg/L.
Figure 14:
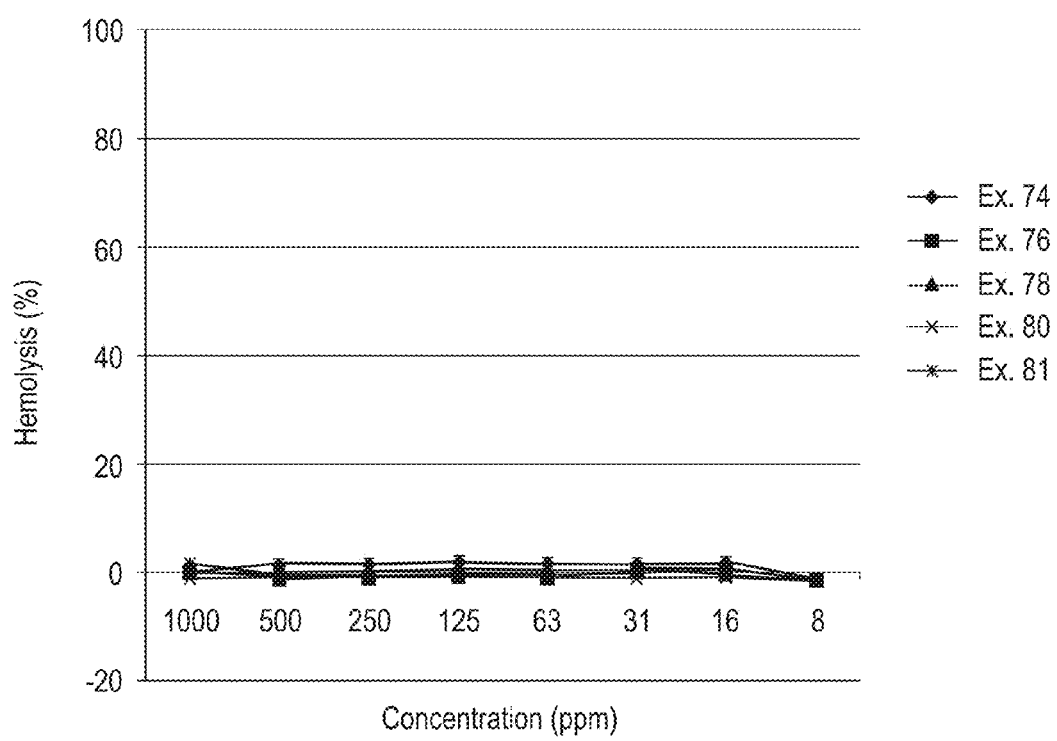
FIG. 14 is a bar graph showing the hemolysis behavior of hydrogen peroxide oxidized LPEI25 samples of Examples 74, 76, 78, 80 and 81 at concentrations as high as 1000 mg/L.
Figure 15:
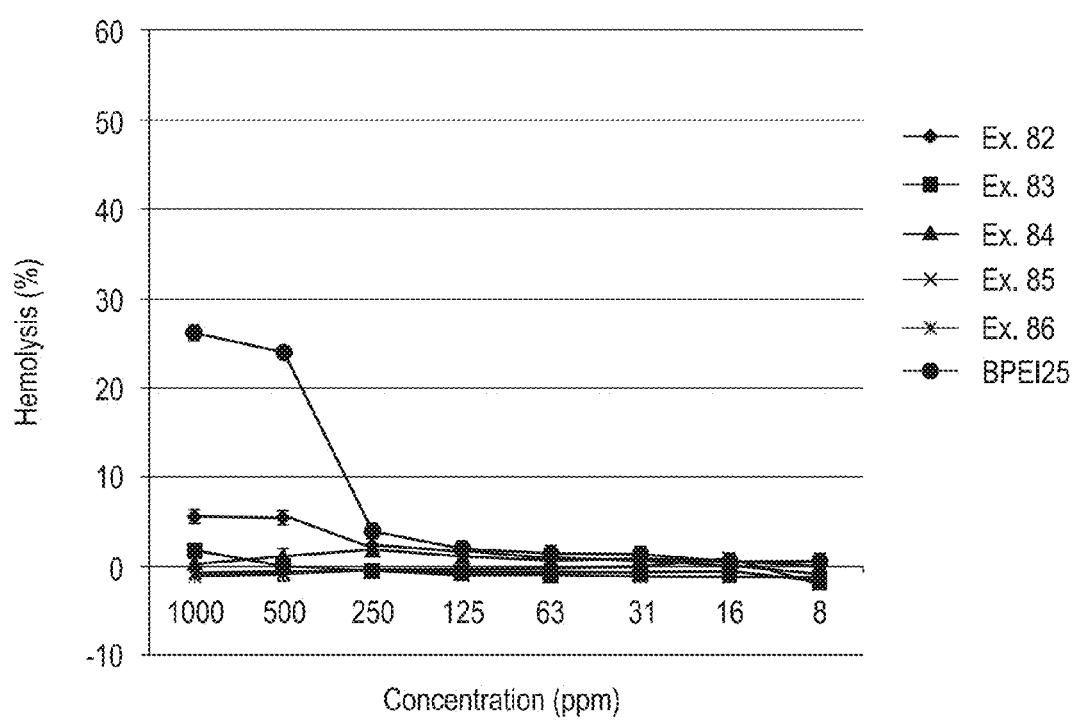
FIG. 15 is a bar graph showing the hemolysis behavior of hydrogen peroxide oxidized BPEI25 samples of Examples 82-86 compared to BPEI25 at concentrations as high as 1000 mg/L.

The results of Table 6 indicate that for each condition used and each polymer used (LPEI25 and BPEI25), the activity against the microbes decreased with increasing oxidation level of the LPEI25 and BPEI25. However, every oxidized LPEI25 and BPEI25 sample was non-hemolytic (FIGS. 13, 14, and 15) at concentrations up to 1000 mg/L. The smallest level of oxidation (2.3%, Example 74) was effective in rendering the LPEI25 and BPEI25 non-hemolytic to red blood cells without significantly altering the intrinsic antimicrobial properties of the LPEI25 and BPEI25.

Other Hemolysis Data

Figure 16:
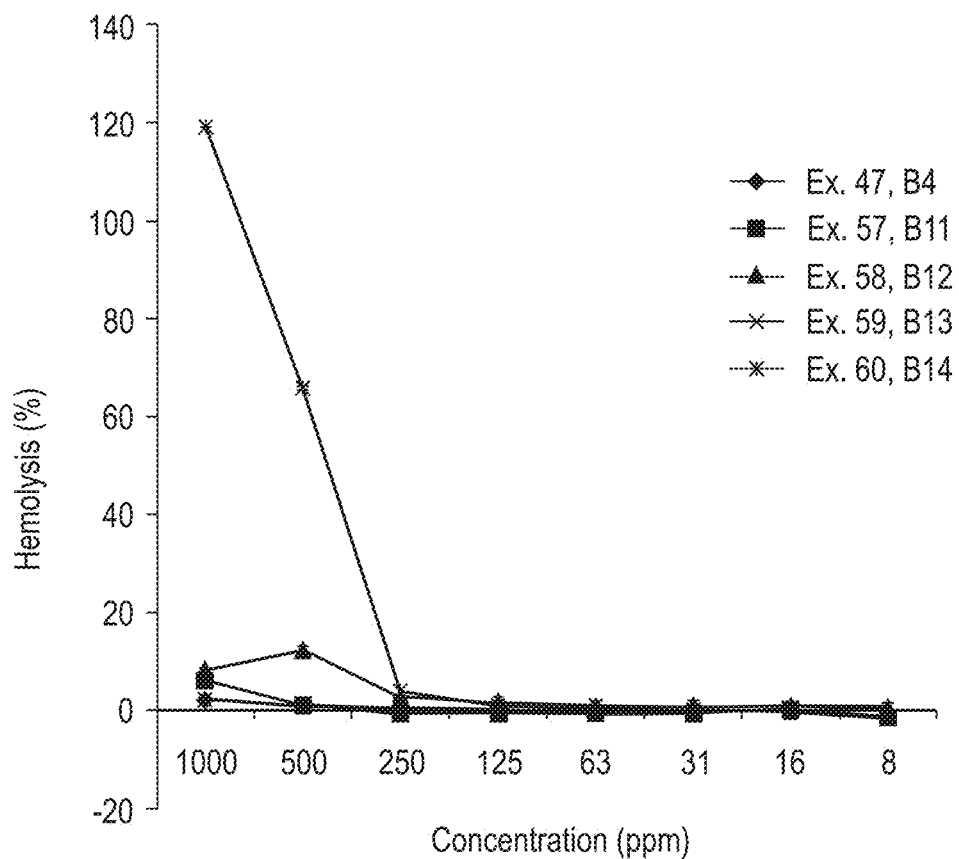
FIG. 16 is a graph showing the hemolysis behavior of Examples 47 and 57-60 for concentrations as high as 1000 mg/L.

FIG. 16 is a bar graph showing the hemolysis behavior of B4 (Example 47) and B11-B14 (Examples 57-60, respectively) for concentrations as high as 1000 mg/L. Only B14 (Example 60) was significantly hemolytic at 250-1000 mg/L.

Cytotoxicity

The cytotoxicity of the polymers was studied using the standard MTT assay protocol on IMR-90 (human lung fibroblast cells). The polymers L14, B4, B10, and BPEI25 were used for treatment of the cells. IMR-90 cells were seeded onto 96-well plates at the density of 10000 cells per well, and allowed to grow overnight to 60% to 70% confluency before treatment. Each of the polymers was diluted using Dulbecco's modified Eagle medium (DMEM, Invitrogen, Singapore) supplemented with 10% fetal bovine serum (FBS, Invitrogen, Singapore) and PSG (penicillin at 100 U/mL, streptomycin at 100 µg/mL, and L-glutamine at 2 mM, Invitrogen, Singapore) to a series of concentrations: 1000, 500, 250, 125, 62.5, 31.3, 15.6, and 7.8 ppm. The cells in each well were then incubated with 100 microliters of growth medium containing various concentrations of polymers or 100 microliters of fresh medium for 24 hours at 37° C. Following incubation, 100 microliters of growth medium and 20 microliters of MTT solution (5 mg/mL in PBS) were then added to each well and the cells were incubated for 4 hours at 37° C. Formazan crystals formed in each well were solubilized using 150 microliters of DMSO upon removal of growth media. A 100 microliter aliquot from each well was then transferred to a new 96-well plate for determination of absorbance using a microplate spectrophotometer at wavelengths of 550 nm and 690 nm. Relative cell viability was expressed as $[(A_{550}-A_{690})$ sample/$(A_{550}-A_{690})$control]×100%. Data were expressed as mean±standard deviations of four replicates.

Figure 17:
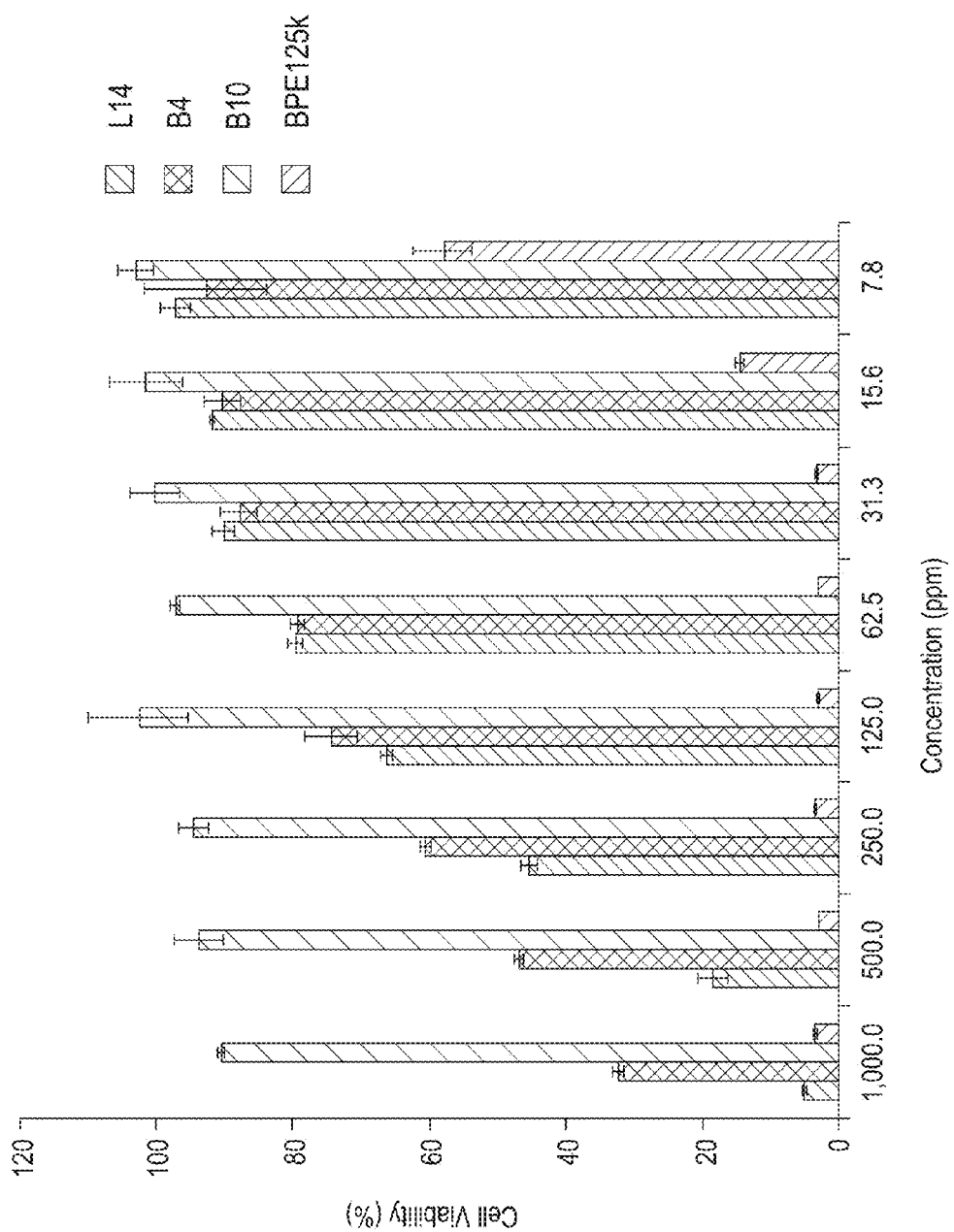
FIG. 17 is a bar chart comparing the cytotoxicity behavior of L14, B4, B10, and BPEI25.

FIG. 17 is a bar chart comparing the cytotoxicity of L14, B4, B10, and BPEI25. L14 and B4 were not toxic to the human lung cell line IMR-90 even at 8×MIC (i.e., MIC against TB mycobacteria) after incubation for 24 hours. As-purchased LPEI25 (L2) precipitated from the growth medium and was not further tested.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A method, comprising:
   treating a medical condition caused by at least one bacterium by contacting the bacterium with a cationic polyamine, thereby killing the bacterium, wherein the cationic polyamine has a polymer backbone comprising:
   i) a positive-charged first ethylenimine unit of formula (2):

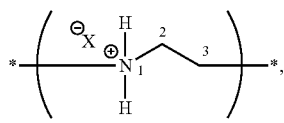
(2)

wherein $X^\ominus$ is a negative-charged counterion bound by non-covalent association with the positive charged nitrogen labeled 1, and
   ii) a non-charged second ethylenimine unit of formula (3):

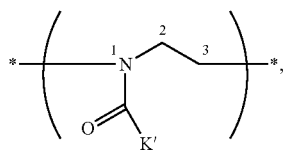
(3)

wherein K' comprises at least one carbon;
and wherein
no backbone nitrogen of the cationic polyamine is present as a quaternary ammonium salt,
the cationic polyamine has a hemolysis HC20 value of greater than 1000 mg/L, and
the first ethylenimine unit and the second ethylenimine unit of the polymer backbone are directly and/or indirectly covalently linked.

2. The method of claim 1, wherein the first ethylenimine unit and the second ethylenimine unit are linked in a head to tail arrangement, wherein a nitrogen labeled 1 is the head and a carbon labeled 3 is the tail.

3. The method of claim 1, wherein the bacterium is a *mycobacterium*.

4. The method of claim 1, wherein K' is a $C_1$-$C_{10}$ alkyl group.

5. The method of claim 1, wherein K' comprises a urea group.

6. The method of claim 1, wherein K' comprises a group that completes a urea group with the backbone nitrogen labeled 1.

7. The method of claim 1, wherein the cationic polyamine is a linear cationic polyamine having one polymer chain branch and two peripheral polymer chain ends.

8. The method of claim 1, wherein the cationic polyamine is a branched cationic polyamine having two or more intersecting polymer chain branches and three or more peripheral polymer chain ends.

9. The method of claim 1, wherein K' is ethyl.

10. The method of claim 1, wherein the cationic polyamine comprises the first ethylenimine unit and the second ethylenimine unit in a molar ratio of about 1:1 to about 400:1, respectively.

11. The method of claim 1, wherein the polymer backbone of the cationic polyamine comprises an oxidized ethylenimine unit (third ethylenimine unit) of formula (7):

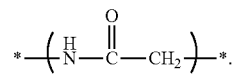
(7)

12. The method of claim 1, wherein *—C(=O)—K' of formula (3) has a structure selected from the group consisting of:

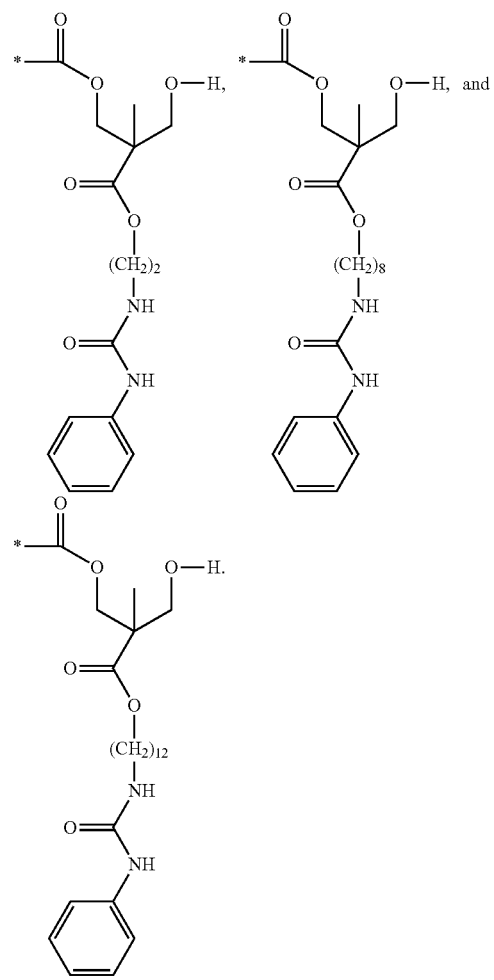

13. The method of claim 1, wherein the non-charged second ethylenimine unit of formula (3) has a structure according to formula (6):

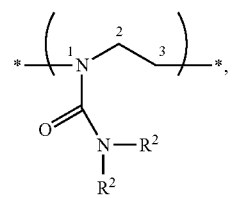
(6)

wherein each $R^2$ is a monovalent radical independently selected from the group consisting of hydrogen, alkyl groups comprising 1 to 30 carbons, and aryl groups comprising 6 to 30 carbons, and wherein at least one $R^2$ comprises at least one carbon.

14. A drug, comprising:

a cationic polyamine, wherein the cationic polyamine has a polymer backbone comprising:

i) a positive-charged first ethylenimine unit of formula (2):

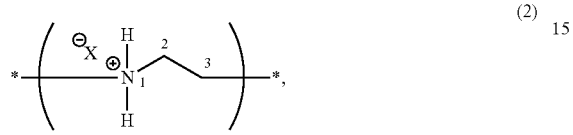

(2)

wherein $X^{\oplus}$ is a negative-charged counterion bound by non-covalent association with the positive charged nitrogen labeled 1, and ii) a non-charged second ethylenimine unit of formula (3):

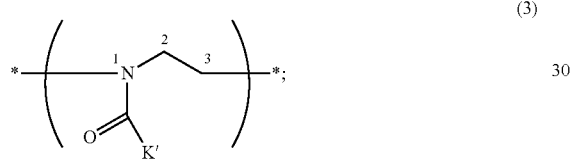

(3)

wherein K' comprises at least one carbon;

and wherein no backbone nitrogen of the cationic polyamine is present as a quaternary ammonium salt, the first ethylenimine unit and the second ethylenimine unit are directly and/or indirectly covalently linked, the drug is effective in killing a bacterium, and the drug has a hemolysis HC20 value of greater than 1000 mg/L.

15. The drug of claim 14, wherein the drug is effective in killing a *mycobacterium*.

16. The drug of claim 14, wherein the drug has the form of an injectable solution, the solution comprising the cationic polyamine and water.

17. The drug of claim 14, wherein the drug has the form of a pill.

18. The drug of claim 14, wherein the drug has the form of an ointment.

19. A method, comprising:

forming a mixture comprising i) a base polyamine selected from the group consisting of polyethylenimines, partially N-acylated polyethylenimines, and combinations thereof, and ii) a solvent, treating the mixture with oxygen and/or a peroxide, thereby forming an oxidized base polyamine; and treating the oxidized base polyamine with a protic acid, thereby forming an oxidized cationic polyamine having a polymer backbone that comprises:

a positive-charged first ethylenimine unit of formula (2):

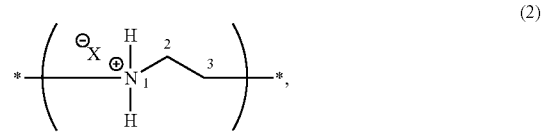

(2)

wherein $X^{\oplus}$ is a negative-charged counterion bound by non-covalent association with the positive charged nitrogen labeled 1, and an oxidized ethylenimine unit of formula (7):

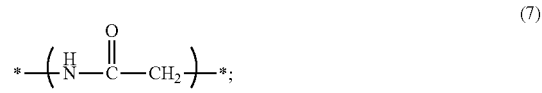

(7)

wherein no backbone nitrogen of the cationic polyamine is present as a quaternary ammonium salt, the first ethylenimine unit and the oxidized ethylenimine unit are directly and/or indirectly covalently linked, the cationic polyamine is effective in killing a bacterium, and the cationic polyamine has a hemolysis HC20 value of greater than 1000 mg/L.

20. An antimicrobial film, wherein the film comprises a cationic polyamine having a polymer backbone that comprises:

i) a positive-charged first ethylenimine unit of formula (2):

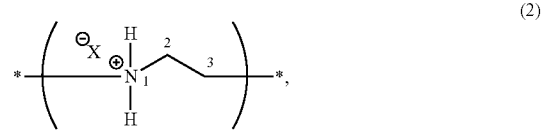

(2)

wherein $X^{\oplus}$ is a negative-charged counterion bound by non-covalent association with the positive charged nitrogen labeled 1, and ii) a non-charged second ethylenimine unit of formula (3):

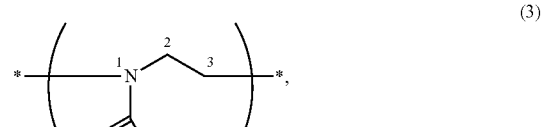

(3)

wherein K' comprises at least one carbon;

and wherein no backbone nitrogen of the cationic polyamine is present as a quaternary ammonium salt, the first ethylenimine unit and the second ethylenimine unit are directly and/or indirectly covalently linked.

21. The antimicrobial film of claim 20, wherein the film is effective in killing a fungus.

22. The antimicrobial film of claim 20, wherein the film is effective in inhibiting growth of a biofilm.

23. The antimicrobial film of claim 20, wherein the cationic polyamine of the film comprises an ethylenimine unit of formula (D-1):

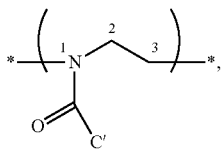
(D-1)

wherein C' comprises a catechol group.

24. The antimicrobial film of claim 23, wherein C' is a moiety selected from the group consisting of

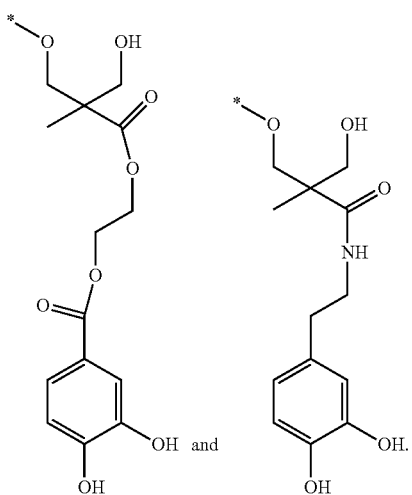 [SMILES: *OCC(C)(CO)C(=O)OCCOC(=O)c1ccc(O)c(O)c1 ; *OCC(C)(CO)C(=O)NCCc1ccc(O)c(O)c1]

25. An article, comprising the antimicrobial film of claim 20 disposed on a surface of an object.

26. The article of claim 25, wherein the object is selected from the group consisting of medical instruments, insertable medical devices, bandages, garments, gloves, facial masks, hygiene products, beverage containers, food packaging materials, and contact lenses.

27. The article of claim 25, wherein the object comprises a material selected from the group consisting of metals, alloys, composites, woods, plastics, rubbers, glasses, yarns, fibers, cloths, and combinations thereof.

28. The article of claim 25, wherein the object is a contact lens.

29. A method, comprising:
treating a medical condition caused by a *mycobacterium* by contacting the *mycobacterium* with a cationic polyamine, thereby killing the *mycobacterium*, wherein the cationic polyamine has a polymer backbone comprising:
i) a positive-charged first ethylenimine unit of formula (2):

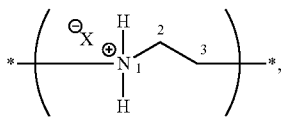
(2)

wherein $X^\oplus$ is a negative-charged counterion bound by non-covalent association with the positive charged nitrogen labeled 1, and
ii) a non-charged second ethylenimine unit of formula (3):

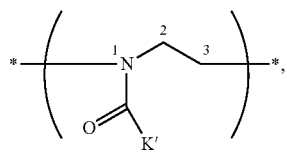
(3)

wherein K' comprises at least one carbon;
and wherein
the cationic polyamine has a hemolysis HC20 value of greater than 1000 mg/L, and
the first ethylenimine unit and the second ethylenimine unit of the polymer backbone are directly and/or indirectly covalently linked.

30. A method, comprising:
treating a medical condition caused by at least one bacterium by contacting the bacterium with a cationic polyamine, thereby killing the bacterium, wherein the cationic polyamine has a polymer backbone comprising:
i) a positive-charged first ethylenimine unit of formula (2):

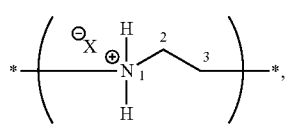
(2)

wherein $X^\oplus$ is a negative-charged counterion bound by non-covalent association with the positive charged nitrogen labeled 1, and
ii) a non-charged second ethylenimine unit of formula (3):

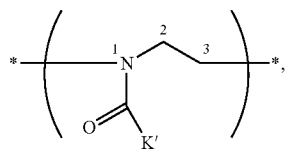
(3)

wherein K' comprises a urea group;
and wherein
the cationic polyamine has a hemolysis HC20 value of greater than 1000 mg/L, and
the first ethylenimine unit and the second ethylenimine unit of the polymer backbone are directly and/or indirectly covalently linked.

31. A method, comprising:
treating a medical condition caused by at least one bacterium by contacting the bacterium with a cationic polyamine, thereby killing the bacterium, wherein the cationic polyamine has a polymer backbone comprising:

i) a positive-charged first ethylenimine unit of formula (2):

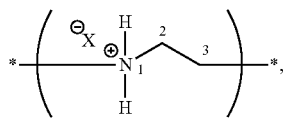
(2)

wherein $X^{\ominus}$ is a negative-charged counterion bound by non-covalent association with the positive charged nitrogen labeled 1, and ii) a non-charged second ethylenimine unit of formula (3):

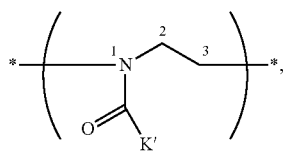
(3)

wherein *—C(=O)—K' of formula (3) has a structure selected from the group consisting of:

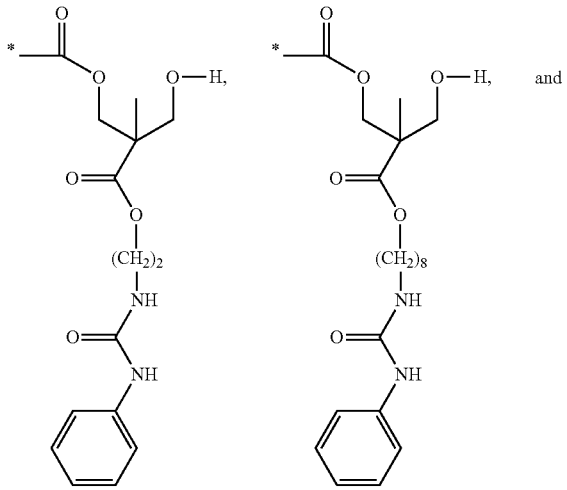 and

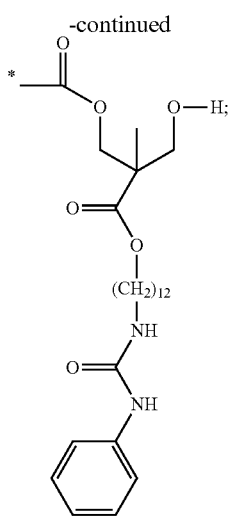

and wherein
the cationic polyamine has a hemolysis HC20 value of greater than 1000 mg/L, and
the first ethylenimine unit and the second ethylenimine unit of the polymer backbone are directly and/or indirectly covalently linked.

32. The method of claim 19, wherein the polymer backbone comprises a non-charged second ethylenimine unit of formula (3):

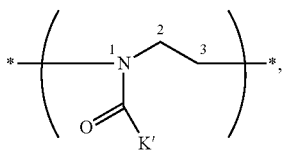
(3)

wherein K' comprises at least one carbon.

33. The method of claim 32, wherein K' is a $C_1$-$C_{10}$ alkyl group.

34. The method of claim 32, wherein K' is ethyl.

35. The method of claim 32, wherein K' comprises a urea group.

36. The method of claim 19, wherein the method comprises treating the base polyamine with an N-acylating agent comprising a cyclic carbonate group.

37. The method of claim 19, wherein the base polyamine is a linear polyethylenimine.

38. The method of claim 19, wherein the base polyamine is a partially N-acylated polyethylenimine.

39. The method of claim 19, wherein the base polyamine is a branched polyethylenimine.

40. The method of claim 19, wherein the oxidized cationic polyamine comprises the oxidized ethylenimine unit in an amount between 0 mol % and 5 mol % based on total moles of backbone nitrogens of the oxidized cationic polyamine.

* * * * *